US011878145B2

(12) United States Patent
Haidar

(10) Patent No.: US 11,878,145 B2
(45) Date of Patent: Jan. 23, 2024

(54) CLOSED LOOP CONTROL OF PHYSIOLOGICAL GLUCOSE

(71) Applicant: Ypsomed AG, Burgdorf (CH)

(72) Inventor: Ahmad Mohamad Haidar, Montreal (CA)

(73) Assignee: Ypsomed AG, Burgdorf (CH)

( * ) Notice: Subject to any disclaimer, the term of this patent is extended or adjusted under 35 U.S.C. 154(b) by 846 days.

(21) Appl. No.: 16/608,054

(22) PCT Filed: May 3, 2018

(86) PCT No.: PCT/US2018/030771

§ 371 (c)(1),
(2) Date: Oct. 24, 2019

(87) PCT Pub. No.: WO2018/204568

PCT Pub. Date: Nov. 8, 2018

(65) Prior Publication Data

US 2020/0197605 A1 Jun. 25, 2020

Related U.S. Application Data

(60) Provisional application No. 62/536,541, filed on Jul. 25, 2017, provisional application No. 62/501,976, filed on May 5, 2017.

(51) Int. Cl.

| | |
|---|---|
| ***A61M 5/142*** | (2006.01) |
| ***A61M 5/172*** | (2006.01) |
| ***G16H 20/17*** | (2018.01) |
| ***G16H 50/50*** | (2018.01) |

(Continued)

(52) U.S. Cl.
CPC ......... *A61M 5/1723* (2013.01); *A61B 5/7275* (2013.01); *G16H 20/17* (2018.01); *G16H 50/20* (2018.01); *G16H 50/50* (2018.01); *A61M 2202/0486* (2013.01)

(58) Field of Classification Search
CPC ........ A61M 5/1723; A61M 2202/0486; A61B 5/7275
See application file for complete search history.

(56) References Cited

U.S. PATENT DOCUMENTS

| | | | |
|---|---|---|---|
| 4,475,901 | A | 10/1984 | Kraegen et al. |
| 5,822,715 | A | 10/1998 | Worthington et al. |
| 5,853,364 | A | 12/1998 | Baker, Jr. et al. |

(Continued)

FOREIGN PATENT DOCUMENTS

| | | |
|---|---|---|
| CN | 104667379 A | 6/2015 |
| JP | 2007267870 | 10/2007 |

(Continued)

OTHER PUBLICATIONS

Cobelli, C., Renard, E., & Kovatchev, B. (2011). Artificial pancreas: Past, Present, Future. *Diabetes*, 60(11), 2672-2682.

(Continued)

*Primary Examiner* — Nathan R Price
*Assistant Examiner* — Tania Ismail
(74) *Attorney, Agent, or Firm* — Dorsey & Whitney LLP

(57) ABSTRACT

The present disclosure relates to systems and methods for controlling physiological glucose concentrations in a patient using a closed loop artificial pancreas. The systems and methods may utilize a controller with control logic operative to execute a multi-model predictive controller algorithm to determine a medication dose to the patient.

28 Claims, 27 Drawing Sheets

(51) Int. Cl.
*G16H 50/20* (2018.01)
*A61B 5/00* (2006.01)

(56) References Cited

U.S. PATENT DOCUMENTS 5,938,594 A 8/1999 Poon et al.
5,971,922 A 10/1999 Arita et al.
6,083,172 A 7/2000 Baker, Jr. et al.
6,175,752 B1 1/2001 Say et al.
6,269,314 B1 7/2001 Iitawaki et al.
6,459,939 B1 10/2002 Hugo
6,544,212 B2 4/2003 Galley et al.
6,558,351 B1 5/2003 Steil et al.
6,572,545 B2 6/2003 Knobbe et al.
6,575,905 B2 6/2003 Knobbe et al.
6,691,043 B2 2/2004 Ribeiro, Jr.
6,740,072 B2 5/2004 Starkweather et al.
6,827,702 B2 12/2004 Lebel et al.
6,923,763 B1 8/2005 Kovatchev et al.
7,022,072 B2 4/2006 Fox et al.
7,025,743 B2 4/2006 Mann et al.
7,060,059 B2 6/2006 Keith et al.
7,267,665 B2 9/2007 Steil et al.
7,278,983 B2 10/2007 Ireland et al.
7,354,420 B2 4/2008 Steil et al.
7,389,133 B1 6/2008 Kotulla et al.
7,395,216 B2 7/2008 Rosenfeld et al.
7,399,277 B2 7/2008 Saidara et al.
7,402,153 B2 7/2008 Steil et al.
7,491,187 B2 2/2009 Van Den Berghe et al.
7,547,281 B2 6/2009 Hayes et al.
7,569,030 B2 8/2009 Lebel et al.
7,590,443 B2 9/2009 Bharmi
7,651,845 B2 1/2010 Doyle, III et al.
7,704,226 B2 4/2010 Mueller, Jr. et al.
7,727,147 B1 6/2010 Osorio et al.
7,766,830 B2 8/2010 Fox et al.
7,766,831 B2 8/2010 Essenpreis et al.
7,778,680 B2 8/2010 Goode, Jr. et al.
7,785,313 B2 8/2010 Mastrototaro
7,806,854 B2 10/2010 Damiano et al.
7,806,886 B2 10/2010 Kanderian, Jr. et al.
7,819,843 B2 10/2010 Mann et al.
7,850,641 B2 12/2010 Lebel et al.
7,860,544 B2 12/2010 Say et al.
7,879,026 B2 2/2011 Estes et al.
7,890,295 B2 2/2011 Shin et al.
7,899,545 B2 3/2011 John
7,901,394 B2 3/2011 Ireland et al.
7,912,684 B2 3/2011 Brown
7,920,998 B2 4/2011 Brown
7,925,321 B2 4/2011 Goode et al.
7,937,255 B2 5/2011 Brown
7,941,200 B2 5/2011 Weinert et al.
7,959,569 B2 6/2011 Goode et al.
7,963,917 B2 6/2011 Kellogg et al.
7,988,630 B1 8/2011 Osorio et al.
8,062,249 B2 11/2011 Wilinska et al.
8,088,098 B2 1/2012 Yodfat et al.
8,105,268 B2 1/2012 Lebel et al.
8,109,921 B2 2/2012 Estes et al.
8,112,375 B2 2/2012 Pav
8,114,023 B2 2/2012 Ward et al.
8,140,312 B2 3/2012 Hayter et al.
8,152,789 B2 4/2012 Starkweather et al.
8,162,829 B2 4/2012 Say et al.
8,177,716 B2 5/2012 Say et al.
8,192,395 B2 6/2012 Estes et al.
8,208,984 B2 6/2012 Blomquist et al.
8,226,556 B2 7/2012 Hayes et al.
8,229,872 B2 7/2012 Gilhuly
8,257,300 B2 9/2012 Budiman et al.
8,273,052 B2 9/2012 Damiano et al.
8,287,487 B2 10/2012 Estes
8,290,562 B2 10/2012 Goode, Jr. et al.
8,318,154 B2 11/2012 Frost et al.
8,346,399 B2 1/2013 Blomquist
8,348,886 B2 1/2013 Kanderian, Jr. et al.
8,348,923 B2 1/2013 Kanderian, Jr. et al.
8,377,031 B2 2/2013 Hayter et al.
8,398,616 B2 3/2013 Budiman
8,409,131 B2 4/2013 Say et al.
8,414,523 B2 4/2013 Blomquist et al.
8,449,524 B2 5/2013 Braig et al.
8,460,231 B2 6/2013 Brauker et al.
8,467,972 B2 6/2013 Rush
8,478,557 B2 7/2013 Hayter et al.
8,480,580 B2 7/2013 Wolpert et al.
8,480,649 B2 7/2013 Yodfat et al.
8,504,179 B2 8/2013 Blomquist
8,527,208 B2 9/2013 Prud'homme et al.
8,532,933 B2 9/2013 Duke et al.
8,548,544 B2 10/2013 Kircher, Jr. et al.
8,560,082 B2 10/2013 Wei
8,562,587 B2 10/2013 Kovatchev et al.
8,579,854 B2 11/2013 Budiman et al.
8,585,591 B2 11/2013 Sloan et al.
8,585,593 B2 11/2013 Kovatchev et al.
8,585,637 B2 11/2013 Wilinska et al.
8,597,274 B2 12/2013 Sloan et al.
8,615,366 B2 12/2013 Galley et al.
8,622,988 B2 1/2014 Hayter
8,647,321 B2 2/2014 Budiman
8,657,807 B2 2/2014 Blomquist
8,660,800 B2 2/2014 Von Busch et al.
8,688,386 B2 4/2014 Shadforth et al.
8,690,820 B2 4/2014 Cinar et al.
8,690,856 B2 4/2014 Blomquist
8,718,943 B2 5/2014 Moerman
8,718,965 B2 5/2014 Hayter et al.
8,732,188 B2 5/2014 Doniger et al.
8,734,422 B2 5/2014 Hayter
8,734,428 B2 5/2014 Blomquist
8,744,545 B2 6/2014 Say et al.
8,753,316 B2 6/2014 Blomquist
8,756,043 B2 6/2014 Albisser et al.
8,762,070 B2 6/2014 Doyle, III et al.
8,771,222 B2 7/2014 Kanderian, Jr. et al.
8,777,896 B2 7/2014 Starkweather et al.
8,777,924 B2 7/2014 Kanderian, Jr. et al.
8,784,369 B2 7/2014 Starkweather et al.
8,784,370 B2 7/2014 Lebel et al.
8,788,044 B2 7/2014 John
8,795,224 B2 8/2014 Starkweather et al.
8,795,252 B2 8/2014 Hayter
8,821,433 B2 9/2014 Blomquist
8,823,528 B2 9/2014 Blomquist
8,825,166 B2 9/2014 John
8,831,735 B2 9/2014 John
8,840,553 B2 9/2014 Say et al.
8,840,582 B2 9/2014 Blomquist et al.
8,876,755 B2 11/2014 Taub et al.
8,876,803 B2 11/2014 Budiman
8,924,160 B2 12/2014 Moerman
8,924,161 B2 12/2014 Moerman
8,926,585 B2 1/2015 Brauker et al.
8,930,203 B2 1/2015 Kiaie et al.
8,932,216 B2 1/2015 Jennewine
8,936,573 B2 1/2015 Blomquist
8,945,094 B2 2/2015 Nordh
8,954,373 B2 2/2015 Atlas et al.
8,961,416 B2 2/2015 Siddiqui et al.
8,961,465 B2 2/2015 Blomquist
8,965,509 B2 2/2015 John
8,974,439 B2 3/2015 Estes
8,977,504 B2 3/2015 Hovorka
8,998,878 B2 4/2015 Blomquist
9,017,311 B2 4/2015 Budiman
9,037,254 B2 5/2015 John
9,056,167 B2 6/2015 Pesach et al.
9,056,168 B2 6/2015 Kircher, Jr. et al.
9,066,694 B2 6/2015 Say et al.
9,089,292 B2 7/2015 Roy et al.
9,089,713 B2 7/2015 John

(56) References Cited

U.S. PATENT DOCUMENTS 9,114,210 B2 8/2015 Estes
9,119,528 B2 9/2015 Cobelli et al.
9,192,750 B2 11/2015 Pettis et al.
9,199,031 B2 12/2015 Yodfat et al.
9,220,456 B2 12/2015 Bashan et al.
9,227,014 B2 1/2016 Buckingham et al.
9,244,077 B2 1/2016 Yodfat et al.
9,254,362 B2 2/2016 Estes et al.
9,283,323 B2 3/2016 Toumazou et al.
9,302,045 B2 4/2016 Rule
9,320,471 B2 4/2016 Hayes et al.
9,323,898 B2 4/2016 Sloan et al.
9,330,237 B2 5/2016 Cohen et al.
9,333,298 B2 5/2016 Kim et al.
9,364,609 B2 6/2016 Keenan et al.
9,364,679 B2 6/2016 John
9,398,869 B2 7/2016 Kovatchev et al.
9,399,096 B2 7/2016 Keenan et al.
9,402,953 B2 8/2016 Wilinska et al.
9,420,968 B2 8/2016 Kamath et al.
9,440,025 B2 9/2016 Kanderian, Jr. et al.
9,445,757 B2 9/2016 Desborough et al.
9,457,145 B2 10/2016 Yodfat et al.
9,474,855 B2 10/2016 McCann et al.
9,480,796 B2 11/2016 Starkweather et al.
9,483,619 B2 11/2016 Booth et al.
9,486,171 B2 11/2016 Saint
9,486,578 B2 11/2016 Finan et al.
9,507,917 B2 11/2016 Atlas et al.
9,510,782 B2 12/2016 Kamath et al.
9,517,306 B2 12/2016 Morales
9,526,834 B2 12/2016 Keenan et al.
9,572,934 B2 2/2017 Hayter
9,579,456 B2 2/2017 Budiman et al.
9,597,451 B2 3/2017 Yodfat et al.
9,610,046 B2 4/2017 Hayter
9,619,625 B2 4/2017 Bengtsson
9,623,179 B2 4/2017 Mastrototaro et al.
9,629,957 B2 4/2017 Sigrist et al.
9,636,461 B2 5/2017 Bengtsson et al.
9,649,439 B2 5/2017 John
9,662,445 B2 5/2017 Parikh et al.
9,669,160 B2 6/2017 Harris et al.
9,669,162 B2 6/2017 Sloan et al.
9,687,194 B2 6/2017 Cantwell et al.
9,693,700 B2 7/2017 Tan et al.
9,694,133 B2 7/2017 Kircher, Jr. et al.
9,700,708 B2 7/2017 Doyle, III et al.
9,717,848 B2 8/2017 Geismar et al.
9,724,470 B2 8/2017 Day et al.
9,750,438 B2 9/2017 Kovatchev et al.
9,757,510 B2 9/2017 Finan
9,782,540 B2 10/2017 Lebel et al.
9,795,737 B2 10/2017 Finan et al.
9,808,577 B2 11/2017 Nagar et al.
9,833,177 B2 12/2017 Blomquist
9,833,191 B2 12/2017 Mazlish
9,833,570 B2 12/2017 El-Khatib et al.
9,833,571 B2 12/2017 Budiman
9,844,627 B2 12/2017 Estes
9,848,774 B2 12/2017 Bergstrom et al.
9,849,239 B2 12/2017 Grosman et al.
9,861,310 B2 1/2018 O'Connell
9,861,747 B2 1/2018 Chovanda et al.
9,861,748 B2 1/2018 Mastrototaro et al.
9,872,890 B2 1/2018 Davidson et al.
9,878,096 B2 1/2018 Roy et al.
9,878,097 B2 1/2018 Estes
9,886,556 B2 2/2018 Booth et al.
9,889,250 B2 2/2018 Blomquist et al.
9,907,515 B2 3/2018 Doyle, III et al.
9,907,909 B2 3/2018 Finan et al.
9,913,599 B2 3/2018 Bernstein et al.
9,918,635 B2 3/2018 Bousamra et al.
9,919,105 B2 3/2018 Yodfat et al.
9,936,910 B2 4/2018 Hayter et al.
9,943,644 B2 4/2018 Hayter
9,943,645 B2 4/2018 Monirabbasi et al.
9,965,596 B2 5/2018 Booth et al.
9,984,773 B2 5/2018 Gondhalekar et al.
9,990,581 B2 6/2018 Carlsgaard et al.
9,999,728 B2 6/2018 Parikh et al.
10,007,765 B2 6/2018 Nogueira et al.
10,010,273 B2 7/2018 Sloan et al.
10,016,561 B2 7/2018 Saint et al.
10,022,498 B2 7/2018 Ruchti et al.
10,046,113 B2 8/2018 Ruchti et al.
10,052,049 B2 8/2018 Blomquist et al.
10,080,529 B2 9/2018 Fox et al.
10,130,765 B2 11/2018 Budiman et al.
2003/0187337 A1 10/2003 Tarassenko et al.
2003/0195404 A1 10/2003 Knobbe et al.
2004/0034295 A1 2/2004 Salganicoff
2004/0044272 A1 3/2004 Moerman et al.
2004/0248204 A1 12/2004 Moerman
2005/0004439 A1 1/2005 Shin et al.
2005/0075274 A1 4/2005 Willman et al.
2005/0171503 A1 8/2005 Van Den Berghe et al.
2005/0197621 A1 9/2005 Poulsen et al.
2006/0253296 A1 11/2006 Liisberg et al.
2007/0016127 A1 1/2007 Staib et al.
2008/0183060 A1 7/2008 Steil et al.
2008/0206799 A1 8/2008 Blomquist
2008/0228056 A1 9/2008 Blomquist et al.
2009/0163402 A1 3/2009 Hayter
2009/0163781 A1 6/2009 Say et al.
2009/0227940 A1 9/2009 Say et al.
2009/0227941 A1 9/2009 Say et al.
2009/0318791 A1 12/2009 Kaastrup
2010/0049022 A1 2/2010 Parris et al.
2010/0057043 A1 3/2010 Kovatchev et al.
2010/0145262 A1 6/2010 Bengtsson et al.
2010/0160740 A1 6/2010 Cohen et al.
2010/0168543 A1 7/2010 Kamath et al.
2010/0168657 A1 7/2010 Kamath et al.
2010/0174228 A1 7/2010 Buckingham et al.
2010/0185073 A1 7/2010 Goode, Jr. et al.
2010/0249561 A1 9/2010 Patek et al.
2010/0262117 A1 10/2010 Magni et al.
2010/0292553 A1 11/2010 Say et al.
2010/0298681 A1 11/2010 Say et al.
2011/0077481 A1 3/2011 Say et al.
2011/0098548 A1 4/2011 Budiman et al.
2011/0184267 A1 7/2011 Duke et al.
2011/0313390 A1 12/2011 Roy et al.
2011/0313680 A1 12/2011 Doyle, III et al.
2012/0078067 A1 3/2012 Kovatchev et al.
2012/0330228 A1 12/2012 Day et al.
2013/0041343 A1 2/2013 Toumazou et al.
2013/0085679 A1 4/2013 Budiman
2013/0190583 A1 7/2013 Grosman et al.
2013/0231543 A1 9/2013 Facchinetti et al.
2013/0231642 A1 9/2013 Doyle, III et al.
2013/0245547 A1 9/2013 El-Khatib et al.
2013/0274576 A1 10/2013 Amirouche et al.
2013/0277287 A1 10/2013 Moissl et al.
2013/0345663 A1 12/2013 Agrawal et al.
2013/0345664 A1 12/2013 Beck et al.
2014/0005633 A1 1/2014 Finan
2014/0051957 A1 2/2014 Say et al.
2014/0066886 A1 3/2014 Roy et al.
2014/0066887 A1 3/2014 Mastrototaro et al.
2014/0066890 A1 3/2014 Sloan et al.
2014/0081236 A1 3/2014 Wilinska et al.
2014/0088393 A1 3/2014 Bernstein et al.
2014/0107607 A1 4/2014 Estes
2014/0121488 A1 5/2014 Budiman
2014/0163517 A1 6/2014 Finan et al.
2014/0180203 A1 6/2014 Budiman et al.
2014/0180240 A1 6/2014 Finan et al.
2014/0200559 A1 7/2014 Doyle, III et al.
2014/0221966 A1 8/2014 Buckingham et al.
2014/0235981 A1 8/2014 Hayter
2014/0276554 A1 9/2014 Finan et al.

(56) References Cited

U.S. PATENT DOCUMENTS

| | | | |
|---|---|---|---|
| 2014/0303552 | A1 | 10/2014 | Kanderian, Jr. et al. |
| 2014/0309511 | A1 | 10/2014 | Stål |
| 2014/0309615 | A1 | 10/2014 | Mazlish |
| 2014/0323961 | A1 | 10/2014 | Blomquist et al. |
| 2014/0324020 | A1 | 10/2014 | Stefansen |
| 2014/0344289 | A1 | 11/2014 | Wei et al. |
| 2014/0371515 | A1 | 12/2014 | John |
| 2014/0371682 | A1 | 12/2014 | Bengtsson et al. |
| 2015/0018633 | A1 | 1/2015 | Kovachev et al. |
| 2015/0025495 | A1 | 1/2015 | Peyser |
| 2015/0045641 | A1 | 2/2015 | Rule |
| 2015/0057606 | A1 | 2/2015 | Taub et al. |
| 2015/0080756 | A1 | 3/2015 | Robinson et al. |
| 2015/0100038 | A1 | 4/2015 | McCann et al. |
| 2015/0157273 | A1 | 6/2015 | An et al. |
| 2015/0157793 | A1 | 6/2015 | Kovelman |
| 2015/0157794 | A1 | 6/2015 | Roy et al. |
| 2015/0157795 | A1 | 6/2015 | Valk et al. |
| 2015/0164414 | A1 | 6/2015 | Matthews |
| 2015/0165119 | A1 | 6/2015 | Palerm et al. |
| 2015/0190098 | A1 | 7/2015 | Patek et al. |
| 2015/0220702 | A1 | 8/2015 | Hovorka |
| 2015/0282744 | A1 | 10/2015 | Roy et al. |
| 2015/0289821 | A1 | 10/2015 | Rack-Gomer et al. |
| 2015/0306312 | A1 | 10/2015 | Palerm |
| 2015/0306314 | A1 | 10/2015 | Doyle, III et al. |
| 2015/0328403 | A1 | 11/2015 | Dobbles et al. |
| 2015/0331418 | A1 | 11/2015 | Nogueira et al. |
| 2015/0331419 | A1 | 11/2015 | Nogueira et al. |
| 2015/0352282 | A1 | 12/2015 | Mazlish |
| 2016/0007890 | A1 | 1/2016 | Kovatchev et al. |
| 2016/0022180 | A1 | 1/2016 | Joseph et al. |
| 2016/0029966 | A1 | 2/2016 | Salas-Boni et al. |
| 2016/0038673 | A1 | 2/2016 | Morales |
| 2016/0073964 | A1 | 3/2016 | Cobelli et al. |
| 2016/0074582 | A1 | 3/2016 | Becker |
| 2016/0113558 | A1 | 4/2016 | Bhavaraju et al. |
| 2016/0162662 | A1 | 6/2016 | Monirabbasi et al. |
| 2016/0162797 | A1 | 6/2016 | Thorpe et al. |
| 2016/0174911 | A1 | 6/2016 | Palerm et al. |
| 2016/0175520 | A1 | 6/2016 | Palerm et al. |
| 2016/0193409 | A1 | 7/2016 | Facchinetti et al. |
| 2016/0256087 | A1 | 9/2016 | Doyle, III et al. |
| 2016/0256629 | A1 | 9/2016 | Grosman et al. |
| 2016/0287184 | A1 | 10/2016 | Diebold et al. |
| 2016/0317743 | A1 | 11/2016 | Estes |
| 2016/0331310 | A1 | 11/2016 | Kovatchev |
| 2016/0331898 | A1 | 11/2016 | Damiano et al. |
| 2016/0354543 | A1 | 12/2016 | Cinar et al. |
| 2017/0021100 | A1 | 1/2017 | Starkweather et al. |
| 2017/0035969 | A1 | 2/2017 | Sloan et al. |
| 2017/0049383 | A1 | 2/2017 | McMahon et al. |
| 2017/0049386 | A1 | 2/2017 | Abraham et al. |
| 2017/0053072 | A1 | 2/2017 | Agrawal et al. |
| 2017/0053084 | A1 | 2/2017 | McMahon et al. |
| 2017/0053552 | A1 | 2/2017 | Zhong et al. |
| 2017/0065212 | A1 | 3/2017 | Gottlieb et al. |
| 2017/0080152 | A1 | 3/2017 | Wilinska et al. |
| 2017/0091419 | A1 | 3/2017 | Hoglund et al. |
| 2017/0119968 | A1 | 5/2017 | Keenan et al. |
| 2017/0135643 | A1 | 5/2017 | Budiman et al. |
| 2017/0143899 | A1 | 5/2017 | Gondhalekar et al. |
| 2017/0143901 | A1 | 5/2017 | Tubb |
| 2017/0147781 | A1 | 5/2017 | Gondhalekar et al. |
| 2017/0165416 | A1 | 6/2017 | Saint |
| 2017/0203036 | A1 | 7/2017 | Mazlish et al. |
| 2017/0203038 | A1 | 7/2017 | Desborough et al. |
| 2017/0213009 | A1 | 7/2017 | Tubb |
| 2017/0232195 | A1 | 8/2017 | Desborough et al. |
| 2017/0258992 | A1 | 9/2017 | Zhou |
| 2017/0273607 | A1 | 9/2017 | Facchinetti et al. |
| 2017/0274144 | A1 | 9/2017 | Hayter |
| 2017/0281867 | A1 | 10/2017 | Parikh et al. |
| 2017/0325736 | A1 | 11/2017 | Cantwell et al. |
| 2017/0332952 | A1 | 11/2017 | Desborough et al. |
| 2017/0337348 | A1 | 11/2017 | Kovatchev et al. |
| 2017/0348482 | A1 | 12/2017 | Duke et al. |
| 2017/0348483 | A1 | 12/2017 | Duke et al. |
| 2017/0348484 | A1 | 12/2017 | Duke et al. |
| 2018/0043094 | A1 | 2/2018 | Day et al. |
| 2018/0043095 | A1 | 2/2018 | Finan et al. |
| 2018/0055452 | A1 | 3/2018 | Breton |
| 2018/0085523 | A1 | 3/2018 | Mastrototaro et al. |
| 2018/0085524 | A1 | 3/2018 | Mastrototaro et al. |
| 2018/0093039 | A1 | 4/2018 | Estes |
| 2018/0099092 | A1 | 4/2018 | Roy |
| 2018/0126073 | A1 | 5/2018 | Wu et al. |
| 2018/0130551 | A1 | 5/2018 | Gass et al. |
| 2018/0147349 | A1 | 5/2018 | Finan et al. |
| 2018/0154076 | A1 | 6/2018 | Budiman |
| 2018/0169322 | A1 | 6/2018 | Chiu et al. |
| 2018/0169332 | A1 | 6/2018 | Sadeghzadeh et al. |
| 2018/0169333 | A1 | 6/2018 | Grosman et al. |
| 2018/0169334 | A1 | 6/2018 | Grosman et al. |
| 2018/0174675 | A1 | 6/2018 | Roy et al. |
| 2018/0200434 | A1 | 7/2018 | Mazlish et al. |
| 2018/0200435 | A1 | 7/2018 | Mazlish et al. |
| 2018/0200439 | A1 | 7/2018 | Mazlish et al. |
| 2018/0200440 | A1 | 7/2018 | Mazlish et al. |
| 2018/0200441 | A1 | 7/2018 | Mazlish et al. |
| 2018/0233221 | A1 | 8/2018 | Blomquist |
| 2018/0235524 | A1 | 8/2018 | Dunn et al. |
| 2018/0271455 | A1 | 9/2018 | Zhong et al. |
| 2018/0272063 | A1 | 9/2018 | Neemuchwala et al. |
| 2018/0272064 | A1 | 9/2018 | McMahon et al. |
| 2018/0272065 | A1 | 9/2018 | Talbot et al. |
| 2018/0272066 | A1 | 9/2018 | McMahon et al. |
| 2018/0277242 | A1 | 9/2018 | Zhong et al. |
| 2018/0277246 | A1 | 9/2018 | Zhong et al. |
| 2018/0289891 | A1 | 10/2018 | Finan et al. |
| 2018/0296757 | A1 | 10/2018 | Finan et al. |
| 2018/0296758 | A1 | 10/2018 | Hayter |
| 2019/0054237 | A1 | 2/2019 | Budiman et al. |
| 2019/0151540 | A1 | 5/2019 | Wilinska et al. |
| 2019/0019277 | A1 | 6/2019 | Vinas et al. |

FOREIGN PATENT DOCUMENTS

| | | | |
|---|---|---|---|
| JP | 2016167152 | | 9/2016 |
| WO | 2004023972 | | 3/2004 |
| WO | WO2007116226 | A2 | 10/2007 |
| WO | 2013/067022 | | 5/2013 |
| WO | WO2016061308 | A1 | 4/2016 |
| WO | 2017027459 | | 2/2017 |
| WO | WO2017123805 | A1 | 7/2017 |
| WO | WO2017124006 | A1 | 7/2017 |

OTHER PUBLICATIONS

Haidar, A. (2016). The Artificial Pancreas: How closed-loop control is revolutionizing diabetes. *IEEE Control Systems Magazine*, 36(5), pp. 28-47.

International Search Report of the International Searching Authority pertaining to International Application No. PCT/US2018/030771; dated Jul. 31, 2018.

Written Opinion of the International Searching Authority pertaining to International Application No. PCT/US2018/030771; dated Jul. 31, 2018.

Bleris, L. G., & Kothare, M. V. (Dec. 2005) "Implementation of Model Predictive Control for Glucose Regulation on a General Purpose Microprocessor," Proceedings of the 44th IEEE Conference on Decision and Control and the European Control Conference 2005, Seville, Spain, Dec. 12-15, 2005, pp. 5162-5167.

Mendonça, T., Lemos, J. M., Magalhaes, H., Rocha, P., & Esteves, S. (2009), "Drug Delivery for Neuromuscular Blockade With Supervised Multimodel Adaptive Control," IEEE Transactions on Control Systems Technology, 17(6), pp. 1237-1244.

Grossman, B., Dassau, E., Zisser, H., Jovanovic, L., & Doyle III, F. (2010), "Zone Model Predictive Control: A Strategy to Minimize Hyper- and Hypoglycemic Events," Journal of Science and Technology, vol. 4, Issue 4, pp. 961-975.

(56) References Cited

OTHER PUBLICATIONS

Fischer, U., Schenk, W., Salzsieder, E., Albrecht, G., Abel, P. & Freyse, E.-J. (Aug. 1987), "Does Physiological Blood Glucose Control Require an Adaptive Control Strategy?" IEEE Transactions on Biomedical Engineering, vol. BME-34, No. 8, pp. 575-582.
Rabasa-Lhoret, R., Bourque, J., Ducros, F., Chiasson, J. (Apr. 2001), "Guidelines for Premeal Insulin Dose Reduction for Post-prandial Exercise of Different Intensities and Durations in Type 1 Diabetic Subjects Treated Intensively With a Basal-Bolus Insulin Regimen (Ultralente-Lispro), Pathophysiology/Complications," Diabetes Care, vol. 24, No. 4, pp. 625-630.
Magni, L., Raimondo, D. M., Bossi, L., Dalla Man, C., De Nicolao, G., Kovatchev, B., & Cobelli, C. (2007), "Model Predictive Control of Type 1 Diabetes: An In Silico Trial," J Diabetes Sci Technol, vol. 1, Issue 6, Nov. 2007, pp. 804-812.
Clarke, W. L., Anderson, S., Breton, M., Patek, S., Kashmer, L., & Kovatchev, B. (2009), "Closed-Loop Artificial Pancreas Using Subcutaneous Glucose Sensing and Insulin Delivery and a Model Predictive Control Algorithm: The Virginia Experience," J Diabetes Sci Technol, vol. 3, Issue 5, Sep. 2009, pp. 1031-1038.
Cobelli, C., Dalla Man, C., Sparacino, G., Magni, L., De Nicolao, G., & Kovatchev, B. P. (2009), "Diabetes: Models, Signals, and Control," IEEE Reviews in Biomedical Engineering, vol. 2, pp. 54-96.
Kovatchev, B., Patek, S., Dassau, E., Doyle III, F. J., Magni, L., De Nicolao, & G., Cobelli, C., Juvenile Diabetes Research Foundation Artificial Pancreas Consortium, (2009), "Control to Range for Diabetes: Functionality and Modular Architecture," J Diabetes Sci Technol, vol. 3, Issue 5, Sep. 2009, pp. 1058-1065.
Lee, H., & Bequette, B. W. (2009), "A Closed-Loop Artificial Pancreas Based on Model Predictive Control: Human-Friendly Identification and Automatic Meal Disturbance Rejection," Bio-medical Signal Processing and Control, 4(4), pp. 347-354.
Cobelli, C., Renard, E., & Kovatchev, B. (2011), "Artificial Pancreas: Past, Present, Future," Diabetes, 60(11), pp. 2672-2682.
Grosman, B., Dassau, E., Zisser, H., Jovanovič, L., & Doyle III, F. J. (2011), "Multi-zone-MPC: Clinical Inspired Control Algorithm for the Artificial Pancreas," IFAC Proceedings Volumes, 44(1), pp. 7120-7125.
Hughes, C. S., Patek, S. D., Breton, M., & Kovatchev, B. P. (2011), "Anticipating the Next Meal Using Meal Behavioral Profiles: A Hybrid Model-Based Stochastic Predictive Control Algorithm for T1DM," Computer Methods and Programs in Biomedicine, 102(2), pp. 138-148.
Toffanin, C., Messori, M., Di Palma, F., De Nicolao, G., Cobelli, C., & Magni, L. (2013), "Artificial Pancreas: Model Predictive Control Design From Clinical Experience," J. Diabetes Sci Technol, vol. 7, Issue 6, Nov. 2013, pp. 1470-1483.
Trevitt, S., Simpson, S., & Wood, A. (2015), "Artificial Pancreas Device Systems for the Closed-Loop Control of Type 1 Diabetes: What Systems are in Development?" Journal of Diabetes Science and Technology, 10(3), pp. 714-723.
King, A. (2012), "Continuous Glucose Monitoring-Guided Insulin Dosing in Pump-Treated Patients With Type 1 Diabetes: A Clinical Guide," Journal of Diabetes Science and Technology, 6(1), pp. 191-203.
Bolderman, K. et al. (2013), Chapter 5, Pump Start-Up, Putting Your Patients on the Pump, American Diabetes Association, pp. 90-148.
Chase, H. P. et al. (2002), "Post-Prandial Glucose Excursions Following Four Methods of Bolus Insulin Administration in Subjects With Type 1 Diabetes," Diabetes UK, Diabetes Medicine, 19, pp. 317-321.
Swan, K. L., Dziura, J. D., Steil, G. M., Voskanyan, G. R., Sikes, K. A., Steffen, A. T., Martin, M. L., Tambolane, W. V., Weinzimer, S. A., "Effect of Age of Infusion Site and Type of Rapid-Acting Analog on Pharmaco-Dynamic Parameters of Insulin Boluses in Youth With Type 1 Diabetes Receiving Insulin Pump Therapy," Diabetes Care 2009, 32(2), pp. 240-244.
Vaughn, D. E., Muchmore, D. B., "Use of Recombinant Human Hyaluronidase to Accelerate Rapid Insulin Analogue Absorption: Experience With Subcutaneous Injection and Continuous Infusion," Endocr Pract, 2011, vol. 17, No. 6, pp. 914-921.
Karlin, A. W., Ly, T. T., Pyle, L., Forlenza, G. P., Messer, L., Wadwa, R. P., DeSalvo, D.J., Payne, S.L., Hanes, S., Clinton, P., Maahs, D. M., Buckingham, B., "Duration of Infusion Set Survival in Lipohypertrophy Versus Nonlipohypertrophied Tissue in Patients With Type 1 Diabetes," Diabetes Tech. Therapeutics 2016, vol. 18, No. 7, pp. 429-435.
Patel, P. J., Benasi, K., Ferrari, G., Evans, M.G., Shanmugham, S., Wilson, D. M., Buckingham, B. A., "Randomized Trial of Infusion Set Function: Steel Versus Teflon," Diabetes Tech. Therapeutics 2014, vol. 16, No. 1, pp. 15-19.
Cescon, M., DeSalvo, D. J., Ly, T. T., Maahs, D. M., Messer, L. H., Buckingham, B. A., Doyle III, F. J., Dassau, E., "Early Detection of Infusion Set Failure During Insulin Pump Therapy in Type 1 Diabetes," J. Diabetes Sci. Tech. 2016, vol. 10 (6), pp. 1268-1276.
Bayard, D.S., Jelliffe, R.W., "A Baeysian Approach to Tracking Patients Having Changing Pharmacokinetic Parameters," J. Parmacokinetics and Pharmacodynamics, 2004, 31 (1), pp. 75-107.
C. Levetan, L. L. Want, C. Weyer, S. A. Strombel, J. Crean, Y. Wang, et al., "Impact of Pramlintide on Glucose Fluctuations and Post-prandial Glucose, Glucagon, and Triglyceride Excursions Among Patients with Type 1 Diabetes Intensively Treated with Insulin Pumps," Diabetes Care, vol. 26, No. 1, pp. 1-8, Jan. 2003.
R. E. Ratner, R. Dickey, M. Fineman, D. G. Maggs, L. Shen, S. A. Strombel, et al., "Amylin Replacement With Pramlintide as an Adjunct to Insulin Therapy Improves Long-Term Glycaemic and Weight Control in Type 1 Diabetes Mellitus: A 1-Year, Randomized Controlled Trial," Diabetic Medicine, vol. 21, pp. 1204-1212, 2004.
D. M. Huffman, G. W. McLean, and M. A. Seagrove, "Continuous Subcutaneous Pramlintide Infusion Therapy in Patients With Type 1 Diabetes: Observations From a Pilot Study," Endocrine Practice, vol. 15, No. 7, pp. 689-695, Nov.-Dec. 2009.
S. A. Weinzimer, J. L. Sherr, E. Cengiz, G. Kim, J. L. Ruiz, L. R. Carria, et al., "Effect of Pramlintide on Prandial Glycemic Excursions During Closed-Loop Control in Adolescents and Young Adults With Type 1 Diabetes," Diabetes Care, vol. 35, pp. 1994-1999, Oct. 2012.
J. L. Sherr, N. S. Patel, C. I. Michaud, M. M. Palau-Collazo, M. A. Van Name, W. V. Tamborlane, et al., "Mitigating Meal-Related Glycemic Excursions in an Insulin-Sparing Manner During Closed-Loop Insulin Delivery: The Beneficial Effects of Adjunctive Pramlintide and Liraglutide," Diabetes Care, vol. 39, pp. 1127-1134, Jul. 2016.
R. A. Heptulla, L. M. Rodriguez, K. J. Mason, and M. W. Haymond, "Twenty-Four-Hour Simultaneous Subcutaneous Basal-Bolus Administration of Insulin and Amylin in Adolescents With Type 1 Diabetes Decreases Postprandial Hyperglycemia," J Clin Endocrinol Metab, vol. 94, No. 5, pp. 1608-1611, May 2009.
S. A. Weinzimer, G. M. Steil, K. L. Swan, J. Dziura, N. Kurtz, and W. V. Tamborlane, "Fully Automated Closed-Loop Insulin Delivery Versus Semiautomated Hybrid Control in Pediatric Patients With Type 1 Diabetes Using an Artificial Pancreas," Diabetes Care, vol. 31, No. 5, pp. 934-939, May 2008.
J. R. Castle, J. M. Engle, J. El Youssef, R. G. Massoud, K. C. Yuen, R. Kagan, et al., "Novel Use of Glucagon in a Closed-Loop System for Prevention of Hypoglycemia in Type 1 Diabetes," Diabetes Care, vol. 33, No. 6, pp. 1282-1287, Jun. 2010.
E. Atlas, R. Nimri, S. Miller, E. A. Grunberg, and M. Phillip, "MD-Logic Artificial Pancreas System: A Pilot Study in Adults With Type 1 Diabetes," Diabetes Care, vol. 33, No. 5, pp. 1072-1076, May 2010.
M. Breton, A. Farret, D. Bruttomesso, S. Anderson, L.Magni, S. Patek, et al., "Fully Integrated Artificial Pancreas in Type 1 Diabetes: Modular Closed-Loop Glucose Control Maintains Near Normoglycemia," Diabetes, vol. 61, pp. 2230-2237, Sep. 2012.
M. W. Percival, Y. Wang, B. Grosman, E. Dassau, H. Zisser, L. Jovanovic, et al., "Development of a Multi-Parametric Model Predictive Control Algorithm for Insulin Delivery in Tyle 1 Diabetes Mellitus Using Clinical Parameters," J Process Control, vol. 21, No. 3, pp. 391-404, Mar. 1, 2011.

(56) References Cited

OTHER PUBLICATIONS

F. H. El-Khatib, S. J. Russell, D. M. Nathan, R. G. Sutherlin, and E. R. Damiano, "A Bihormonal Closed-Loop Artificial Pancreas for Type 1 Diabetes," Sci Transl Med, vol. 2, No. 27, pp. 1-17, Apr. 14, 2010.

K. S. Narendra and J. Balakrishnan, "Adaptive Control Using Multiple Models," IEEE Transactions on Automatic Control, vol. 42, No. 2, pp. 171-187, Feb. 1997.

CLOSED LOOP CONTROL OF PHYSIOLOGICAL GLUCOSE

RELATED APPLICATIONS

This application is a National Stage of International Application No. PCT/US2018/030771, filed May 3, 2018, which claims priority to Provisional Application No. 62/501, 976, filed May 5, 2017, and Provisional Application No. 62/536,541, filed Jul. 25, 2017, the disclosures of which are herein incorporated by reference in their entirety.

FIELD OF THE DISCLOSURE

The present disclosure relates to the control of physiological glucose concentrations. More particularly, the present disclosure relates to closed loop systems and methods for controlling physiological glucose concentrations in a patient.

BACKGROUND

Subcutaneous insulin replacement therapy has proven to be the regimen of choice to control diabetes. Insulin is administered via either multiple daily injections or an infusion pump with dosages being informed by capillary glucose measurements made several times a day by a blood glucose meter. This conventional approach is known to be imperfect as day to day (and in fact moment to moment) variability can be significant. Further, this approach can be burdensome to the patient as it requires repeated finger sticks, a rigorous monitoring of food intake, and vigilant control of insulin delivery.

The advent of glucose measurement devices such as a continuous glucose monitor (CGM) creates the potential to develop a closed loop artificial pancreas (AP) system. An AP system uses glucose data provided by the CGM in a dosing/control algorithm executed on a controller that provides direction to an infusion pump, and the pump administers medication to the patient. Such a system has the potential to revolutionize diabetes care as it offers the possibility of better glycemic control. Additionally, such a system reduces the patient demand for vigilance and thus fosters improved quality of life.

Some existing control algorithms for artificial pancreas systems are either restricted to operating within a small range of variation (for non-adaptive controllers) or restricted to reacting slowly to abrupt changes in glucose dynamics. Some existing control algorithms generally do not include a model of insulin in a human body, while some include a model that is a single, fixed model or a slowly adapting model. These limited control algorithms may only adequately control glucose concentrations when glucose dynamics are either constant or slowly changing. Current AP systems lack a control method designed to specifically handle abrupt as well as slow variations in glucose dynamics.

SUMMARY

According to an illustrative embodiment of the present disclosure, a system to control glycemia in a patient is provided including a medication delivery device configured to deliver a medication dose to the patient and a user interface configured to generate user data based on at least one user input. The system further includes a controller in communication with the medication delivery device and the user interface. The controller includes control logic operative to receive a glucose signal at a pre-selected interval from a glucose measurement device. The glucose signal is representative of a level of glucose in the patient. The control logic is further operative to execute a multiple model predictive controller algorithm to determine a medication dose request and transmit the medication dose request to the medication delivery device.

BRIEF DESCRIPTION OF THE DRAWINGS

The above-mentioned and other features and advantages of this disclosure, and the manner of attaining them, will become more apparent and will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

System Hardware

The term "logic" or "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed.

The term "drug" or "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of transport or delivery by the infusion set. The drug as used in the drug delivery device may be formulated with one or more excipients. The drug delivery device is operated in a manner generally as described herein to deliver drug to a person.

Figure 1:
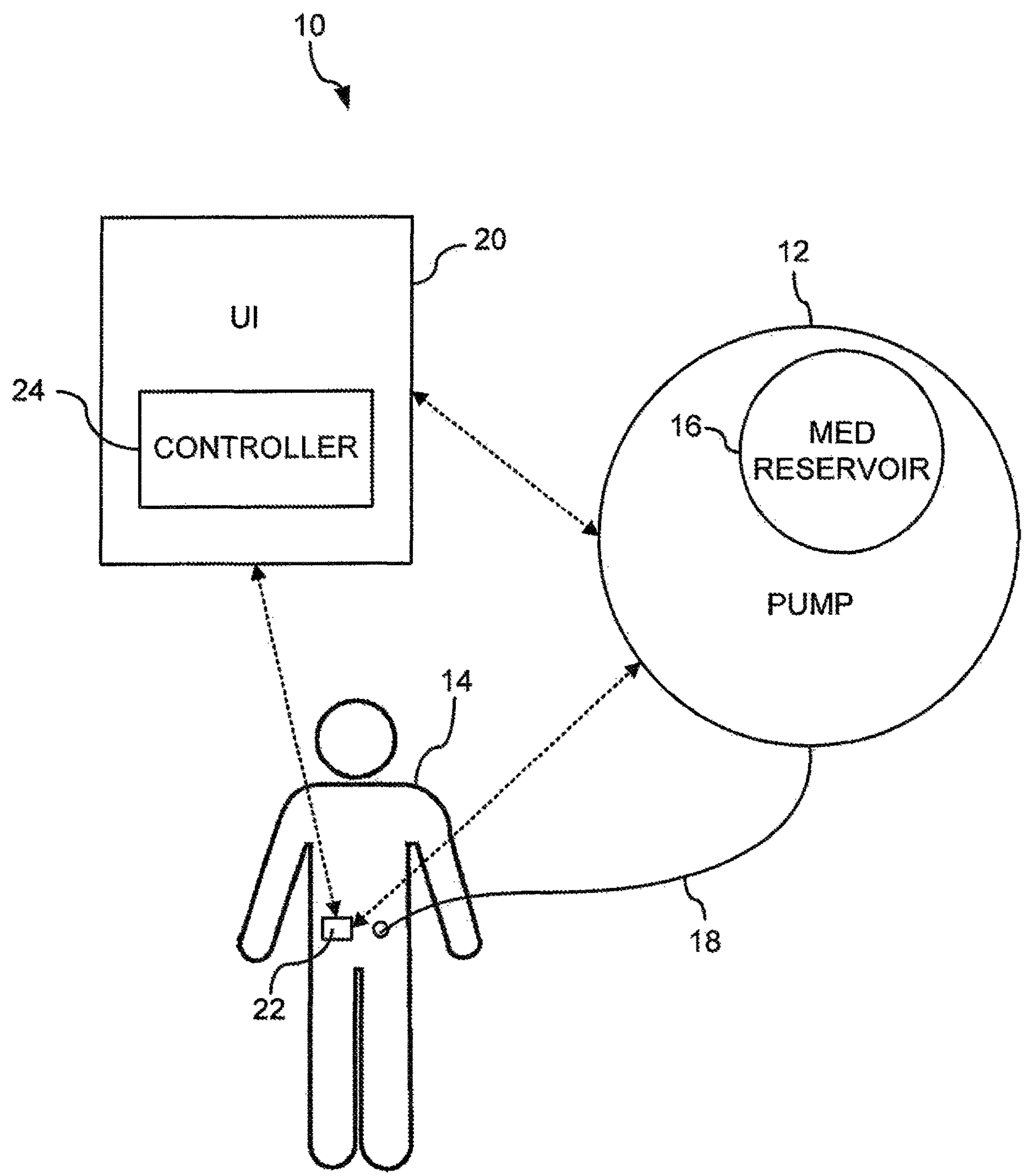
FIGS. 1, 1A, and 2 depict representational block diagrams of a system for controlling physiological glucose.
Figure 1A:
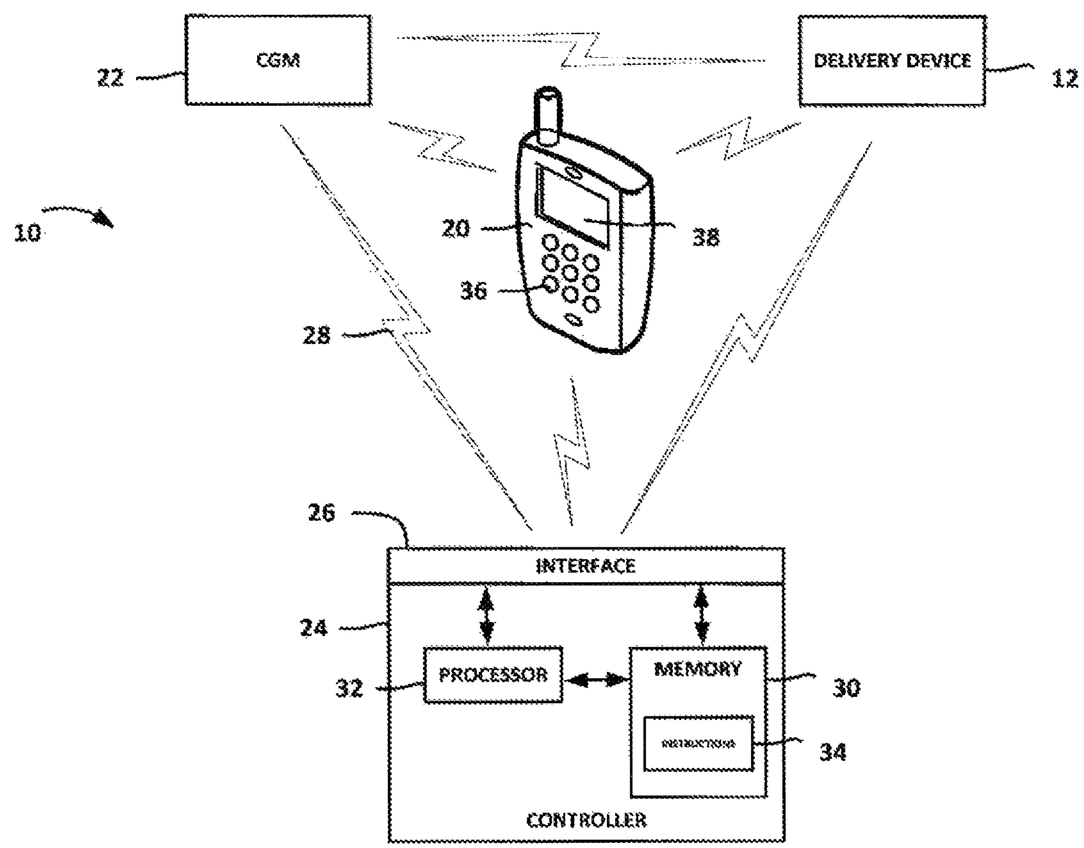
Figure 2:
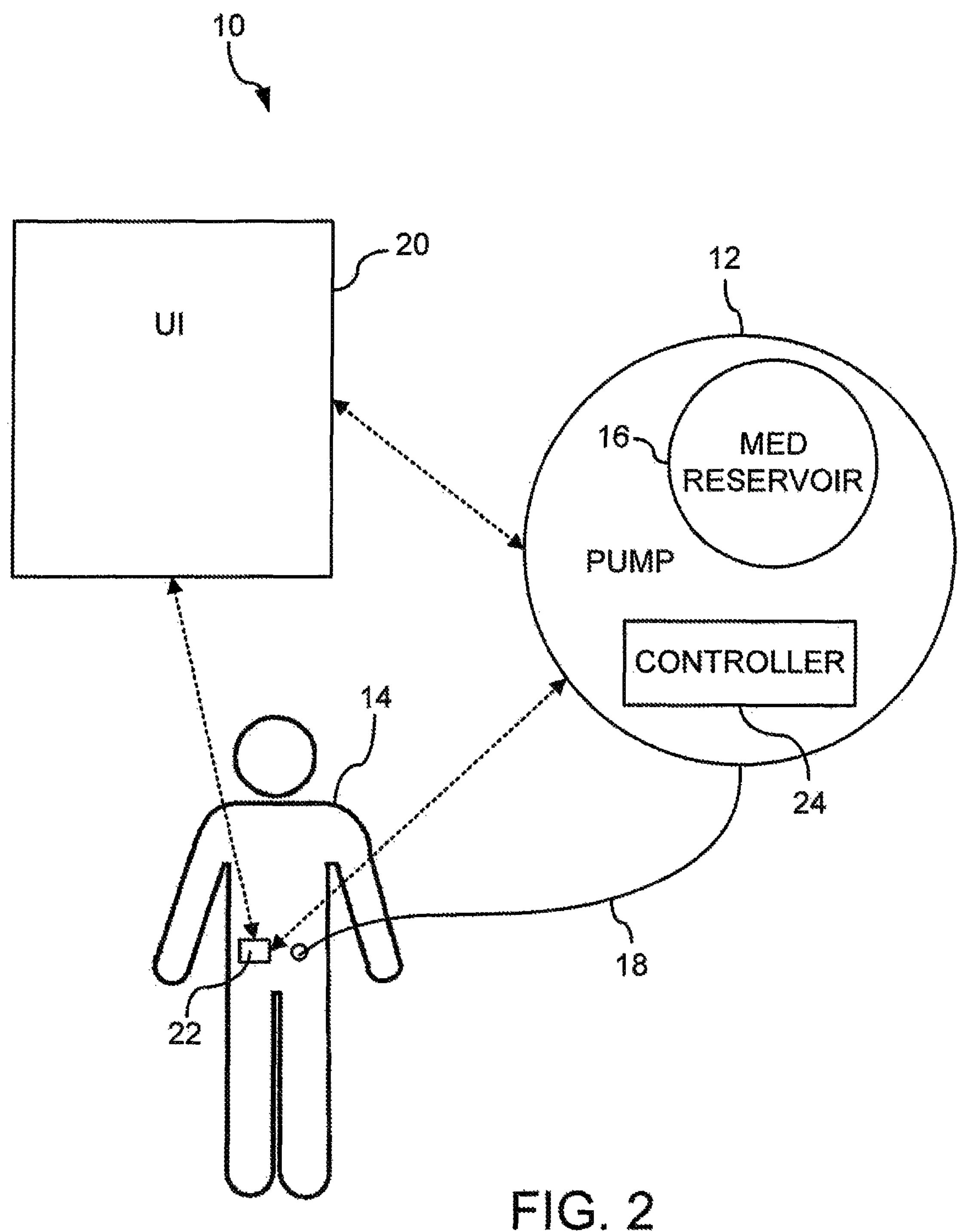

A system to provide closed-loop control of physiological glucose is disclosed herein. Exemplary hardware elements of the system include a sensor to measure the physiological glucose concentration in the body, a user interface to receive user data, a pump to deliver insulin, and an electronic controller including control logic operative to integrate the data, execute the algorithm, and control the pump. In addition, the various elements may communicate with each other. FIGS. 1, 1A, and 2 depict exemplary representational block diagrams of a system 10 for controlling physiological glucose. The system 10 comprises a drug delivery device 12, a user interface 20, a device to measure glucose 22, and an electronic controller 24.

The drug delivery device 12 is illustratively an infusion pump 12. An exemplary pump 12 includes an ambulatory infusion pump such as those described in U.S. patent application Ser. No. 13/788,280, to Lanigan et al., filed Mar. 7, 2013, and entitled "Infusion Pump Assembly". The pump 12 may include at least one medication reservoir 16 which contains a first medication. The first medication may be a hormone which is involved in the control of physiological glucose. In some specific embodiments, the first medication may be a hormone which lowers physiological glucose concentrations such as insulin. In other embodiments, the drug delivery device may be used in conjunction with an oral medication such as SGLT-1 or SGLT-2. Other embodiments may include an additional reservoir 16 for a second medication which may be a hormone which is antagonistic to the first medication. For example, the second medication, stored in an additional reservoir 16, may be a drug or hormone such as glucagon which raises physiological glucose concentrations. In another example, the second medication may be another suitable glucose management drug such as GLP-1, pramlintide, amylin, or another amylin analogue. Use of the word amylin herein shall be understood to mean amylin or any analogue thereof may be used. The medication delivery device 12 may deliver at least one medication to a patient 14 via an infusion set 18 providing a fluid path from the pump 12 to the patient 14. The infusion set 18 may, for example, provide a fluid path from the pump 12 to a subcutaneous destination within the patient 14. In some embodiments, the pump 12 provides a fluid path to the subcutaneous destination within the patient 14. The pump 12 or infusion set 18 may include a needle or cannula for inserting into the subcutaneous tissue of the patient.

The system 10 includes an analyte sensor such as a glucose measurement device 22. The glucose measurement device 22 may be a standalone device or may be an ambulatory device. One example of a glucose measurement device is a continuous glucose monitor (CGM) 22. In specific embodiments, the CGM 22 may be a glucose sensor such as a Dexcom G4 or G5 series continuous glucose monitor, although any suitable continuous glucose monitor may be used. The CGM 22 is illustratively worn by the patient 14 and includes one or more sensors in communication with or monitoring a physiological space (e.g., an interstitial or subcutaneous space) within the patient 14 and able to sense an analyte (e.g., glucose) concentration of the patient 14. In some embodiments, the CGM 22 reports a value that is associated with the concentration of glucose in the interstitial fluid, e.g., interstitial glucose (IG). The CGM 22 may transmit a signal representative of an IG value to the user interface 20, pump 12, controller 24, or another receiver.

The system 10 includes a user interface (UI) device 20 that may be used to input user data to the system 10, modify values, and receive information, prompts, data, etc., generated by the system 10. The UI 20 may include an input device such as a keyboard or keypad for providing alphanumeric data to the controller 24. The keyboard or keypad may include tactile indicators to facilitate use without good eyesight or backlit keys for use without lighting. The UI 20 may include buttons or switches to communicate with the device. In one example, the UI 20 has buttons or switches to announce events such as a meal, start of exercise, end of exercise, emergency stop, etc. In some embodiments, the UI is a graphical user interface (GUI) with a display, where the user interacts with presented information, menus, buttons, etc., to receive information from and provide information to the system 10. The UI 20 may include a pointer, roller ball, and buttons to interact with the UI 20. Additionally, the UI 20 may be implemented on a touch screen capable of displaying images and text and capable to detecting input via a touch. The UI 20 may be a dedicated device or may be implemented via an application or app running on a personal smart device such as a phone, tablet, etc. The UI 20 may be in communication with the pump 12 and the CGM 22. The pump 12 and CGM 22 may also be in communication with one another.

The controller 24 may be included in the drug delivery device 12 (see FIG. 2) or external to the pump 12, e.g., in the UI 20 (see FIG. 1). Alternatively, the UI 20 and the pump 12 may each include a controller 24 and control of the system 10 may be divided between the two controllers 24. The controller 24 can include at least one processor (e.g., microprocessor) that executes software and/or firmware stored in memory of the controller 24. The software/firmware code contains instructions that, when executed by the processor, cause the controller 24 to perform the functions of the control algorithm described herein. The controller 24 may alternatively include one or more application-specific integrated circuits (ASICs), field-programmable gate arrays (FPGAs), digital signal processors (DSPs), hardwired logic, or combinations thereof. The controller 24 may receive information from a plurality of system 10 components and feed the information (e.g., pump data, glucose data, drug delivery data, user data) into the control algorithm which determines at least one drug delivery control parameter which may in part govern operation of the pump 12. In some specific embodiments, the controller 24 may receive pump data from the pump 12, glucose data from the CGM 22, and user data from the UI 20. The pump data received may include drug delivery data corresponding to drug dosages delivered to the patient 14 by the pump 12. The pump data may be supplied by the pump 12 as doses are delivered or on a predetermined schedule. The glucose data received by the controller 24 may include glucose concentration data from the CGM 22. The glucose data may be supplied at a continuous rate, occasionally or at predefined intervals (e.g., every 5 or 10 minutes).

FIG. 1A shows an exemplary implementation of the system 10. Although the controller 24 is shown as being separate from the drug delivery device 12 and the UI 20, the controller 24 can be physically incorporated into either the drug delivery device 12 or the UI 20. Regardless of its physical location within the system 10, the controller 24 is shown as being directly or indirectly communicatively coupled to the drug delivery device 12, the UI 20, and the CGM 22. The controller 24 can include or be communicatively coupled to one or more interfaces 26 to communicatively couple via one or more communication links 28 to the drug delivery device 12, the UI 20, and the CGM 22. Example interfaces 26 include wired and wireless signal transmitters and receivers. Example communication links 28 include a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two devices. The communication links 28 may be a persistent communication link, an intermittent communication link, an ad-hoc communication link, and/or the like. Information (e.g., pump data, glucose data, drug delivery data, user data) may be transmitted via the communication links 28. The drug delivery device 12, the UI 20, and the CGM 22 may also include one or more interfaces to communicatively couple via one or more communication links 28 to the other devices in the system 10.

FIG. 1A shows the controller 24 including memory 30 and a processor 32 communicatively coupled to the one or more interfaces 26 and to each other. The memory 30 may include computer-readable storage media in the form of volatile and/or nonvolatile memory and may be removable, non-removable, or a combination thereof. In embodiments, the memory 30 stores executable instructions 34 (e.g., computer code, machine-useable instructions, and the like) for causing the processor 32 to implement aspects of embodiments of system components discussed herein and/or to perform aspects of embodiments of methods and procedures discussed herein, including the control logic described in more detail below. The memory 30, the processor 32, and the interfaces 26 may be communicatively coupled by one or more busses.

As described above, the UI 20 may be a dedicated device (e.g., handheld user device programmed specifically for the system 10) or may be implemented via an application or app running on a personal smart device such as a phone, tablet, etc. The UI 20 may include input devices 36 (e.g., buttons, switches) and a display 38 that displays the GUI. The user can interact with the input devices 36 and the display 38 to provide information to the system 10.

The pump data, glucose data, drug delivery data, and user data may be provided to the controller 24 as acquired, on a predefined schedule or queued in memory and supplied to the controller 24 when requested. The user data may be input to the UI 20 in response to user/patient prompts generated by the UI 20 and/or declared by the patient 14 as instructed during training. In some embodiments, at least some of the pump data, glucose data, and/or user data may be retrieved from a memory associated with the controller 24, and some of this data may be retrieved from a memory in the pump 12. In some embodiments, user interaction with the UI 20 may be minimal with the patient 14 being prompted to start execution of the algorithm implemented by the controller 24 and provide meal and/or exercise announcements. In other embodiments, the user may be prompted to provide various additional data in order to initialize the algorithm implemented by the controller 24.

The memory of the controller 24 is any suitable computer readable medium that is accessible by the processor. Memory may be a single storage device or multiple storage devices, may be located internally or externally to the controller 24, and may include both volatile and non-volatile media. Exemplary memory includes random-access memory (RAM), read-only memory (ROM), electrically erasable programmable ROM (EEPROM), flash memory, CD-ROM, Digital Versatile Disk (DVD) or other optical disk storage, a magnetic storage device, or any other suitable medium which is configured to store data and which is accessible by the controller 24.

User data may include but is not limited to insulin/carbohydrate ratio, meal size, carbohydrate ratio of meal, and exercise. User data may also include a group of data that herein is referred to as insulin need data. The insulin need data may include but is not limited to Total Daily Insulin Dose (TDD), Total Daily Basal Dose (TDB), a basal dose, and a basal profile. In the illustrative embodiment, the TDD is the sum of all the insulin delivered over a 24-hour period, and the TDB is the sum of all the basal insulin deliveries over the 24-hour period. In one embodiment, the TDB is approximately equal to the TDD minus the sum of meal boluses. In the illustrative embodiment, the basal dose is an open loop or nominal insulin dose needed by the user for a predefined period. In one example, the basal dose is the amount of insulin needed by the user for the duration of each period or interval between glucose measurements received by the controller from the CGM. In another example, the basal dose at time t is the basal profile at time t. In the illustrative embodiment, the basal profile is a predefined time-varying insulin flow rate over the course of 24 hours. In one example, the basal profile may be expressed as a list of insulin flow rates or a paired list of flow rates and times. In another example, the basal profile may be expressed as an equation. One or more of these user data values may be updated from the UI as needed. In some embodiments, the TDD and TDB are updated regularly by the controller, where the values are based on recorded amounts of total and basal insulin supplied to the user over one or more days. In some embodiments, TDD and/or TDB may be input by a clinician or user at the user interface or stored in a memory that is readable by the controller.

The at least one drug delivery parameter determined by the controller 24 may be a medication dose or doses, which may at least in part govern drug administration to the patient 14 via the pump 12. For insulin delivery, the drug delivery parameter may be used to compute a basal rate or micro-bolus dose, a meal bolus dose or a meal bolus dosage. In dual hormone systems, the data may inform delivery of either or both insulin and a second medication such as glucagon or amylin. In one embodiment, the drug delivery parameter provided to the pump 12 is a control signal requesting the pump to deliver a specific amount or volume of medication. In one embodiment, the drug delivery parameter is an analogue or digital signal that the pump 12 converts to an amount or volume of medication or a number of pump strokes. In some embodiments, the drug delivery parameter is a deviation from the basal insulin dose or current value of the basal insulin profile. The deviation may be an amount or volume of insulin or a percentage of the basal insulin dose. Thus, the system 10 may operate in a closed loop setting which requires minimal or no interaction from the patient 14 after initial start-up to effect glycemic control.

The term physiological glucose herein refers to the measured concentration of glucose in the body. In some embodiments, physiological glucose may be the concentration of glucose in the blood, which may also be referred to as blood glucose. In other embodiments, physiological glucose may be the concentration of the glucose in the blood plasma, which may be referred to as plasma glucose. The measured value of plasma glucose is typically 10 to 12% higher than blood glucose because the blood cells of the blood have been removed in the plasma glucose determination. The relationship between plasma glucose and blood glucose depends on the hematocrit and can vary from patient to patient and over time. The physiological glucose, abbreviated herein as PG, may be measured indirectly by measuring the glucose concentration in the interstitial fluid which is referred to as interstitial glucose and abbreviated IG.

In the illustrative embodiment, the system 10 may supply insulin to the body as a basal delivery or as a bolus delivery. The basal delivery is the continuous delivery of insulin at the basal rate needed by the patient to maintain the glucose level in the patient's blood at the desired level. The insulin delivery device 12 may provide the basal delivery in micro-boluses or basal doses followed by periods of zero flow that average out to the basal rate. In one example, insulin delivery device supplies a basal dose at a fixed interval and the basal dose is equal to the desired basal rate times the duration of the interval. Occasionally, the user may require a larger amount of insulin due to a change in activity such as eating a meal or other activities that affect the user's metabolism. This larger amount of insulin is herein referred to as a meal bolus. A meal bolus is a specific amount of insulin that is generally supplied over a short period of time. The nature of the insulin delivery device may require delivering the bolus as a continuous flow of insulin for a period or as a series of smaller, discrete insulin volumes supplied over a period. The meal-bolus facilitates maintenance the glucose level as the digestive system supplies a large amount of glucose to the blood stream.

MMPC Algorithm

The Multi-Model Predictive Controller (MMPC) includes control logic of the controller 24 executing an artificial pancreas algorithm that combines multiple state vectors and their models with a model predictive control algorithm. The MMPC adds improved adaptability to changes in the body and the environment to the model-predictive controller by propagating multiple state vectors and selecting the state vector and its model that best matches past data. The selected-state vector and its model are then used in a model-predictive controller to determine the next basal rate or basal dose of insulin to deliver to the patient in order to achieve the desired physiological glucose level. The use of the multiple state vectors and their models improves the responsiveness of the algorithm to changes in metabolism, digestion, activity or other changes.

The MMPC propagates each of the state vectors at each time interval using models, glucose data and covariance matrices with a Kalman filter. In some embodiments, the MMPC retains the previous values of each state vector for a period of time and as each state vector is propagated generating the most current value of each state vector, the oldest value of each state vector is overwritten. In some embodiments, only the most current value of each state vector is stored in memory. Each state vector is associated with a unique model and unique covariance matrices. The MMPC selects a best state vector and its model based on how well the state variable for interstitial glucose (IG) matches the measured values of IG over a period in the past. The MMPC then uses in the selected-state vector and its model in a model-predictive controller where the MMPC propagates the selected-state vector out to a prediction horizon generating a predicted set of physiological glucose values over time. The set of predicted glucose values at corresponding time is herein referred to as a predicted trajectory. The MMPC uses the physiological glucose trajectory and an objective function to determine an optimal insulin trajectory with one or more limits on the insulin values.

In some embodiments, the optimal insulin trajectory is a trajectory of deviations from the basal insulin or basal profile, herein referred to as the basal-deviation trajectory. In these embodiments, the amount of insulin delivered to the body is the predefined basal insulin plus the optimal-basal deviation determined from the insulin trajectory. In these embodiments, the models do not include basal insulin inputs or endogenous glucose production. Rather, the model and objective function consider the response of the body to meals and insulin levels above or below the predefined basal insulin rate.

A preliminary insulin rate, dose or optimal-basal deviation is taken from the value of the insulin trajectory for the first interval. The MMPC may limit this preliminary insulin rate, dose or optimal-basal deviation before passing the rate or dose request to the delivery device. In the embodiments where the optimal insulin trajectory is the deviation from the basal profile, the dose request is the sum of the limited-basal deviation plus basal profile. The limited insulin rate, limited dose, or limited-basal deviation is then fed back into the multiple state vectors in block 110A as an insulin input for the determination of the insulin rate or dose at the next interval. An example MMPC receives user data from the UI 20 and glucose concentration data from the CGM 22 and determines the amount of medication for the pump 12 to deliver to the patient 14.

Figure 3:
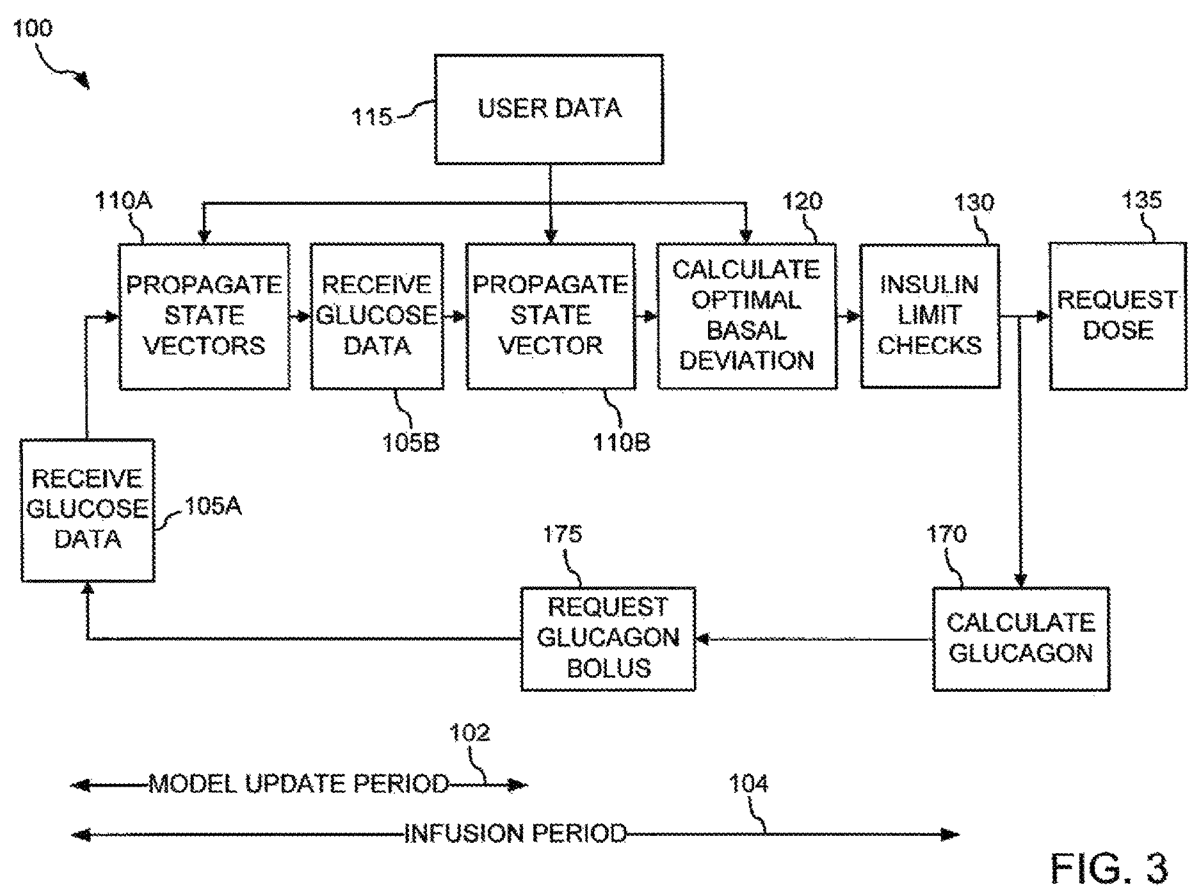
FIG. 3 depicts an example block diagram of an exemplary model predictive control algorithm configured for execution on an electronic controller of the system of FIGS. 1 and 2.
Figure 4:
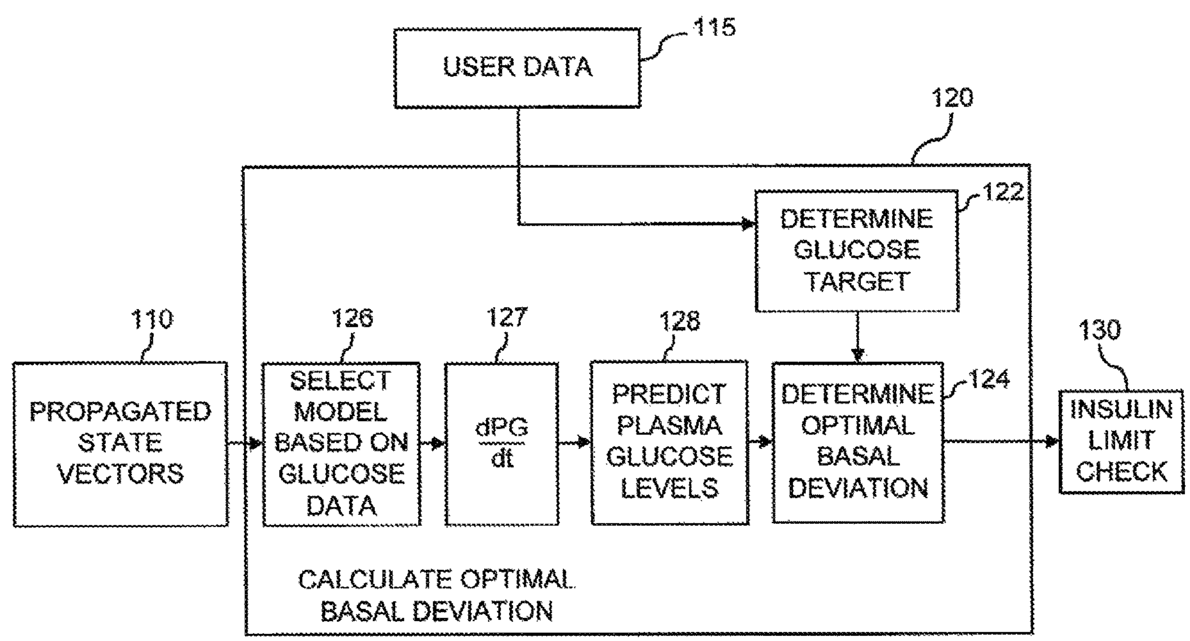
FIG. 4 depicts an example block diagram of calculating an optimal basal insulin deviation.

FIGS. 3, 4 depict representational block diagrams of an MMPC algorithm 100, which regularly receives IG data, uses one or more state-models to determine the optimal insulin dose and transmits a corresponding dose request to the insulin pump 12 before repeating the process. The MMPC algorithm 100 receives a measurement of the interstitial glucose (IG), in block 105A, from a continuous glucose monitor (CGM) placed on the patient's body or other glucose measurement device. In block 110A, the MMPC algorithm propagates each state vector which includes propagating each state vector using its associated model, filtering the state vector with a Kalman filter using IG data from block 105A, and adding meal carbohydrates and meal boluses to the state vector to produce updated state vectors.

In some embodiments, the MMPC algorithm 100 follows the steps of receiving glucose data 105A and propagating the state vector 110A by determining the optimal-basal deviation in block 120. In other embodiments, the steps of receiving glucose data and propagating the state vector are repeated in blocks 105B and 110B before calculating the optimal-basal deviation in block 120. The IG data or glucose data is received 105A, 105B and an updated state vector is calculated 110A, 110B at a regular interval equal to the Model Update Period ($\tau_{UPD}$) 102. The length of the update period may be equal to the period between outputs from the glucose sensor 22.

The injection period ($\tau_{INJ}$) includes at least one set of receiving glucose data and propagating the state vectors before determining the optimal-basal deviation 120, checking the insulin limits 130 and requesting a dose 135. In embodiments where the state vector is propagated 120 once per injection period, the injection period is equal to the update period. In embodiments, where the glucose data is received twice per injection period (e.g., blocks 105A and 105B), the steps of receiving glucose data and propagating the state vectors are repeated and the injection period is equal to twice the update period. In some embodiments, the injection time is fixed and the update time may vary based on the output of CGM 22, so that the state vector may be propagated more than once between insulin deliveries or injections, if the time between receiving glucose data is shorter than the injection time. In some embodiments, if the glucose data from the glucose sensor 22 is not available or the glucose data is unreliable, the state vector will be propagated 110 without the Kalman filter step before proceeding to the determination of the optimal-basal deviation in block 120.

Block 120 determines an optimal deviation from the basal profile to control the physiological glucose of the patient, and block 135 requests the pump 12 to deliver a new insulin basal rate or dose to the patient based on the optimal deviation and the basal profile. In block 120, the MMPC algorithm 100 selects the state vector and model that has the determined best record of estimating the glucose data over a given period of time in the past. Further, in block 120, the MMPC algorithm 100 uses the selected-state vector and model in a model-predictive algorithm to determine the next optimal-basal deviation. The determination of the next optimal-basal deviation may include user data from block 115. The optimal deviation from the basal profile may be passed to block 130, where the optimal deviation may be limited by one or more rules, i.e., the value of the deviation is changed to the value of an insulin threshold, if the optimal-basal deviation exceeds that insulin threshold. The insulin thresholds or limits in block 130 may be predefined values or predetermined functions of the physiological glucose estimated by the selected-state vector. The limited-basal deviation of block 130 is then passed to block 135, where insulin dose request is determined from the sum of the limited-basal deviation and the basal profile. At block 135, the MMPC algorithm 100 transmits the insulin dose request to the pump 12 and passes the insulin dose value to block 110A for inclusion in the propagation of the next state vector. The pump 12 delivers the requested insulin dose to the patient via the infusion set 18.

FIG. 4 further illustrates an exemplary block 120 of determining the optimal-basal deviation. In block 126, the propagated state vectors and corresponding state vectors are evaluated to identify the state vector and model that best matches measured IG data over a preceding time period. In some embodiments, the measured IG data is compared to the corresponding IG values of the state vector over a fixed historical period to determine the best match between the state vector and the glucose data. In some embodiments, best match between the state vector and glucose data is based on the sum of the squared differences between the measured IG data and corresponding IG values of the state vector. In this embodiment, the squared differences are summed over time with an exponentially decaying weight. Herein corresponding estimates of IG refers to the IG value in the state vector at the time of the IG data.

In some embodiments, an identification error is calculated for each state vector at each update interval ($\tau_{UPD}$) when glucose data is received. The identification errors at each update interval are stored for each state vector. In block 126, all the identification errors of each state vector are weighted and summed over a historical period to determine a performance index for each state vector. The state vector with the lowest performance index may be selected along with at least its model for the next steps 127-124 of a model-predictive control algorithm.

In block 127, the MMPC algorithm 100 determines the current derivative of the physiological glucose with respect to time (dPG/dt). The rate of change of the physiological glucose is used in some embodiments of the MMPC algorithm 100 to set limits on insulin deliveries, determine meal boluses, determine glucagon boluses, etc. The rate of change of the physiological glucose (dPG/dt) may be determined by several methods. In some embodiments, dPG/dt is based on the most recent several (e.g., three) estimates of physiological glucose ($PG_{j-2}$, $PG_{j-1}$, $PG_j$), where a quadratic equation is fit to the three estimates and dPG/dt is set equal to the slope of the equation at j. The three most recent estimates of physiological glucose concentration may be from different state vectors depending on which state vector model was selected. In some embodiments dPG/dt is the slope of a straight-line fit to the most recent physiological glucose values ($PG_j$, $PG_{j-1}$, $PG_{j-2}$, . . . $PG_{j-n}$). In some embodiments, the dPG/dt is the difference between $PG_{J-1}$ and $PG_J$, which is a slope as the time difference between successive values of $PG_J$ are constant. In some embodiments dPG/dt is difference between successive values ($PG_{j-1}-PG_j$) divided by the time interval ($\tau_{UPD}$).

In block 128, the selected-state vector and its model are used to predict the PG levels from the current time out to the prediction horizon ($PG_{j+1}$, $PG_{j+2}$, $PG_{j+3}$, . . . $PG_{j+m}$). The period of time from current time to the prediction horizon is herein referred to as the prediction period. The prediction period may be one or more hours. In some embodiments, the prediction time is four and half hours. The predictions of future PG values are made by propagating the state vector with its model without a Kalman filter and without corrections for meals. The values of PG are predicted assuming a basal insulin dose, no insulin meal boluses and no food. In this example, the Kalman filter is not used as the future glucose data is unknown.

In block 122, the physiological glucose target ($PG_{TGT}$) is a predetermined physiological glucose concentration with corrections for meals, exercise, the measured interstitial glucose concentration and/or the physiological glucose concentration of the selected-state vector. An exemplary predetermined physiological glucose concentration is 6 milli-Mole/liter (mmol/L) although other suitable targets may be used. In certain embodiments, the physiological glucose target varies over time. For example, the physiological glucose target may gradually increase or decrease to a predetermined constant physiological glucose target.

In block 124, the optimal-basal deviation is determined for the future period from the current time to the prediction horizon. In some embodiments, the optimal basal deviation is the optimal insulin trajectory relative to the basal profile. In other embodiments, the optimal basal deviation is simply the optimal insulin trajectory. The optimal basal deviation or optimal insulin trajectory is the trajectory that minimizes one or more objective functions with one or more limits on possible insulin or deviation values. In some embodiments, the objective function sums difference between the predicted physiological glucose values and the target glucose values over the future period. In some embodiments, the objective function may also sum the basal deviations or the insulin doses over the future period. In some embodiments, the summed values may be weighted differently based on time from a meal. The cost functions and the weighting depend on one or more of the following values including, but not limited to time since meal, meal size, and exercise level. The basal insulin or insulin trajectory for the first injection period 104 may be passed as a rate or an amount to block 130, where the rate or amount may be limited based on the estimated physiological glucose, rate of change of physiological glucose and/or the past insulin deliveries by the pump 12.

The Model

A model includes a set of linear difference equations executed by control logic that calculate levels of physiological or serum glucose (PG) and the interstitial glucose (IG) in a patient's body. In some embodiments, the model comprises eight compartments that track the movement and the persistence of insulin, carbohydrates, and glucose within the body. In some embodiments, the model considers external sources of glucose (carbohydrates) and levels of insulin different from the basal profile. In these embodiments, the output of the model in the optimization step of block 124 is an optimal basal deviation ($\delta_I$) from the basal insulin profile. The MMPC algorithm 100 adds the basal insulin profile value to the insulin deviation in block 135 before requesting the insulin dose from the pump 12.

The movement and persistence of insulin, carbohydrates, and glucose may be driven by several model parameters. The calculated PG values may be used to determine the next micro-bolus of insulin, a bolus of glucagon, and/or a meal bolus that may be delivered to the patient. The calculated IG may be compared to the measured IG. The MMPC algorithm 100 may comprise a large set of state vectors that each have a model with a unique combination of model parameters.

The model parameters may include but are not limited to insulin sensitivity ($S_I$), insulin time constant ($k_I$), the meal action time constant ($k_C$), sensor time constant ($k_{SENSOR}$), insulin to carbohydrate ratio (ICR). In some embodiments, the insulin sensitivity ($S_I$) is a function of the estimated basal insulin need, $S_I=S_P/(I_{EBN}/60)$, where $S_P$ is a model parameter that controls in part, at least, the effect of insulin on physiological glucose. The estimated basal need of insulin ($I_{EBN}$) is a function of the TDD and TDB. The absorption time constant ($k_I$) is a model parameter that controls at least the rate of transport from the insulin compartments in the model. In some embodiments, the absorption time constants ($k_I$) comprise values ranging between about 30 minutes and 90 minutes. The meal action time constant ($k_C$) is a model parameter that affects at least the transport rate of carbohydrates between compartments in the model. In some embodiments, the values of the meal action time constant may range from about 30 minutes to 90 minutes. The sensor time constant (ksensor) is a model parameter that in part affects the rate of transport of glucose between the physiological compartment and the interstitial compartment. The sensor time constant may also affect the relationship between the interstitial and the physiological glucose. The insulin to carbohydrate ratio (ICR) reflects the amount of insulin required to remove a given amount of glucose from the blood. The insulin to carbohydrate value may vary from meal to meal, i.e., may have a first value for breakfast, a second value for lunch, and a third value for dinner. The model parameters may include input values at the UI 20, programmed values in the algorithm, or stored values in the memory readable by the controller, or a combination of these options.

Figure 5:
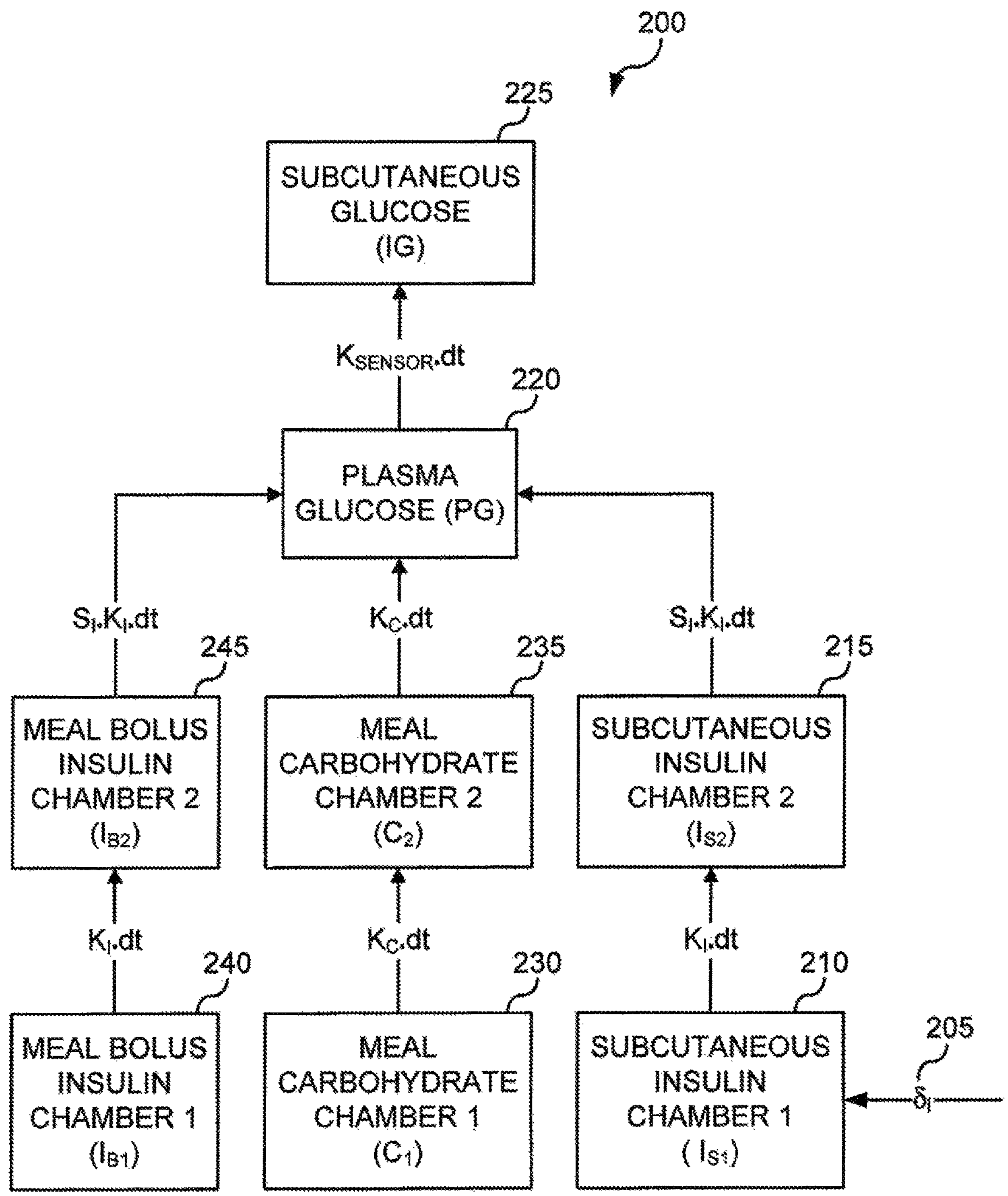
FIG. 5 depicts a block diagram of an exemplary compartmental model.

An exemplary model 200 may be represented as eight compartments that interact with each other as shown in FIG. 5. Storage and movement of insulin in the body from the subcutaneous infusion site to the blood stream may be modeled as two subcutaneous compartments 210, 215 that are connected to the blood compartment 220. Insulin micro-boluses may be added to the first subcutaneous chamber or compartment 210 and then transported to the second subcutaneous chamber or compartment 215, before being transported to the blood chamber or compartment 220. The modeled transport of insulin between compartments may be controlled in part by the insulin time constant ($k_I$) and the difference in insulin concentrations between the two compartments 210, 215.

Still referring to FIG. 5, the transport of carbohydrates through the stomach to the blood stream may be modeled as a first carbohydrate compartment 230 connected to a second carbohydrate compartment 235 which is connected to the blood compartment 220. The addition of carbohydrates to the first and second carbohydrate compartments is described herein. The modeled transport of carbohydrates between compartments 230, 235 may be controlled in part by the meal action time ($k_C$) and the difference in carbohydrate concentrations between the two compartments 230, 235.

Still referring to FIG. 5, the storage and movement of meal bolus insulin from the subcutaneous infusion site to the blood stream may be modeled as two meal bolus compartments 240, 245 that are connected to the blood compartment 220. The meal boluses may be added to the first and second meal-bolus chambers or compartments 240, 245, transported from the first bolus chamber 240 to the second bolus chamber 245, and then transported to the blood compartment 220. The modeled transport of insulin between compartments may be controlled in part by the insulin time constant ($k_I$) and the difference in insulin concentrations between the two compartments 240, 245.

Still referring to FIG. 5, the blood chamber or compartment 220 models the transport of the micro-bolus insulin, carbohydrates, and meal bolus insulin into the blood stream as well as the effects of insulin and carbohydrates on physiological glucose concentration. The modeled physiological glucose concentration may be controlled by the previous physiological glucose value, the insulin sensitivity ($S_I$), the insulin concentration in the second subcutaneous chamber ($I_{S2}$), the carbohydrate concentration in the second carbohydrate chamber ($C_2$), the insulin concentration in the second bolus chamber ($I_{B,2}$), the insulin time constant ($k_I$), and the meal action time ($k_C$).

The subcutaneous glucose compartment 225 models the transport of glucose from the blood stream compartment 220 to the interstitial tissue under the skin when the continuous glucose monitor (CGM) measures the glucose concentration. The modeled transport of glucose between the blood compartment 220 and the subcutaneous compartment 225 may be controlled in part by a sensor constant ($k_{SENSOR}$) and the difference in glucose concentrations between the two compartments 220, 225.

The example model described in FIG. 5 may also be described by the following set of linear difference equations:

$$
\left.\begin{aligned}
IG(t+dt) &= 1(-k_{SENSOR}dt)\cdot IG(t) + k_{SENSOR}dt\cdot PG(t);\\
PG(t+dt) &= PG(t) - S_I k_I dt\cdot I_{S,2}(t) + k_C dt\cdot C_2(t) - S_I k_I dt\cdot I_{B,2}(t)\\
I_{S,2}(t+dt) &= (1-k_I dt)\cdot I_{S,2}(t) + k_I dt\cdot I_{S,1}(t);\\
I_{S,1}(t+dt) &= (1-k_I dt)\cdot I_{S,1}(t) + b_S\cdot\delta_I(t);\\
C_2(t+dt) &= (1-k_C dt)\cdot C_2(t) + k_C dt\cdot C_1(t);\\
C_1(t+dt) &= (1-k_C dt)\cdot C_1(t);\\
I_{B,2}(t+dt) &= (1-k_I dt)\cdot I_{B,2}(t) + k_I dt\cdot I_{B,1}(t);\text{ and}\\
I_{B,1}(t+dt) &= (1-k_I dt)\cdot I_{B,1}(t).
\end{aligned}\right\}
\quad \text{(Eqn. 1)}
$$

Each state vector is associated with a unique model that includes these equations but have a unique set of constants.

Continuing to refer to FIG. 5, the concentrations of insulin, carbohydrates, and glucose in the eight compartments can be described as the state vector x(t), where x(t) has the following components: $x_1(t)$=IG, $x_2(t)$=PG, $x_3(t)=I_{S2}$, $x_4(t)=I_{S1}$, $x_5(t)=C_2$, $x_6(t)=C_1$, $x_7(t)=I_{B2}$, and $x_8(t)=I_{B1}$. The state vector describes the condition of the body including the important PG and IG values at time (t). The next state vector (x(t+τ)) is determined from the current state vector (x(t)) and the relationships described in FIG. 5.

The state space equations above may be written as a matrix equation:

$$x(t+\tau)=A_{dt}^{N}\cdot x(t)+B\cdot u(t) \quad \text{(Eqn. 2)}$$

where x(t) is the state vector at time t, and x(t+τ) is the state vector τ minutes later, $A_{dt}$ is a system matrix representing the equations of the model (Eqn. 1) wherein $b_s$ is zero. In one embodiment, B is a input vector that contains $b_s$ in the row for the first insulin compartment and u(t) is the optimal-basal deviation ($\delta_I$). In order to propagate the state vector forward in time by the update period ($\tau_{UPD}$), the multiplication of $A_{dt}\cdot x(t)$ may be repeated N times, where $N=\cdot\tau_{UPD}/dt$, and the multiplication of B·u(t) may be performed. Equation 2 is exercised to advance each state vector, where each state vector has a unique model matrix, $A_{dt}$, and disturbance matrix B.

The model described in FIG. 5 and Eqn. 1 describes an exemplary embodiment of a model in the MMPC algorithm. In other embodiments, the number of model compartments may be fewer or greater than eight. In one embodiment, a minimal model is used comprising one insulin compartment and one carbohydrate compartment, where each compartment is connected to a physiological glucose chamber. This minimal model may be described by a simpler set of equations labeled Eqns. 1A:

$$\left.\begin{aligned} PG(t+dt) &= PG(t) - S_I k_I dt\cdot I_{S,2}(t) + k_C dt\cdot C_2(t) \\ I_{S,1}(t+dt) &= (1-k_I dt)\cdot I_{S,1}(t) + b_s\cdot \delta_I(t);\text{ and} \\ C_2(t+dt) &= (1-k_C dt)\cdot C_1(t); \end{aligned}\right\} \quad \text{(Eqns. 1A)}$$

In other embodiments, another compartment may be added for bolus insulin that is modeled separately from basal insulin and the bolus insulin compartment is connected to the physiological glucose compartment. In still other embodiments, a compartment may be added to model insulin in the interstitial fluid, where this compartment is connected to the physiological glucose compartment.

Propagating the State Vector

Figure 6:
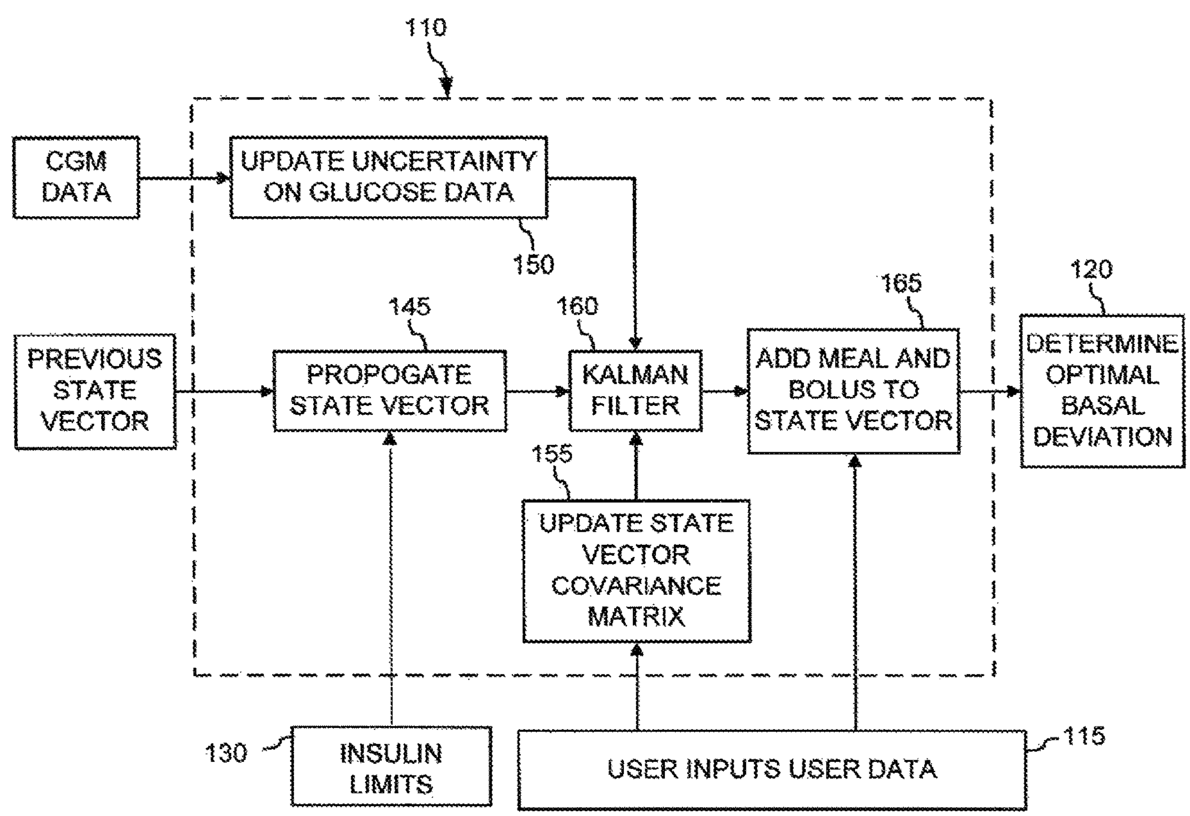
FIG. 6 depicts a block diagram of the propagation and filtering of a state vector using its associated model and covariance matrix.

FIG. 6 illustrates an exemplary schematic representation of propagating each state vector x(t) to state vector x(t+τ) in the MMPC algorithm 100. Propagating each state vector x(t) to state vector x(t+τ) begins by advancing each state vector $x_P(t)$ to its preliminary state vector $x_P(t+\tau)$ using the state model associated with the state vector and Eqn. 2 in block 145. Each preliminary state vector $x_P(t+\tau)$ is a preliminary estimation of the current state. If current glucose data is available from the CGM, then in block 160 each preliminary state vector $x_P(t+\tau)$ may be filtered with a Kalman filter to produce filtered state vectors $x_F(t+\tau)$. If glucose data is not available or the Kalman filter is not called, then the preliminary state vectors are passed through block 145. In block 165, the values of the bolus insulin and carbohydrate states of each preliminary state vector $x_F(t+\tau)$ or each filtered state vector $x_F(t+\tau)$ may be further corrected for a meal occurring during the most recent update period to determine the propagated state vectors x(t+τ). If a meal has not occurred during the most recent update period, then the preliminary state vector $x_F(t+\tau)$ or filtered state vector $x_F(t+\tau)$ pass through block 165 unchanged to become the propagated state vector x(t+τ). Illustratively, the references to state vectors x(t) imply all the state vectors $x_j(t)$ when j=1 to J and J is the number of state vectors. Therefore reference to state vectors x(t), model constants such as $k_I$, $S_I$, covariance matrices P, Q, elements in the covariance matrices and performance indices $P_j(t)$. Each of these variables refer to a plurality of values such the state vectors $x_j(t)$.

In the illustrative embodiment, the MMPC algorithm 100 initializes the plurality of state vectors using one or more of the following list of parameters including, but not limited to, current time, estimate of IG, Total Daily Dose of insulin (TDD), Total Daily Basal dose (TBD), basal pattern, meal history over past four hours, insulin bolus history over past four hours and insulin-to-carbohydrate ratio (ICR). The MMPC algorithm 100 initializes the state vector with estimate of IG for the interstitial glucose value and the physiological glucose value. The carbohydrate and bolus insulin values are determined from the meal history and insulin bolus history and equations similar Eqns. 3-6 that are described below.

Referring to FIG. 6, preliminary state vectors $x_P(t+\tau)$ are filtered in block 160 with a Kalman filter to update the state variables in each preliminary state vector $x_P(t)$ based on the measured glucose data from the glucose sensor 22 and the covariance matrices P(t), Q(t), and R(t). The covariance matrix R(t) is the uncertainty of the glucose measurement and may be updated in block 150. The uncertainty of each state vector is carried in the covariance matrixes P(t) and Q(t). Each state vector is associated with unique covariance matrixes P and Q. Each covariance matrix P(t) is updated at each update interval ($\tau_{UPD}$) in block 155. The values in the covariance matrix P(t) may be further modified in block 155 based on the size and or timing of a meal.

Figure 7:
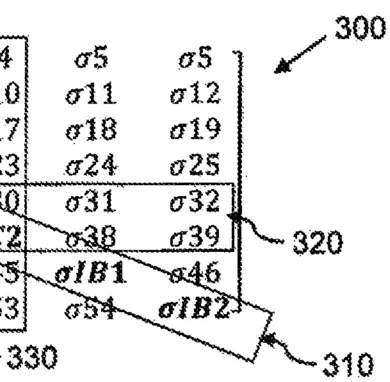
FIG. 7 depicts an example of a covariance matrix.

An example of a covariance matrix P(t) is represented as matrix 300 in FIG. 7. The diagonal terms 310 lists the uncertainty of the state variables in a state vector at time t. The non-diagonal terms are herein referred to as cross-correlation terms or cross terms. The cross terms list the effect of the uncertainty of one state variable on the other state variables. In one example, the uncertainty of the carbohydrates in the first compartment (first carbohydrate state variable) is the element σC1 at the fourth row and column and the uncertainty in the carbohydrates in the second compartment (second carbohydrate state variable) is the element σC2 at the fifth row and column. The non-diagonal elements in the fourth and fifth row 320 and fourth and fifth column 330 are the effects of the carbohydrate uncertainty on the uncertainty of the other body vector values including IG, PG, insulin in subcutaneous compartments 1 and 2, and insulin in bolus compartments 1 and 2. The Q(t) covariance matrix is a diagonal matrix with the initial uncertainty of each state variable along the diagonal 310 and zeros for all the cross terms. The Q(t) matrix is constant except for changes in response to meals when the MMPC algorithm 100 may change one or more values as explained below.

In block 155 each covariance matrix P(t) is advanced for the update interval per Eqn. 3:

$$P(t+\tau)=A_{dt}^{N}\cdot P(t)\cdot(A_{dt}^{T})^{N}+Q(t), \quad \text{(Eqn. 3)}$$

where $A_{dt}$ is the system matrix described above. The P matrix is updated before the Kalman filter is applied to the state vector in Eqn. 4. In block 160, the preliminary state vectors, $x_P(t+\tau)$, from block 145 may be filtered with a Kalman filter when glucose data ($IG_{DATA}$) is available from the glucose sensor. The Kalman filter processes information from the glucose sensor and the uncertainty of in the data and the state variables as described in the Kalman matrix to improve the estimates of the state variables in the preliminary state vector. The Kalman matrix K(t) for each state vector is updated with the latest covariance matrix P(t) from Eqn. 3 before the preliminary state vector is filtered. The Kalman Matrix K(t) is updated per Eqn. 4:

$$K(t) = \frac{P(t)\cdot C^T}{C\cdot P(t)\cdot C^T + R} \quad \text{(Eqn. 4)}$$

where C is a unit conversion matrix and R is the uncertainty of the glucose measurement $IG_{DATA}$.variable. The filtered state vector $x_F(t)$ is calculated per Eqn. 5:

$$x_F(t)=x_P(t)+K\cdot(IG_{DATA}-IG(t)). \quad \text{(Eqn. 5)}$$

where IG(t) is the current estimate of the interstitial glucose in the preliminary state vector $x_p(t)$ and K is the Kalman matrix. Finally, the covariance matrix P is further modified after the Kalman matrix K is calculated per Eqn. 6, $$P(t)=P(t)-K(t)\cdot C\cdot P(t). \quad \text{(Eqn. 6)}$$

In some embodiments, the symmetric diagonal covariance matrix Q(t) has an estimate of the standard deviation of error in the glucose and subcutaneous insulin for the diagonal glucose terms σIG, σPG, and subcutaneous insulin terms σI1, σI2. If the average meal time is greater than a predetermined time, then the diagonal terms in the covariance matrix Q(t) for carbohydrates (σC1, σC2) and bolus insulin (σIB1, σIB2) are zero. The average meal time is a weighted average of meals in the past predetermined time where each meal time is weighted by the amount of carbohydrates consumed at that meal. In another embodiment, the carbohydrate and bolus insulin terms in the Q(t) covariance matrix are zero if no meal occurred in the most recent predefined period. In another embodiment, the carbohydrate and bolus insulin terms in the Q covariance matrix are zero if no meal larger than a predefined amount of carbohydrates has occurred in the last predefined number of minutes. An exemplary predefined amount of carbohydrates is 5 grams, and an exemplary predefined time is 120 minutes, although other suitable thresholds may be implemented.

In one example of setting the diagonal values of the Q(t) matrix, the estimated standard deviation of error in the state variables is a percentage of the estimated insulin need ($I_{EBN}$).

In one embodiment, when a meal of a predetermined size has been consumed within a predetermined time period in the past, the diagonal terms in the Q(t) matrix for carbohydrate (σC1, σC2) and bolus insulin (σIB1 σIB2) are set to estimates of the standard deviation of error in the carbohydrate ($C_1$, $C_2$) and bolus insulin ($I_{B1}$, $I_{B2}$) values. In one example, the estimated standard deviation of error in the carbohydrate (σC1, σC2) are based on a percentage (e.g., 10%) of the sum of carbohydrates in carbohydrate compartments 1 and 2, and the estimated standard deviation of error in the bolus insulin values (σIB1 σIB2) are based on a percentage of $I_{EBN}$.

In one example, the diagonal terms for the uncertainty of the carbohydrate and bolus insulin are set to non-zero values when the sum of carbohydrates in the carbohydrate compartments exceeds a threshold (e.g., 5 grams) and the average meal time is between a low threshold (e.g., 40 minutes) and a high threshold (e.g., 210 minutes). In one embodiment, the average meal time is a weighted average of meals in the past 210 minutes where each meal time is weighted by the amount of carbohydrates consumed at that meal.

In one embodiment, when a meal has not been consumed for a predetermined amount of time, all the carbohydrate and bolus insulin terms in the covariance matrices P and Q are changed to zero. Referring now to FIG. 7, the carbohydrate terms refers to the elements in the P matrix 300 aligned with the terms σC1, σC2 and the terms σC1, σC2 (320, 330). Similarly, the bolus insulin terms in the covariance matrix P are the terms aligned with the bolus insulin terms σIB1, σIB2 and the terms σIB1, σIB2. The carbohydrate and bolus insulin terms in the Q matrix are the diagonal terms for the uncertainty of the carbohydrate and bolus insulin state variables. In one embodiment, all the carbohydrate and bolus insulin terms are set to zero in both the P and the Q matrices when a meal has not occurred for a predefined period of time. In one embodiment, the predefined period of time is 210 minutes. Setting the meal and bolus insulin values in the covariance matrices P, Q to zero may increase the likelihood of improved model stability when less than a predetermined amount of carbohydrates have been consumed within a predefined time window.

Limits on Filtered State Variables

Referring again to FIG. 6, block 160 may include one or more of corrections that limit or clip variables in the filtered state vector $x_F(t)$ resulting from applying the Kalman filter and glucose data to the preliminary state vectors. In some embodiments, the MMPC algorithm 100 limits the sum of the subcutaneous insulin state variables in the filtered state vector, $x_F(t)$ to values above a predetermined minimum insulin concentration. In one example, if the sum of insulin in all the subcutaneous compartments is less than a predetermined factor of the basal insulin, then the insulin in each compartment is increased so that the sum of the new insulin values is equal to the predetermined insulin value. In some embodiments, the values of the insulin state variables are changed so that ratio of one insulin state variable to another insulin state variable in the same state vector are unchanged. In one embodiment, the values of insulin may be increased by multiplying the insulin values by a factor. In some embodiments, the basal insulin multiplied by the predetermined insulin factor is equal to the predetermined insulin value. In one example, the predetermined factor is approximately one half the estimated basal need ($I_{EBN}$).

In some embodiments, the MMPC algorithm 100 limits the difference between preliminary or unfiltered state variables and Kalman filtered state variables for carbohydrates and bolus insulin. In some examples, if the sum of the carbohydrates in the filtered state vector is greater than a first predetermined factor of the sum of the carbohydrates in the unfiltered state vector, then the filtered values for carbohydrate are decreased so their sum is equal to the product of a second predetermined factor and the unfiltered carbohydrate sum. In one example, the first and second predetermined factors are equal.

In some embodiments, if the sum of the bolus insulin in the filtered state vector value is less than a first predetermined fraction of the sum of the bolus insulin in the unfiltered state vector, then the filtered values for bolus insulin will be increased so their sum is equal to a second predetermined fraction of the sum of the unfiltered bolus insulin values. In one example the first and second predetermined fractions are equal.

The plurality of filtered state vectors, $x_F(t+\tau)$, that have may have been corrected with the Kalman filter as described above are then passed to block 165, where the filtered state vectors are updated to include the effect of meals and the associated insulin boluses. The effects of a meal, and meal-bolus that occurred during the previous $\tau_{UPD}$ minutes are added to the filtered state vector, $x_F(t+\tau)$, in block 165 to produce the propagated state vector $x(t+\tau)$. The carbohydrates of the meal are added directly to the carbohydrate state variables in each of the state vectors. In some embodiments, where the model includes two compartments for carbohydrates the carbohydrate state variables are updated per Eqns. 7,8:

$$C_1 = C_1 + CarboRatio \cdot \exp\left(-\frac{\Delta t}{k_C}\right) \cdot MealCarbo \quad \text{(Eqn. 7)}$$

$$C_2 = C_2 + CarboRatio \cdot \left(\frac{\Delta t}{k_C}\right) \cdot \exp\left(-\frac{\Delta t}{k_C}\right) \cdot MealCarbo \quad \text{(Eqn. 8)}$$

where CarboRatio is a unit conversion factor that converts grams of carbohydrate to a concentration of carbohydrates per liter e.g. mmols/L or μmol/L, Δt is the time between the meal and the time of the current calculation, and MealCarbo is the amount of carbohydrates in the meal.

The effects of a meal-bolus of insulin may be added directly to the insulin bolus values of the corrected updated state vector ($I_{B,1}$, $I_{B,2}$) per:

$$I_{B,1} = I_{B,1} + S_I \cdot \exp\left(-\frac{\Delta t}{k_S}\right) \cdot \text{Bolus} \quad \text{(Eqn. 9)}$$

$$I_{B,2} = I_{B,2} + S_I \cdot \left(\frac{\Delta t}{k_S}\right) \cdot \exp\left(-\frac{\Delta t}{k_S}\right) \cdot \text{Bolus} \quad \text{(Eqn. 10)}$$

where Δt is the time between the bolus infusion and the time of the current calculation, and Bolus is an amount of insulin determined to compensate for the added carbohydrates in the variable MealCarbo of Eqns. 7,9. In some embodiments, the value of the Bolus may not equal the bolus delivered by the pump, but rather be calculated from the amount of carbohydrates added to the carbohydrate compartments of the model. In some embodiments, using a Bolus calculated from the carbohydrates added to the model may improve model stability and improve the prediction of physiological glucose values in the future. In some embodiments, the Bolus value is calculated based on the MealCarbo and the estimated insulin basal need as, Bolus=MealCarbo/$I_{EBN}$·Fc, where Fc is a units conversion constant.

In some embodiments, block 165 further corrects state vector $x(t+\tau)$ by increasing the value of physiological glucose (PG) to reflect the appearance of glucose due to the delivery of a glucagon bolus. The correction of the PG value is defined by:

$$PG=PG+\Sigma_{i=1}^{N} g_i=PG+\Sigma_{i=1}^{N} k_{GLN}^2 (t-t_o(i))\, e^{-k_{GLN}(t-t_o(i))} u_g(i) \quad \text{(Eqn. 11)}$$

where N is the number of previous glucagon boluses, $u_g(i)$ is the size of the glucagon boluses, $t_o(i)$ is the time of glucagon bolus administration, and $k_{GLN}$ is the a transfer rate parameter representing the lag time between subcutaneous glucagon delivery and its action. The plurality of propagated, filtered and corrected state vectors, $x(t+\tau)$, is then passed out of block 110. In some embodiments, the plurality of state vectors, $x(t+\tau)$, are passed to the block 120, where the optimal basal insulin deviation is determined.

Determining Optimal Basal Insulin Deviation

Referring now to FIG. 4, the MMPC algorithm 100 in block 120 may determine the optimal basal insulin deviation by selecting the state vector and its model that best matches past interstitial glucose data ($IG_{DATA}$) from the CGM data (block 126), using the selected-state vector and its model to predict the glucose concentration throughout the following predictive period to the prediction horizon (block 128), and determining the optimal deviation from the basal profile over the predictive period in block 124 based an objective function, the glucose target determined in 122, the basal profile from 115, and one or more limits on insulin delivery rates described herein. A volume of insulin equal to the insulin trajectory for first infusion period is passed to block 130 as the optimal-basal deviation from the basal profile.

In block 126, the MMPC algorithm 100 selects the state vector and its model that best matches the glucose data or $IG_{DATA}$ values over the historical period. In some embodiments, the $IG_{DATA}$ values are measured by the CGM 22 placed on the user's body. In other embodiments, the glucose data is measured with a glucose sensor. In one embodiment, an identification error $e_j(t)$ is calculated for each state vector at each update interval as the difference between the each state variable, $IG_j(t)$ with the $IG_{DATA}$ at time t. A performance index $P_j(t)$ is then calculated for each state vector j which sums the identification errors, $e_j(t)$ over a period of time. In some embodiments, the performance value, $P_j(t)$ is the sum of the weighted and squared identification errors over a moving window in time (e.g., 2 hours or other suitable windows). In some embodiments, the weighting increases for more recent identification errors.

In one embodiment, the performance value is the weighted sum of the squared errors, where the weighting is an exponential decay function that gives more weight to more recent data. In one embodiment, the performance value for each model j is defined as:

$$P_j(t)=a\cdot e_j(t)^2+\Sigma_{i=1}^{M} b^2 e^{-ci} e_j(i)^2 \quad \text{(Eqn. 12)}$$

where a and b are constants that determine the contribution of instantaneous and long-term accuracy to the index, the error $e_j(t)$ is the difference between the measured and determined IG value for model j at the current time t and $e_j(i)$ is a vector of the previous error values of the $j^{th}$ model $e_j(i)=\{e_j(1), e_j(2), \ldots e_j(M)\}$ M is the number of stored error values in error vector $e_1(i)$ in the moving window for each state vector and model j, c is a constant defines the exponential decay function used to weight the error $E_j(i)$. In some embodiments, the use of the performance index to select the state model increases the likelihood of stability in the MMPC algorithm 100.

The MMPC algorithm 100, in block 126, may select the state vector and model with the lowest current value performance value Pj(t) and pass the selected-state vector and model on to block 128.

In some embodiments, after meal time a subset of the state vectors are considered in block 126 to identify the best match to past IG data. In some embodiments, the subset of considered state vectors contain only those state vectors whose model have relatively faster insulin absorption values. The state vectors associated with models that have relatively slower insulin absorption times are excluded from consideration to determine the state vector with the best fit to past IG data. In some embodiments, the MMPC algorithm 100 limits the state vectors considered in block 126 to state vectors associated with models with insulin absorption times less than a first insulin absorption threshold. An exemplary first insulin absorption threshold is about one hour or other suitable thresholds.

The MMPC algorithm 100 in block 128 advances the state vector selected in block 126 using the model associated with the selected-state vector to predict the physiological glucose concentration, PG(t) out to the prediction horizon. The period from the current time to the prediction horizon is herein referred to as the prediction period. In some embodiments, the selected-state vector is advanced under steady state conditions where no meal inputs and no meal insulin boluses occur. In some embodiments, the selected-state vector is advanced assuming a basal insulin dosage. Basal insulin dosage may be a zero basal deviation, a basal profile or a constant basal dose. In a preferred embodiment, the selected-state vector is advanced assuming a zero basal deviation, no meals and no insulin boluses during the prediction period. Block 128 passes the resulting predicted physiological glucose concentration values $PG_{P,I}$ to block 124, where the optimal insulin deviation from the basal profile value is determined.

The example MMPC algorithm 100, in block 124, determines the optimal deviations from the basal profile assuming no meals over the prediction period. The optimal deviations from the basal profile may be a sequence of insulin dose deviations over the prediction period that minimize an objective function. In some embodiments, the objective function comprises the weighted-squared-glucose difference at each time step over the prediction period. The glucose difference is the difference between the target glucose values and the value of the predicted physiological glucose state variable. The objective function may further comprise the sum of weighted-squared-insulin basal deviation ($\delta_I$) at each time step over the prediction period. In some embodiments, the objective function may further comprise the sum of weighted insulin doses at each time step. Each time step may be equal to the update period ($\tau_{UPD}$) or the injection period ($\tau_{INJ}$) The weighing of either the glucose difference or the insulin doses may be a function of the time or may vary with time after a meal. In one embodiment, the objective function comprises both glucose differences and the basal deviations per Eqn. 13:

$$\text{Cost}=\Sigma_{i=1}^{ph}[w_G(i)\cdot(PG(i)-PG_{TGT}(i))^2+K_{INSULIN}\cdot\tau_I(i)^2] \quad \text{(Eqn. 13)}$$

where $K_{INSULIN}$ is a weighting factor for deviations from the basal insulin dosage, ph is the number of samples or predictions encompassed by the prediction period and the weighting function, $w_G(i)$, may vary over the prediction period. In some embodiments, the weighting function may give significantly more weight to the final difference between the predicted physiological glucose, PG(ph), and the target glucose $PG_{TGT}$(ph). Further, in some embodiments the final weighting, $w_G$(ph), is larger than the sum of the previous weighting values $w_G(1)$ through $w_G$(ph−1). In some embodiments, the weight function, $w_G(i)$, may be reduced for periods after meals. Further, in some embodiments the weight function, $w_G(i)$, may be a nominal value for intervals greater than a meal period and much less than the nominal value for intervals less than the meal period. In some embodiments, the weight function may be less than 1% of the nominal value for a first half of the meal period after a meal and increasing from less than 1% of the nominal value to the nominal value during the second half of the meal period after a meal. In some embodiments the meal period is greater than 3 hours. The target glucose number, $PG_{TGT}(i)$, may be a function some of, but not limited to, a prescribed target glucose value, exercise, time after a meal.

Limits on Insulin Deviations in the Optimization Process

The minimizing of the cost function above is further constrained by limits on the values of the insulin deviation, $\delta_I(i)$ The limits on the insulin deviation, $\delta_I(i)$, may, for example, be based on the open loop insulin rate, $I_{OL}$. The insulin deviation may be limited so that the insulin dose remains between 0 and $I_{MAX}$. Therefore the insulin deviation, $\delta_I(i)$, is limited to the range:

$$-I_{OL}\le\delta_I(i)\le I_{MAX}(i)-I_{OL} \quad \text{(Eqn. 14)}$$

where $I_{OL}$ is defined below and $I_{MAX}(i)$ is a maximum basal dose. In one embodiment, the maximum basal dose may be a fixed value that is predefined by a user or a clinician. In another embodiment, the maximum basal dose may depend on the estimated physiological glucose value, PG, the total daily basal insulin, TDB, and/or the open-loop insulin, $I_{OL}$.

In some embodiments, the maximum basal dose, $I_{MAX}(i)$, is a function of the open loop insulin and the estimated physiological glucose value, PG. In this embodiment, the maximum basal dose may be equal to the product of a first factor and an open loop basal dose for physiological glucose values less than a first predefined glucose threshold. Similarly, the maximum basal dose may be equal to the product of a second factor times the open loop basal dose for physiological glucose values greater than a second glucose threshold predefined, wherein the second factor is greater than the first factor. The maximum basal dose may be equal to an interpolation between the first and second factor times the open loop basal dose based on the physiological glucose value for physiological glucose values between the first and second glucose thresholds. In some embodiments, the first factor is approximately 3 and the first glucose threshold is approximately 7 mMol/L. In some embodiments, second factor is approximately 5 and the second glucose threshold is approximately 12 mMol/L.

In some embodiments, the minimizing of the cost function above is further constrained by limits on the values of the insulin deviation, $\delta_I(i)$, that are listed in the section labeled Insulin Limits. The Insulin Limits listed below may be applied to the optimization process in block 124 at each time point during the prediction period by applying the predicted physiological glucose values and the rate of change of physiological glucose values at the corresponding time points in the prediction period (e.g., $\delta_I(i)$=fcn (PG(i), dPG(i)/dt)).

There are a multitude of numerical algorithms to find the set of optimal insulin deviation commands, $\{\delta_I(1), \delta_I(2) \ldots \delta_I(ph)\}$, which minimize the cost function of Eqn. 13. When the numerical algorithm finds the optimal set of insulin deviation commands in block 120, the MMPC algorithm 100 passes the optimal-basal deviation for the first update interval ($\delta_I(1)$) to block 135, where the optimal deviation is summed with basal profile to equal the next dose request.

Insulin Terms

The MMPC algorithm 100 uses a plurality of insulin values that may be grouped under the term insulin need. The insulin need in some embodiments is data entered by the patient or clinician at the UI 20. In another embodiment, the insulin need data may be stored in the memory on the UI 20, the controller 24, or the pump 12. The insulin need may include a single value or a basal profile. In some embodiments, the insulin need data comprises one or more of the following insulin values: the total daily dose of insulin (TDD); the total basal dose (TBD); the basal dose ($I_{BD}$) which is a single dose rate typically units/hour and the basal profile ($I_{BP}(i)$) which is a list or equation that defines the basal insulin doses over a day. The basal dose may be a value input at the UI 20 by the user, or it may be calculated as a fraction of the TDD. In some embodiments, the basal dose is a basal factor times TDD divided by twenty-four, where the basal factor is less than one. In some embodiments, the factor is 0.55 or another suitable fraction. In other embodiments, the basal dose is the basal insulin is TDB divided by twenty four.

The open loop basal rate, $I_{OL}(t)$, is the input basal profile, $I_{BP}(t)$, limited by high and low limits. The $I_{OL}(t)$ equals $I_{BP}(t)$ except when $I_{BP}(t)$ is less than the low limit wherein $I_{BP}(t)$ equals the low limit. The $I_{OL}(t)$ equals $I_{BP}(t)$ except where $I_{BP}(t)$ is greater than the high limit wherein $I_{BP}(t)$ equals the high limit. In one embodiment, the low limit is half of TDB/24 and the high limit is 1.5 times TDB/24.

The estimated insulin basal need, $I_{EBN}$, is a function of the total daily dose of insulin (TDD) and the total daily basal insulin (TDB) that used to set insulin sensitivity, initial values for covariance limits on filtered insulin values and calculation of the insulin bolus. In one example, the value of $I_{EBN}$ is a fraction of TDD/24. In another example, $I_{EBN}$ is limited by upper and lower bounds, where the upper and lower bounds are based on TDD and TDB.

The total daily dose of insulin (TDD) and total daily basal insulin (TDB) may be constants or may be updated during use. In one embodiment, TDD and TDB are predetermined values. In another embodiment, TDD and TDB are entered by a user or clinician at the user interface or communicated directly to the controller. In another embodiment, the TDD are updated by the controller to average insulin delivered each day over the past 2 weeks. In another embodiment, the TDB may be updated by the controller to the two week average of daily basal insulin delivered. In another embodiment, the TDD and TDB represent the averages of total daily insulin and the total basal insulin respectively over the past 3 days. In another embodiment, the TDD and TDB represent respectively the averages of total daily insulin and the total basal insulin over the past 24 hours.

Target Glucose

As described above, the illustrative MMPC algorithm 100 in block 124 (FIG. 4) implemented by the controller uses a target physiological glucose value ($PG_{TGT}$) when determining the optimal deviation from the basal profile. The $PG_{TGT}$ is a fixed value in some embodiments. In other embodiments, $PG_{TGT}$ is modified from a nominal or preset value ($PG_{NOM}$) when various conditions are present or various events occur. The target physiological glucose value may be determined based on user data communicated to the system 10 via the UI's 20 inputs. Such adjustments of the target physiological glucose value may, for example, occur in response to the announcement of meals and/or exercise. The adjustments of the target glucose value may be governed at least in part by a target modification formula or may be based off predefined values to be used when the certain circumstances exist. Additionally, a target value adjustment may persist for a period after the condition or event occurs. The adjustment may be a static or fixed adjustment over this period or alter in magnitude (e.g., decrease linearly in magnitude) as the time period elapses.

Referring now to block 120 depicted in FIG. 4, the glucose target may be determined in block 122 and provided to block 124 which may then determine the optimal deviations from the basal profile as described above. Block 122 receives meal and exercise input data from block 115 and may alter the target physiological glucose value. As part of determining the optimal deviation in the basal profile in block 120 the nominal target glucose value may be adjusted from its nominal value. An exemplary nominal target glucose value is 6 mmol/L, although other suitable values may be implemented. The target glucose value may be adjusted in some embodiments if the patient has announced exercise and not yet ended exercise while the MMPC algorithm 100 is determining the optimal deviation of the basal profile in block 120. In other embodiments, the target glucose value may be modified for exercise if a period of exercise has occurred for a predetermined period within a predefined time of the current time. In some embodiments, meal data may alter the target physiological glucose value if the patient 14 has announced a meal within a predefined period of the determination of the optimal-basal deviation.

An exercise announcement may modify the physiological glucose target value from a preset or nominal value to an exercise target value. In some embodiments, the exercise target value may be at or about 3 mmol/L greater than the preset or nominal target value. In some embodiments, the preset or nominal target value may be at or about 6 mmol/L and the exercise target value may be at or about 9 mmol/L.

A meal announcement or meal data may be input to a formula which increases the target value based on proximity to the meal. The formula may be arranged such that the meal has a greater effect on the target values in close temporal proximity to the meal. As the time from the consumption of the meal increases, the target value may be altered to a lesser degree. After a certain predefined time period has elapsed, the meal input data may no longer have an effect in determining any target value adjustment and a preset or nominal target value may be used. The effect of the meal event on the target physiological glucose value may change (e.g., decrease) in a linear fashion over time.

After the physiological glucose target value is set, a number of checks may be performed based on a physiological glucose target. These checks may cause a modification of the glucose target value ($PG_{TGT}$) to an altered final value in some instances.

Insulin Limit Checks

After the state vectors have been propagated and an optimal deviation from the basal profile has been determined in block 120, the controller 24 may compare or check the optimal deviations from the basal profile against one or more insulin limits in block 130 of FIG. 3. In some embodiments, a plurality of criteria may be used. The optimal deviations ($\delta_I$) from the basal profile may be altered to hold the delivered insulin within limits based on the physiological glucose or rate of change of physiological glucose of the selected-state vectors. The alteration of the optimal deviation may also be based on the total daily dose of insulin (TDD) and/or the total daily basal insulin (TDB). In some embodiments, the optimal deviations from the basal profile may be updated once or multiple times as the optimal deviations from the basal profile pass through the plurality of limit checks. The resulting limit checked optimal-basal deviation ($\delta_I$) may be then passed to the dose request block 135, where the basal dose or basal profile will be added to the checked-basal deviation to produce the requested insulin dose that is sent to the pump 12.

Figure 8:
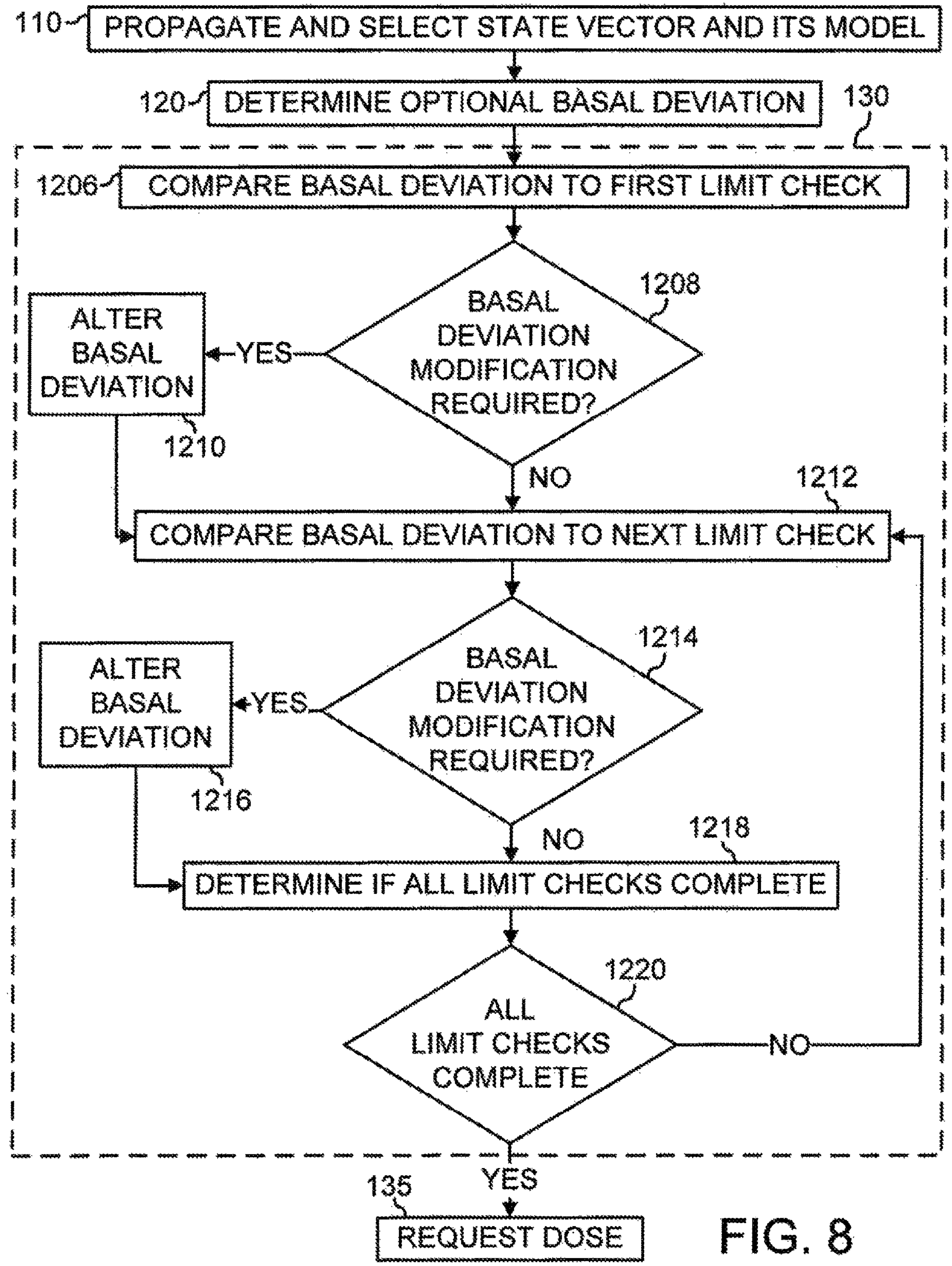
FIG. 8 depicts a flowchart which details a number of example actions which may be executed to determine if an optimal-basal deviation requires alteration.

FIG. 8 depicts an example flowchart 1200 which details a number of example actions which may be executed to determine if an optimal deviation from the basal profile requires alteration. The optimal-basal deviation from the basal profile is compared by the controller 24 to a first criteria or first limit check in block 1206. If, in block 1208, the comparison indicates no modification is needed based on the first insulin limit check, the optimal-basal deviation may be compared to a next insulin limit check in block 1212. If, in block 1208, the comparison indicates that the optimal-basal deviation requires alteration, the optimal-basal deviation may be changed to an updated-basal deviation in block 1210. The updated-basal deviation may then be compared by the controller 24 to the next insulin limit check in block 1212.

If, in block 1214, the comparison indicates that the optimal or updated-basal deviation requires alteration, the basal deviation may be updated to an updated-basal deviation in block 1216. After modification in block 1216 or if, in block 1214, the comparison indicates no modification is needed based on the insulin limit check, it may be determined whether all insulin limit checks have been completed in block 1218. If, in block 1220, all insulin limit checks have not been completed the controller 24 may return to block 1212 and perform the next insulin limit check. This may be repeated until "n" number of insulin limit checks have been made by the controller 24. In some embodiments, "n" may be up to or equal to six. If, in block 1220, all insulin limit checks have been completed, the optimal-basal deviation or updated-basal deviation may be provided as the checked-basal deviation to the pump 12, and the pump 12 may administer a micro-bolus amount of medication to the patient 14.

Equations 15-17 illustrate exemplary insulin limit checks that may be applied in block 130 of FIG. 3. In one embodiment, Eqns. 15-17 are applied sequentially to the optimal basal deviation produced by block 120. Other embodiments may include some or all of the following limits on the basal insulin deviation. These insulin limits are applied to the optimal deviation of the insulin basal profile or optimal-basal deviation ($\delta_I$) produced in block 120 in FIGS. 3, 4 to produce an updated-basal deviation that is supplied to block 135 where the delivered dose is requested from the pump 12.

In order to make the MMPC algorithm 100 respond asymmetrically to requests to deliver insulin at a rate different from the basal rate, the insulin limit block 130 in one embodiment biases changes from the basal insulin or basal profile to lower doses by increasing the magnitude of negative basal deviations and leaving positive basal deviations unchanged. If, for example, the optimal-basal deviation from block 120 is negative, then the magnitude of the optimal-basal deviation may be further increased per Eqn. 15:

$$\delta_I=\delta_I(i)*F1 \text{ if } \delta_I(i)<0 \quad \text{(Eqn. 15)}$$

where F1 is a value greater than one. If the optimal-basal deviation is positive, the optimal-basal deviation is not changed. After increasing the magnitude of the optimal-basal deviation, if required, the controller 24 performs a next insulin limit check.

The MMPC algorithm 100 in some embodiments, assures a minimum insulin delivery when the physiological glucose is high. In some embodiments, the controller 24 limits the optimal-basal deviation to be greater than or equal to zero when the estimated physiological glucose of the selected-state vector exceeds a predetermined high glucose threshold. Holding the optimal-basal deviation at zero or above results in the delivered insulin being greater than or equal to the basal profile. In one example, the basal deviation is limited based on a high glucose threshold pre Eqn. 16:

$$\delta_I=\max(0,\delta_I) \text{ if } PG>PG_{MAX} \quad \text{(Eqn. 16)}$$

where $PG_{MAX}$ is the high physiological glucose threshold. In one example, the high physiological threshold is at or about 13.7 mmol/L. The equation form wherein A=max(B,C) means that A is set equal to the larger value of B or C.

The MMPC algorithm 100 in some embodiments limits the insulin delivery when the physiological glucose is low. In some embodiments, the controller 24 limits the optimal-basal deviation to less than or equal to a first predetermined low value when the physiological glucose of the selected-state vector is less than a predetermined low physiological glucose threshold.

The MMPC algorithm 100 in some embodiments further limits the insulin delivery when the physiological glucose is low and dropping. In some embodiments, the controller 24 limits the optimal-basal deviation to less than or equal to a second predetermined low value when the physiological glucose of the selected-state vector is less than a predetermined low physiological glucose threshold and decreasing with time. The second predetermined low value may be less than a first predetermined low value.

The MMPC algorithm 100 in some embodiments further limits the insulin delivery when the physiological glucose is very low. In some embodiments, the controller 24 limits the optimal-basal deviation to less than or equal to a third predetermined low value when the physiological glucose of the selected-state vector is less than a second predetermined low physiological glucose threshold.

The MMPC algorithm 100 in some embodiments assures a minimum delivery of insulin over a relatively long time scale by supplying a minimum level of insulin after a predetermined period low insulin doses. In some embodiments, the controller 24 limits the insulin dose to be equal to or greater than a minimum dose when the average insulin doses over a predefined time period is below a predefined dose threshold. The average delivered insulin doses may be determined by the controller 24 by averaging the insulin doses requested by the MMPC algorithm 100 in block 135 in FIG. 3 over a predefined period. In some embodiments, the predefined period is about two hours. The delivered insulin threshold may be a small positive value. In some embodiments, the delivered insulin threshold is set at or about 0.05 units of insulin per hour.

In some embodiments, minimum long term delivery may assured by limiting the optimal-basal deviation to be equal to or greater than a first predetermined threshold, when the average delivered insulin dose over the predefined time period is less than the delivered insulin threshold. In one embodiment the first predetermined threshold value is zero, so the delivered insulin will be at least equal to the basal profile. In one embodiment this insulin limit is described in Eqn. 17:

$$\delta_I = \max(0, \delta_I) \text{ if } \frac{1}{N}\sum_{i=1}^{N} I_D(i) < I_{MIN} \quad \text{(Eqn. 17)}$$

where $I_D(i)$ are the past requested insulin doses and IMIN is the delivered insulin threshold.

Closed Loop Control of Glucagon

In some embodiments, the system 10 may include multiple medication reservoirs 16. One medication reservoir 16 may include insulin and another reservoir may include glucagon, for example. Using data from a CGM 22, glucagon may be delivered to a patient 14 in closed loop fashion along with insulin. In some systems, administration of glucagon in addition to insulin may help to increase further the amount of time a patient 14 spends in a euglycemic state.

Glucagon delivery to a patient 14 may be controlled by a number of predefined glucagon rules which may vary depending on the embodiment. In some embodiments, the size of the glucagon bolus allotted for delivery to a patient 14 in a given day may a function of one or more of the following factors including, but not limited to: a recent meal, exercise, physiological glucose concentration, rate of change of glucose concentration, basal insulin data and an estimate of insulin on board (IOB). In some embodiments, the glucagon bolus may be may be increased if the user indicates exercise. In some embodiments, the glucagon dose may be increased during exercise. In some embodiments, the glucagon bolus may be set to zero or canceled for a period after a meal. In one embodiment, the glucagon bolus is set to zero for 120 minutes after a meal.

In some embodiments, a glucagon bolus may be delivered only when the rate of change physiological glucose (dPG/dt) is less than a glucose rate threshold ($R_{PG}$). The glucose rate threshold may be a function of the estimated physiological glucose (PG). The glucose rate threshold ($R_{PG}$) may increase inversely with the estimated physiological glucose (PG), so that the glucose rate threshold will increase with lower physiological glucose (PG) values. The controller delivers glucagon as higher dPG/dt values as the PG levels decrease. In some embodiments, the glucose rate threshold is less than zero, so that glucagon is delivered only when PG is dropping faster than the glucose rate threshold. In these embodiments, the glucose rate threshold increases and has a smaller magnitude as the physiological glucose increases. In some embodiments, the glucose rate threshold may be larger than zero so that glucagon is delivered only when PG is rising slower than the glucose rate threshold. In these embodiments, the glucose rate threshold increases and has a larger magnitude as the physiological glucose increases. In some embodiments, the glucose rate threshold is less than zero for high physiological glucose values and greater than zero for low physiological glucose values. In these embodiments, glucagon is only delivered when PG is dropping faster than the glucose rate threshold at higher physiological glucose levels and at lower physiological glucose values, glucagon is only delivered when PG is rising slower than the glucose rate threshold.

The size or volume of the glucagon bolus ($Gln_B$) may scale with both the rate of change of physiological glucose (dPG/dt) and the estimated value of the physiological glucose (PG). In some embodiments, glucagon bolus with increase with rate of change of physiological glucose. In some embodiments, the amount of the glucagon bolus may increase with decreasing levels of physiological glucose concentration. In some embodiments, the glucagon bolus may increase with the amount of active insulin in the model.

Figure 9:
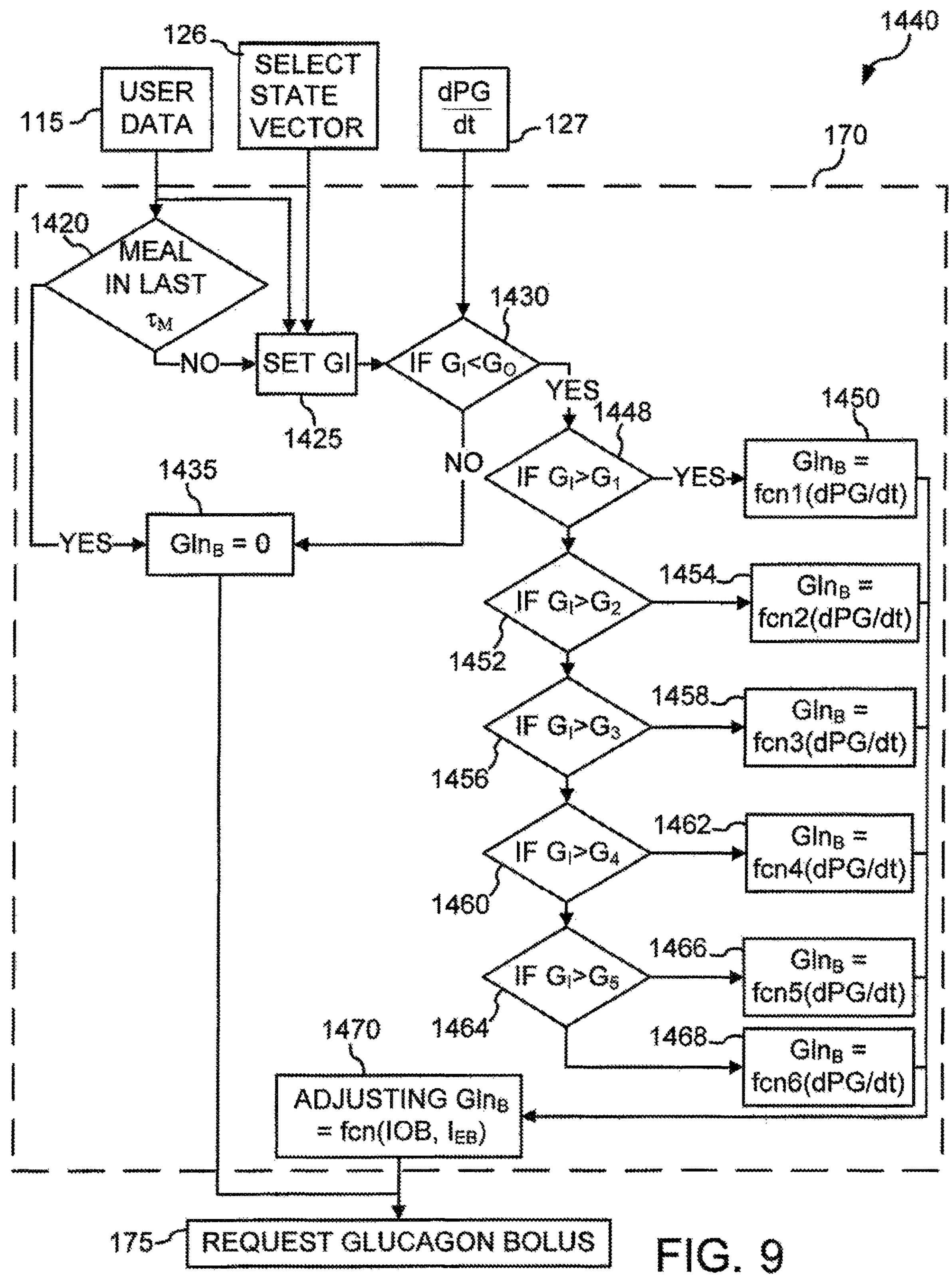
FIG. 9 depicts a flowchart detailing a number of example actions which may be executed to determine a glucagon dose.

In some embodiments, glucagon may be further or alternatively controlled by controller 24 based on the exemplary method illustrated in flowchart 1440 of FIG. 9. The controller 24 in block 170 may determine the requested bolus volume of glucagon based upon receipt of user data on meal and exercise from block 115, the current estimation of physiological glucose in the selected-state vector 126 (FIG. 4), and the rate of change of the physiological glucose (dPG/dt) from block 127. In block 1420, the controller 24 checks if a meal had been consumed within a predefined period of time ($\tau_M$). In one embodiment, $\tau_M$ is 120 minutes. If a meal had been consumed within a period of less than $\tau_M$ then the controller sets the glucagon bolus to zero in block 1435 and exits block 170. If a meal has not been consumed within the past $\tau_M$ period, then the controller determines the glucose input ($G_I$) in block 1425. The glucose input is equal to the physiological glucose (PG) of the selected-state vector 126. In some embodiments, if the user indicates exercise in block 115, the glucose input may be equal to the physiological glucose concentration minus an exercise factor. In one embodiment, the exercise factor is 3 mmol/L. The glucose input value ($G_I$) is then passed to a series of if-then-else logic decisions (Blocks 1430-1468) that set the size of the glucagon bolus based on the glucose input value and the rate of change of the physiological glucose concentration determined in block 127. The resulting glucagon bolus may be updated in block 1470 as a function of the sum of insulin in the selected-state vector and the estimated basal insulin need ($I_{EBN}$).

The if-then-else logic (blocks 1430-1468) and the glucagon bolus modification 1470 are described below. In block 1430 the glucose input ($G_I$) is compared to a primary glucose threshold ($G_0$). If the input glucose is greater than the primary glucose threshold ($G_0$), then the controller sets the glucagon bolus to zero in block 1435 and exits block 170. If the input glucose ($G_I$) is less than the primary glucose threshold ($G_0$), then the controller proceeds to block 1448 and the subsequent if-then-else logic steps that set the glucagon bolus based on the estimated value and rate of change of the physiological glucose.

In block 1448, if the glucose input (G) is greater than a first glucose threshold ($G_I$), then the glucagon bolus is determined by a first function in block 1450 based on the rate of change of physiological glucose concentration (dPG/dt) or the difference of successive physiological glucose values (dy1, dy2). The difference between successive physiological glucose values [PG(i)−PG(i−1) or PG(i)−PG(i−2)] may be considered as a rate of change of physiological glucose (dPG/dt) if the successive values of physiological glucose are taken at fixed intervals. If the glucose input is less than the first glucose threshold, the logic passes to block 1452.

In the first function of block 1450, the glucagon bolus is determined based on the rate of change of glucose (dPG/dt). If the rate of change of glucose is greater than a first rate threshold ($R_{PG}1$), then the glucagon bolus is set to zero ($Gln_B$=0). After setting the glucagon bolus in block 1450, the controller 24 passes to block 1470.

In block 1452, if the glucose input ($G_I$) is greater than a second glucose threshold (G2), then the glucagon bolus is determined by a second function in block 1454 based on the rate of change of physiological glucose (dPG/dt). If the glucose input is less than the second glucose threshold, the logic passes to block 1456.

In the second function of block 1454, the glucagon bolus is determined based on the rate of change of glucose (dPG/dt). If the rate of change of glucose is greater than a second rate threshold ($R_{PG}2$), then the glucagon bolus is set to zero ($Gln_B$=0). After setting the glucagon bolus in block 1454, the controller 24 passes to block 1470.

In block 1456, if the glucose input ($G_I$) is greater than a third glucose threshold ($G_3$), then the glucagon bolus is determined by a third function in block 1458 based on the rate of change of physiological glucose (dPG/dt). If the glucose input is less than the third glucose threshold, the logic passes to block 1460.

In the third function of block 1458, the glucagon bolus is determined based on the rate of change of glucose (dPG/dt). If the rate of change of glucose is greater than a third rate threshold ($R_{PG}3$), then the glucagon bolus is set to zero ($Gln_B$=0). After setting the glucagon bolus in block 1458, the controller 24 passes to block 1470.

In block 1460, if the glucose input ($G_I$) is greater than a fourth glucose threshold ($G_4$), then the glucagon bolus is determined by a fourth function in block 1462 based on the rate of change of physiological glucose (dPG/dt). If the glucose input is less than the fourth glucose threshold, the logic passes to block 1464.

In the fourth function of block 1462, the glucagon bolus is determined based on the rate of change of glucose (dPG/dt). If the rate of change of glucose is greater than a fourth rate threshold ($R_{PG}4$), then the glucagon bolus is set to zero ($Gln_B=0$). After setting the glucagon bolus in block 1462, the controller 24 passes to block 1470.

In block 1464, if the glucose input ($G_I$) is greater than a fifth glucose threshold ($G_{45}$), then the glucagon bolus is determined by a fifth function in block 1466 based on the rate of change of physiological glucose (dPG/dt). If the glucose input is less than the fifth glucose threshold, the logic passes to block 1468.

In the fifth function of block 1466, the glucagon bolus is determined based on the rate of change of glucose (dPG/dt). If the rate of change of glucose is greater than a fifth rate threshold ($R_{PG}5$), then the glucagon bolus is set to zero ($Gln_B=0$). After setting the glucagon bolus in block 1466, the controller 24 passes to block 1470.

In the sixth function of block 1468, the glucagon bolus is determined based on the rate of change of glucose (dPG/dt). If the rate of change of glucose is greater than a sixth rate threshold ($R_{PG}6$), then the glucagon bolus is set to zero ($Gln_B=0$). After setting the glucagon bolus in block 1468, the controller passes to block 1470.

In the illustrated embodiment, the primary glucose threshold is greater than the first glucose threshold, the first glucose threshold is greater than the second glucose threshold, the second glucose threshold is greater than the third glucose threshold, the third glucose threshold is greater than the fourth glucose threshold, and the fourth glucose threshold is greater than the fifth glucose threshold.

In block 1470, the glucagon bolus determined in one of blocks 1450-1468 by one of the first function through the sixth function may be updated based on the active insulin in the body and the estimated basal insulin need ($I_{EBN}$). The active insulin in the body or Insulin on Board (IOB) is the sum of insulin in the insulin compartments of the selected-state vector. In one embodiment represented in FIG. 5 and Eqn. 1, the insulin compartments include the two subcutaneous compartments ($I_{S1}$, $I_{S1}$) and the two bolus compartments ($I_{B1}$, $I_{B1}$). The IOB is based on the basal deviations over time that are requested by block 120, 130 in FIG. 4. The glucagon bolus request from block 1470 or the zero request from 1435 are then passed to the glucagon bolus block 180.

Meal Bolus

Figure 10:
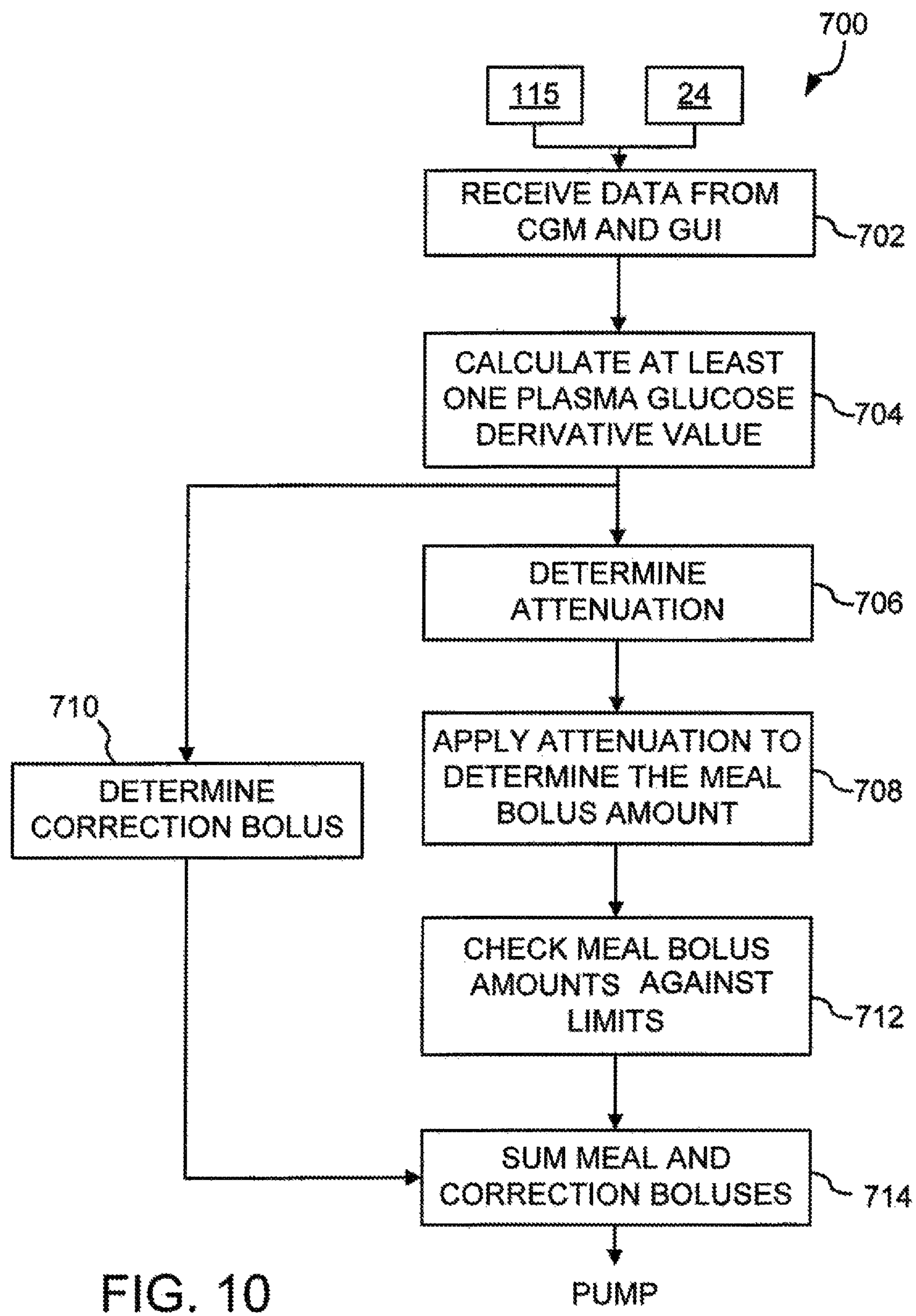
FIG. 10 depicts a flowchart detailing various example logic, which may be applied when determining an amount of drug (e.g., insulin) to be delivered in a meal bolus.

Referring now to the flowchart 700 shown in FIG. 10, various logic rules may be applied when determining an amount of drug (e.g., insulin) to be delivered in a meal bolus to the patient 14 to maintain the physiological glucose concentrations at the desired level or range during and after a meal. In block 702, the current physiological glucose concentration (PG) concentration and the meal data are received. In block 704, the controller 24 may determine at least the rate of change of the physiological glucose concentration (dPG/dt). The dPG/dt may be determined by any suitable method including the at least one method is described herein. The meal bolus is determined from the amount of carbohydrates in the meal (CHO), the insulin to carbohydrate ratio (ICR) and a bolus attenuation factor (Palo), where the bolus attenuation factor reduces the meal bolus when the physiological glucose is relatively low and/or decreasing in value. The closed loop control of the physiological glucose provided by the MMPC algorithm 100 provides a method to provide additional insulin to make up for the reduced meal bolus if needed to maintain euglycemia.

In one embodiment, the physiological glucose concentration values are provided directly from the CGM 22. In some embodiments, the physiological glucose concentrations are the current physiological glucose concentration of the selected-state vector as described above in relation to block 126 in FIG. 4. In another embodiment, the meal bolus algorithm uses physiological glucose values estimated from glucose measurements by the CGM 22.

Referring now to FIGS. 1, 2, when determining a meal bolus, the system 10 may determine a meal bolus amount with inputs from at least one of the glucose sensor 22 and the UI 20. A preliminary value for the meal bolus may be the carbohydrate content of the meal divided by an insulin-to-carbohydrate ratio. The preliminary value for the meal bolus may be attenuated based on the physiological glucose values determined by the controller 24. The carbohydrate content of the meal may be explicitly entered at the UI 20 or may be inferred by the controller 24 from meal data supplied at the UI 20. The insulin to carbohydrate ratio may be input at the UI 20 and/or stored in memory that is readable by the controller 24. The carbohydrate content of the meal may be input by the user as a qualitative judgment of the user. For example, the user may indicate a meal size via the UI 20 of the system 10. In some embodiments, the meals size may be selected from a plurality of categories such as, but not limited to: small, medium, large, or snack.

Referring again to flowchart 700 in FIG. 10, the meal bolus ($BOL_M$) may be calculated from the carbohydrate content of the meal (CHO), the insulin to carbohydrate ratio (ICR) and an attenuation factor. The attenuation factor depends on the physiological glucose concentration and the rate of change of the physiological glucose and determined from a predefined formula in block 706. The meal bolus is determined in block 708. In block 712, the meal bolus is limited to less than a predefined fraction of the total daily insulin (TDD) in block 712. The resulting meal bolus is passed as a delivery request to the pump 12 and the pump 12 may deliver the insulin meal bolus to the user.

The meal bolus algorithm may attenuate the meal bolus of small meals differently than larger meals. For example, if the carbohydrate content of the meal is estimated to be above a carbohydrate threshold ($C_{THD}$), then the meal bolus may be calculated as a product of the carbohydrate value (CHO), and the attenuation factor ($A_{CHO}$) divided by the insulin to carbohydrate ratio (ICR):

$$BOL_M = \frac{CHO}{ICR} \cdot A_{CHO} \quad \text{if } CHO > C_{THD} \tag{Eqn. 18}$$

Continuing this example, if the carbohydrate content is estimated to be less than the same carbohydrate threshold, then the meal bolus calculation may be altered to:

$$BOL_M = \max\left(0, \frac{CHO - C_{THD} * (1 - A_{CHO})}{ICR}.\right) \quad \text{if } CHO \le C_{THD}. \tag{Eqn. 19}$$

The equation for the meal bolus (Eqn. 19) modifies the reduction of the meal bolus for small meals by the attenuation factor ($A_{CHO}$) so that magnitude of the bolus attenuation for a given $A_{CHO}$ is constant below the carbohydrate threshold. In Eqn. 19, the magnitude of the bolus attenuation proportional to the carbohydrate content of the meal above the carbohydrate threshold and proportional to the carbohydrate threshold for smaller meals below the same carbohydrate threshold. In some embodiments, the carbohydrate threshold is 70 grams, although other suitable thresholds may be provided.

The attenuation factor, $A_{CHO}$, is a function of the physiological glucose and the rate of change of physiological glucose. The attenuation factor increases with both increases in physiological glucose and increasing rates of change of the physiological glucose. The attenuation factor may be bound by a lower value and an upper value. In some embodiments, lower limit of the attenuation factor is 0.8. In some embodiments, the upper limit on the attenuation factor is 1.0. In some embodiments, the attenuation factor can be determined from a spline fit of PG and dPG/dt to the values in Table I.

TABLE I

| attenuation factor values | | | |
|---|---|---|---|
| | dPG/dt = −3 mmol/L hr | dPG/dt = 0 mmol/L hr | dPG/dt = 3 mmol/L hr |
| PG = 4.0 mmol/L | 0.8 | 0.9 | 0.9 |
| PG = 6.5 mmol/L | 0.8 | 1.0 | 1.0 |
| PG = 9.0 mmol/L | 1.0 | 1.0 | 1.0 |

In some embodiments, the controller 24 may determine the attenuation factor from a set of linear interpolations for physiological glucose (PG) values and rate of change of physiological glucose (dPG/dt) values. The physiological glucose is may be the estimated physiological glucose (PG) determined by the CGM and/or from the selected-state vector (block 126 in FIG. 3). The rate of change of physiological glucose (dPG/dt) may be determined in several fashions. In some embodiments the rate of change of PG is 60*(PG(t)−PG(t−dt))/dt where dt is 20 mins and dPG/dt has units of mMol/L/hr.

In the example, the meal attenuation (Am)) ranges from 1.0 to 0.8 with the lower attenuation values resulting when physiological glucose concentration is both low (e.g., below 6.5 mmol/L) and decreasing with time.

Referring now to FIG. 10, the attenuated meal bolus ($BOL_M$) from block 708 may be limited by in block 712 based on the total daily dose of insulin (TDD). In some embodiments, the meal bolus is limited to being equal to or less than a predetermined upper limit. If the meal bolus is greater than the predetermined upper limit, the meal bolus is set equal to the predetermined upper limit. In some embodiments, the upper limit is fraction of the TDD. In one embodiment, the upper limit is one fifth of TDD. The resulting limited meal bolus from block 712 is then passed to block 714.

In addition to the meal bolus ($BOL_M$) determined in block 708, a correction bolus ($BOL_C$) is determined in block 710 based on the estimated physiological glucose determined in block 704 as described above. In some embodiments, the correction bolus is also based on the insulin-on-board (IOB) or active insulin in the model. The IOB is the sum of the insulin state variables of the selected-state vector at the current time. The insulin state variables represent the amount or concentration of insulin in the insulin compartments of the model. In some embodiment represented in FIG. 5 and Eqn. 1, the insulin compartments include the two subcutaneous compartments ($I_{S1}$, $I_{S1}$) and the bolus compartments ($I_{B1}$, $I_{B1}$). In some embodiments, the insulin in the various compartments of the model represents the sum of insulin boluses over time plus the basal deviations over time less the insulin transported or converted in the blood compartment 220. In one embodiment, the model and the IOB do not include basal profile insulin or basal dose insulin when these are assumed to compensate for the endogenous glucose production that, in this embodiment, is also not included in the model. In some embodiments, the correction bolus is added to the limited meal bolus in block 714 and the resulting bolus is requested from the insulin delivery device 12. In other embodiments, a request for the limited meal bolus is passed to the pump 12 independently from the request for the correction bolus.

The correction bolus ($Bol_C$) varies the based on estimated physiological glucose value (PG) and the estimated insulin on board (IOB). Illustratively, the correction bolus is zero for PG values below a low PG threshold and increases with PG above the low PG threshold. The rate of increase in the value of the bolus correction with PG is reduced above a high PG threshold.

Figure 11:
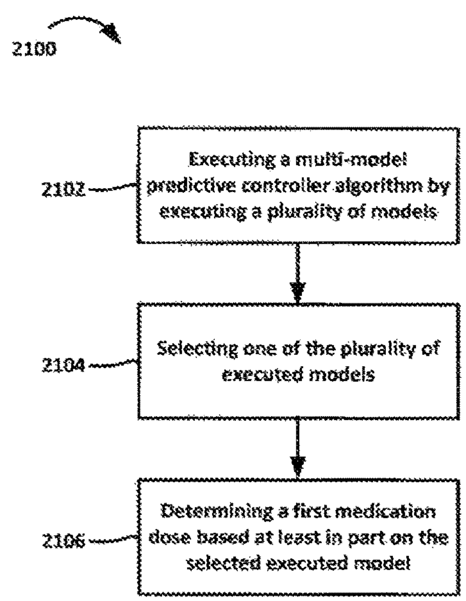
FIGS. 11-28 show exemplary flowcharts of methods that can be carried out with the system to control glucose in a patient.

FIGS. 11-28 show exemplary flowcharts of methods that can be carried out with the system 10 to control glucose in a patient. A method 2100 of FIG. 11 includes executing, using one or more controllers, a multi-model predictive controller algorithm by executing a plurality of models each of which comprise a plurality of model parameters having a set of values (step 2102); selecting, using the one or more controllers, one of the plurality of executed models (step 2104); and determining, using the one or more controllers, a first medication dose based at least in part on the selected executed model (step 2106).

Figure 12:
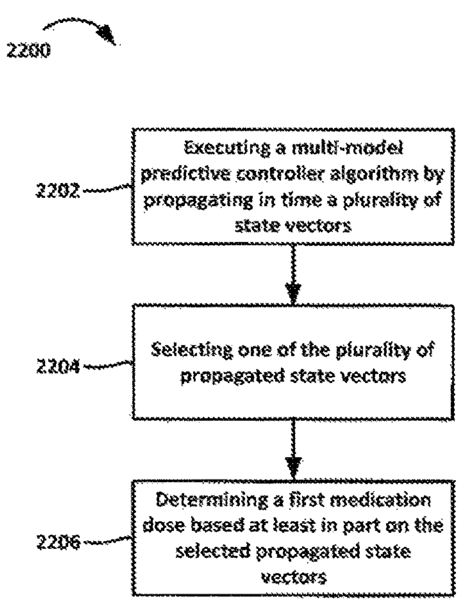

A method 2200 of FIG. 12 includes executing, using one or more controllers, a multi-model predictive controller algorithm by propagating in time a plurality of state vectors (step 2202); selecting, using the one or more controllers, one of the plurality of propagated state vectors (step 2204); and determining, using the one or more controllers, a first medication dose based at least in part on the selected propagated state vector (step 2206).

Figure 13:
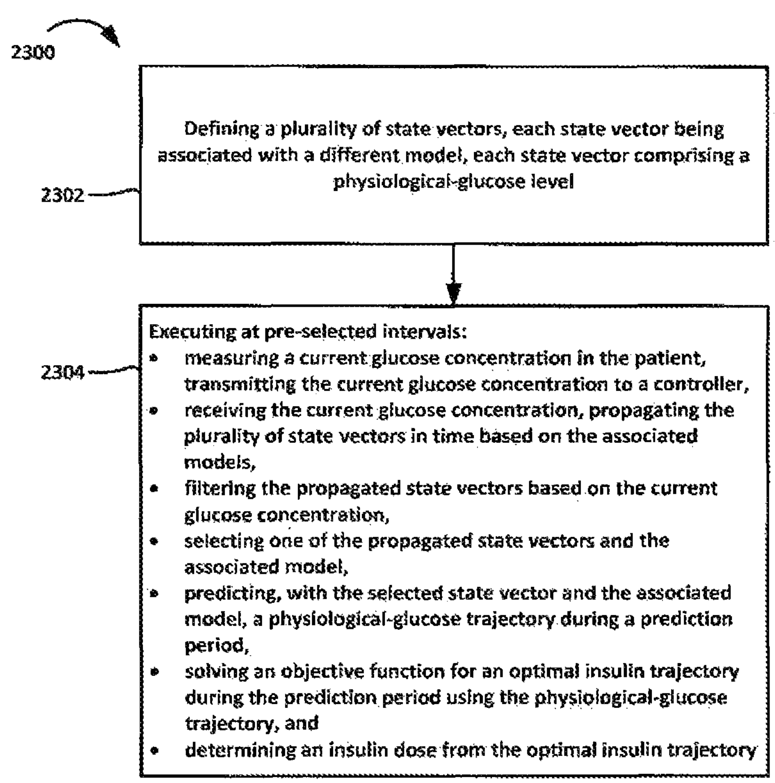

A method 2300 of FIG. 13 includes defining a plurality of state vectors, each state vector being associated with a different model, each state vector comprising a physiological-glucose level (step 2302) and executing the following at pre-selected intervals: measuring a current glucose concentration in the patient, transmitting the current glucose concentration to a controller, receiving the current glucose concentration, propagating the plurality of state vectors in time based on the associated models, filtering the propagated state vectors based on the current glucose concentration, selecting one of the propagated state vectors and the associated model, predicting, with the selected state vector and the associated model, a physiological-glucose trajectory during a prediction period, solving an objective function for an optimal insulin trajectory during the prediction period using the physiological-glucose trajectory, and determining an insulin dose from the optimal insulin trajectory (step 2304).

Figure 14:
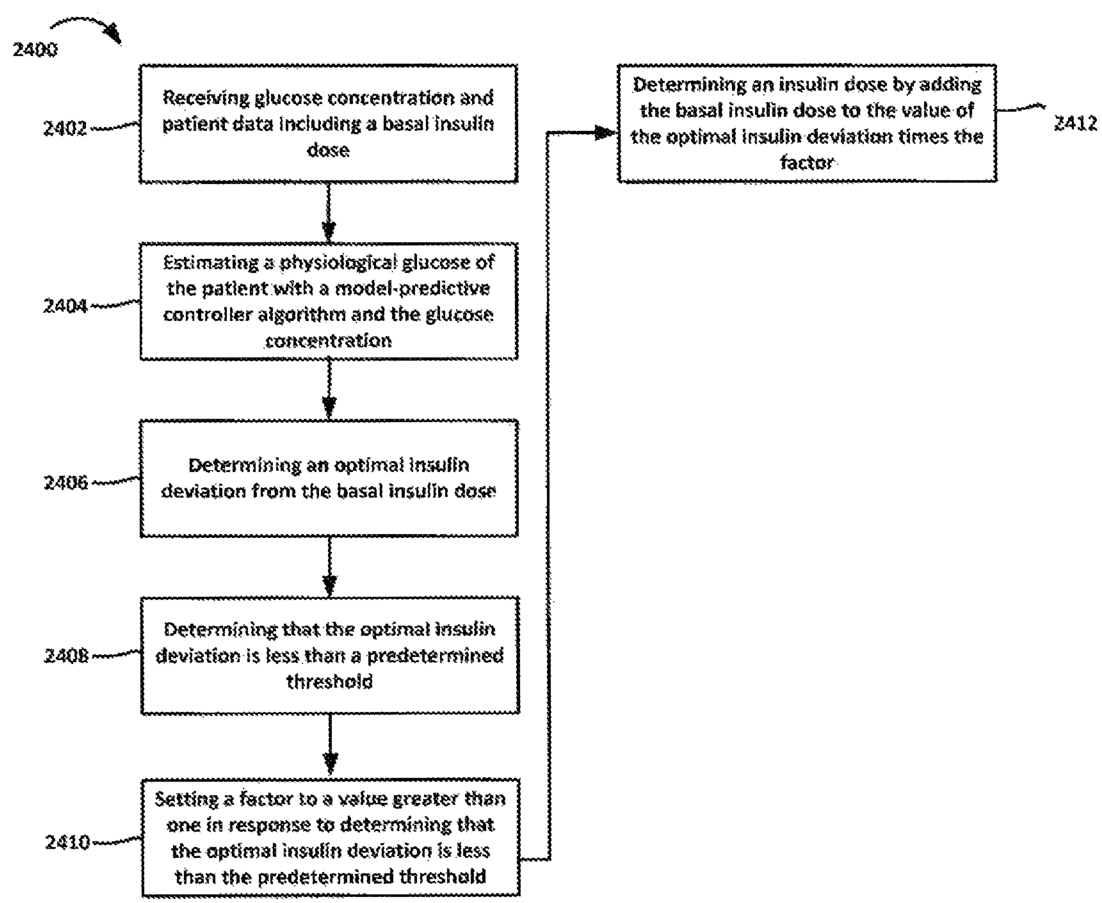

A method 2400 of FIG. 14 includes receiving, at a controller, glucose concentration and patient data including a basal insulin dose (step 2402); estimating a physiological glucose of the patient based at least in part on the glucose concentration (step 2404); determining an optimal insulin deviation from the basal insulin dose (step 2406); determining that the optimal insulin deviation is less than a predetermined threshold (step 2408); setting a factor to a value greater than one in response to determining that the optimal insulin deviation is less than the predetermined threshold (step 2410); and determining an insulin dose by adding the basal insulin dose to the value of the optimal insulin deviation times the factor (step 2412).

Figure 15:
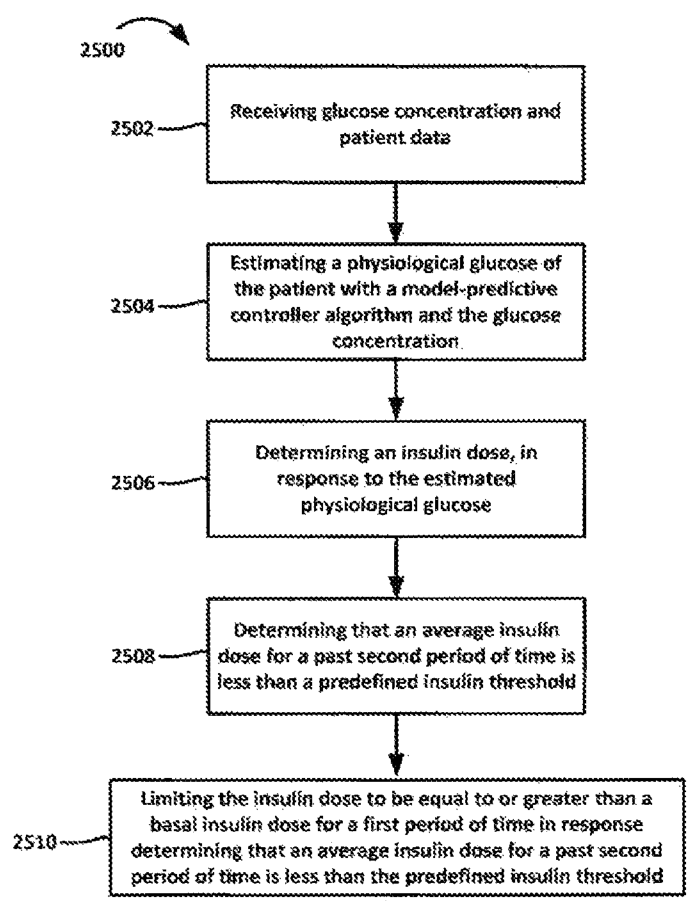

A method 2500 of FIG. 15 includes receiving, at a controller, a glucose concentration and patient data (step 2502); estimating a physiological glucose of the patient based at least in part on the glucose concentration (step 2504); determining an insulin dose, in response to the estimated physiological glucose (step 2506); determining that an average insulin dose for a past second period of time is less than a predefined insulin threshold (step 2508); and limiting the insulin dose to be equal to or greater than a basal insulin dose for a first period of time in response determining that an average insulin dose for a past second period of time is less than the predefined insulin threshold (step 2510).

Figure 16:
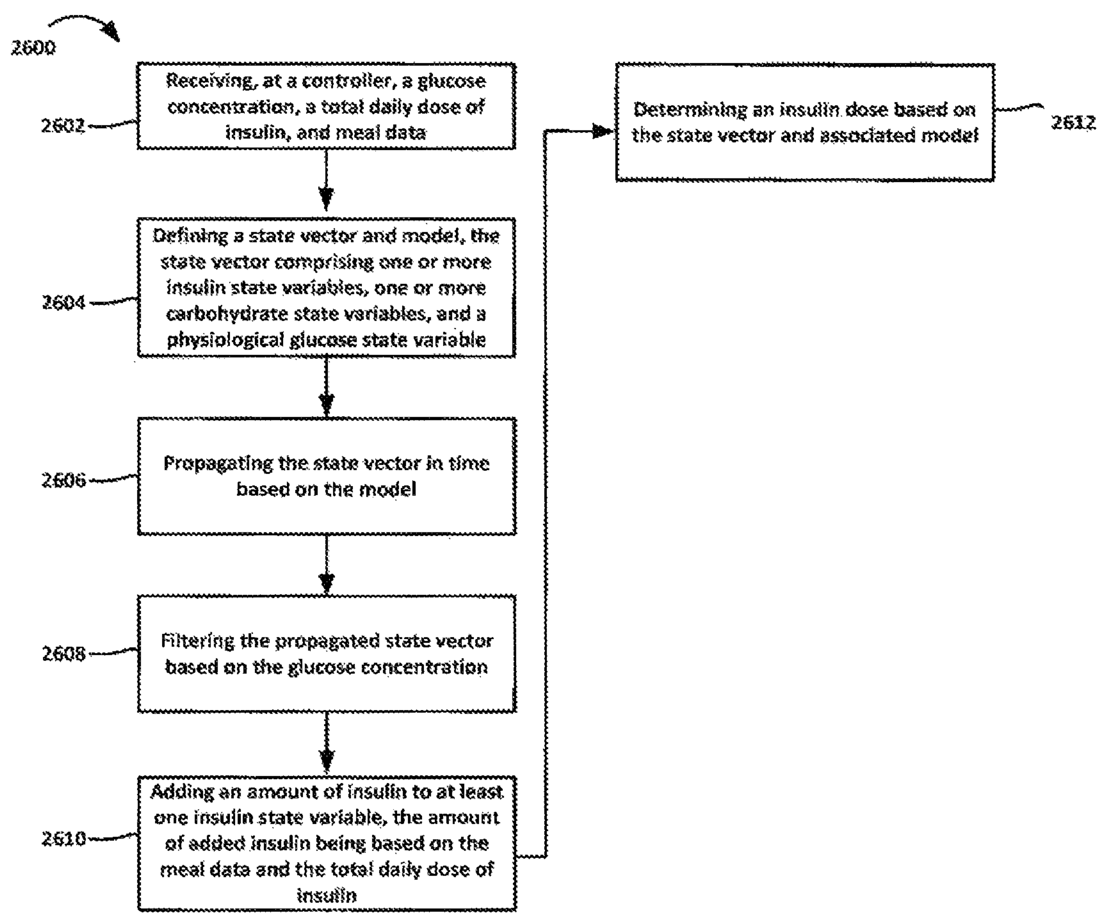

A method 2600 of FIG. 16 includes receiving, at a controller, a glucose concentration, a total daily dose of insulin, and meal data (step 2602); defining a state vector and model, the state vector comprising one or more insulin state variables, one or more carbohydrate state variables, and a physiological glucose state variable (step 2604); propagating the state vector in time based on the model (step 2606); filtering the propagated state vector based on the glucose concentration (step 2608); adding an amount of insulin to at least one insulin state variable, the amount of added insulin being based on the meal data and the total daily dose of insulin (step 2610); and determining an insulin dose based on the state vector and associated model (step 2612).

Figure 17:
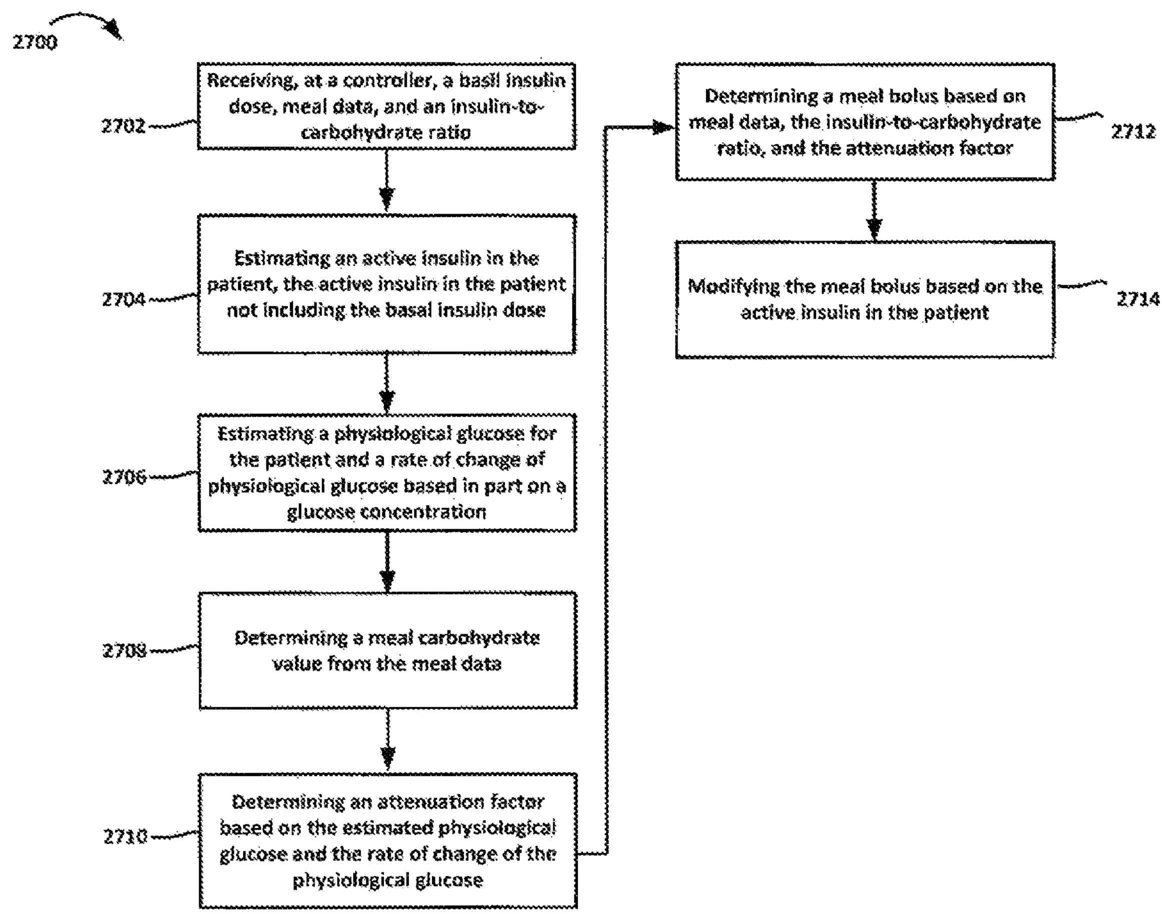

A method 2700 of FIG. 17 includes receiving, at a controller, a basal insulin dose, meal data, and an insulin-to-carbohydrate ratio (step 2702); estimating an active insulin in the patient, the active insulin in the patient not including the basal insulin dose (step 2704); estimating a physiological glucose for the patient and a rate of change of physiological glucose based in part on a glucose concentration (step 2706); determining a meal carbohydrate value from the meal data (step 2708); determining an attenuation factor based on the estimated physiological glucose and the rate of change of the physiological glucose (step 2710); determining a meal bolus based on meal data, the insulin-to-carbohydrate ratio, and the attenuation factor (step 2712); and modifying the meal bolus based on the active insulin in the patient (step 2714).

Figure 18:
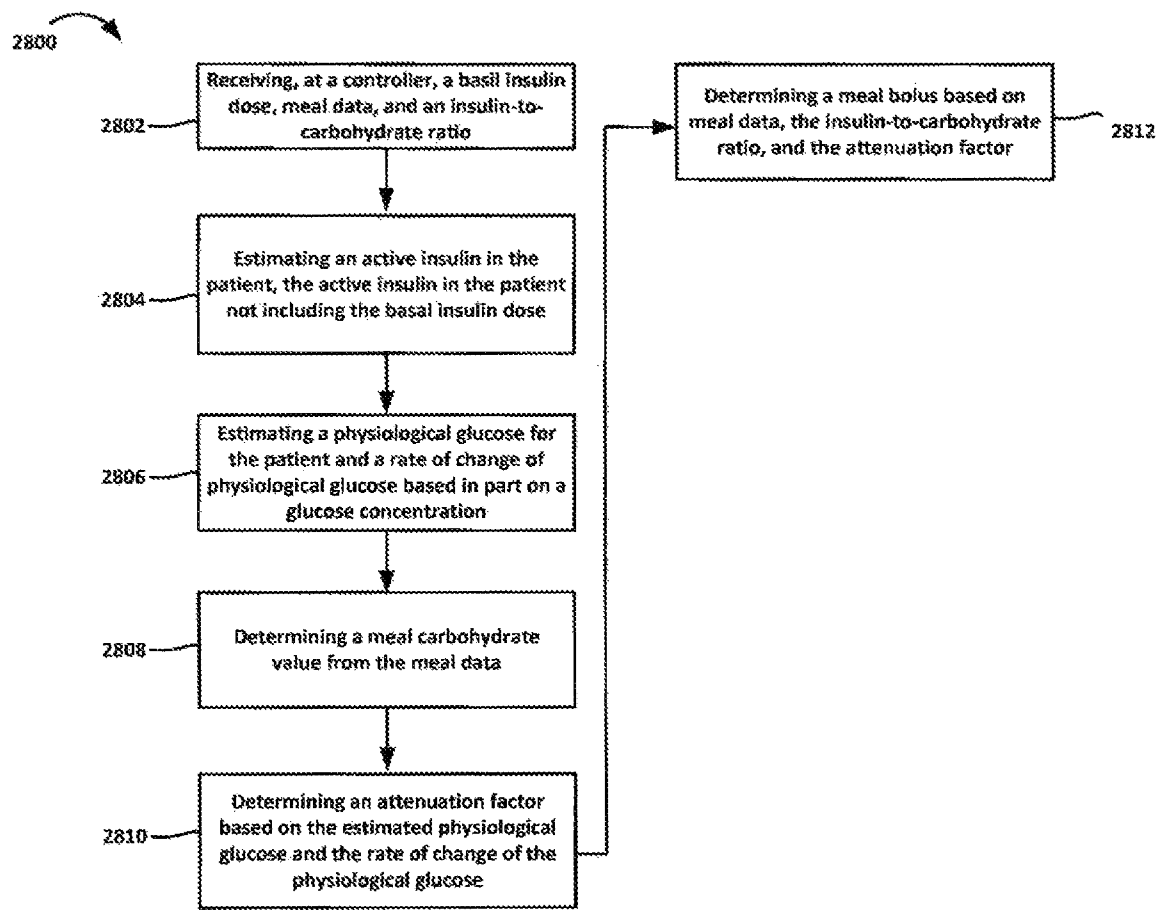

A method 2800 of FIG. 18 includes transmitting a glucose concentration, a basal insulin dose, and a meal data to a controller (step 2802); estimating an active insulin in the patient, the active insulin in the patient not including the basal insulin dose (step 2804); estimating a physiological glucose for the patient and a rate of change of physiological glucose based in part on the glucose concentration (step 2806); determining a meal carbohydrate value from the meal data (step 2808); determining an attenuation factor based on the estimated physiological glucose and rate of change of the physiological glucose (step 2810); determining a meal bolus based on the meal data, an insulin-to-carbohydrate ratio, and the attenuation factor (step 2812), wherein the meal bolus is attenuated proportionally to a meal-carbohydrate value when the meal-carbohydrate value is above a predetermined meal-carbohydrate threshold, and wherein the meal bolus is attenuated proportionally to the predetermined meal-carbohydrate threshold for a meal-carbohydrate value equal to or less than the predetermined meal-carbohydrate threshold.

Figure 19:
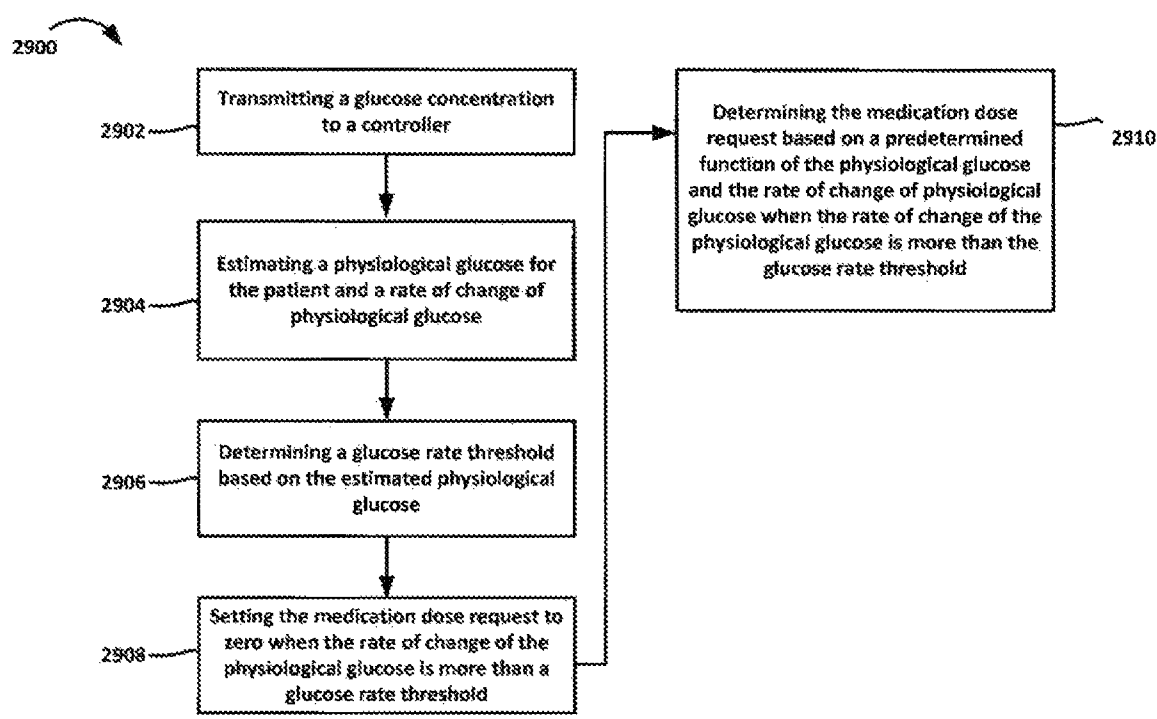

A method 2900 of FIG. 19 includes transmitting a glucose concentration to a controller (step 2902); estimating a physiological glucose for the patient and a rate of change of physiological glucose (step 2904); determining a glucose rate threshold based on the estimated physiological glucose (step 2906); setting the medication dose request to zero when the rate of change of the physiological glucose is more than a glucose rate threshold (step 2908); and determining the medication dose request based on a predetermined function of the physiological glucose and the rate of change of physiological glucose when the rate of change of the physiological glucose is more than the glucose rate threshold (step 2910).

Figure 20:
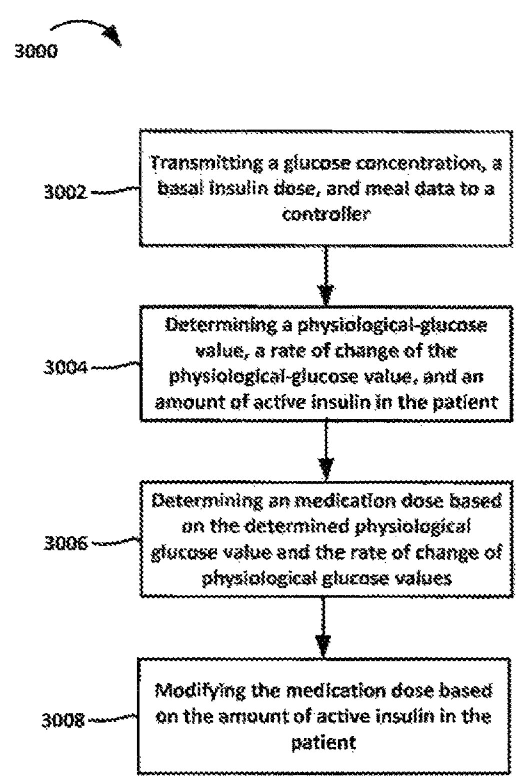

A method 3000 of FIG. 20 includes transmitting a glucose concentration, a basal insulin dose, and meal data to a controller (step 3002); determining a physiological-glucose value, a rate of change of the physiological-glucose value, and an amount of active insulin in the patient, the active insulin in the patient not including the basal insulin profile (step 3004); determining an medication dose based on the determined physiological glucose value and the rate of change of physiological glucose values (step 3006); and modifying the medication dose based on the amount of active insulin in the patient (step 3008).

Figure 21:
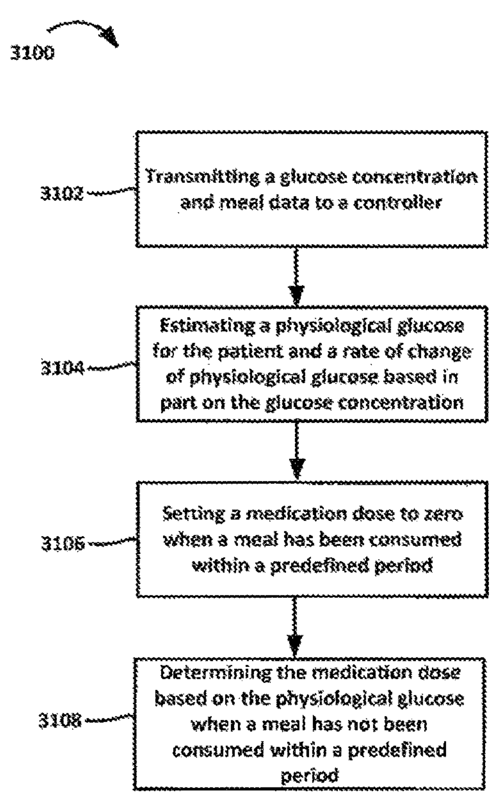

A method 3100 of FIG. 21 includes transmitting a glucose concentration and meal data to a controller (step 3102); estimating a physiological glucose for the patient and a rate of change of physiological glucose based in part on the glucose concentration (step 3104); setting a medication dose to zero when a meal has been consumed within a predefined period (step 3106); and determining the medication dose based on the physiological glucose when a meal has not been consumed within a predefined period (step 3108).

Figure 22:
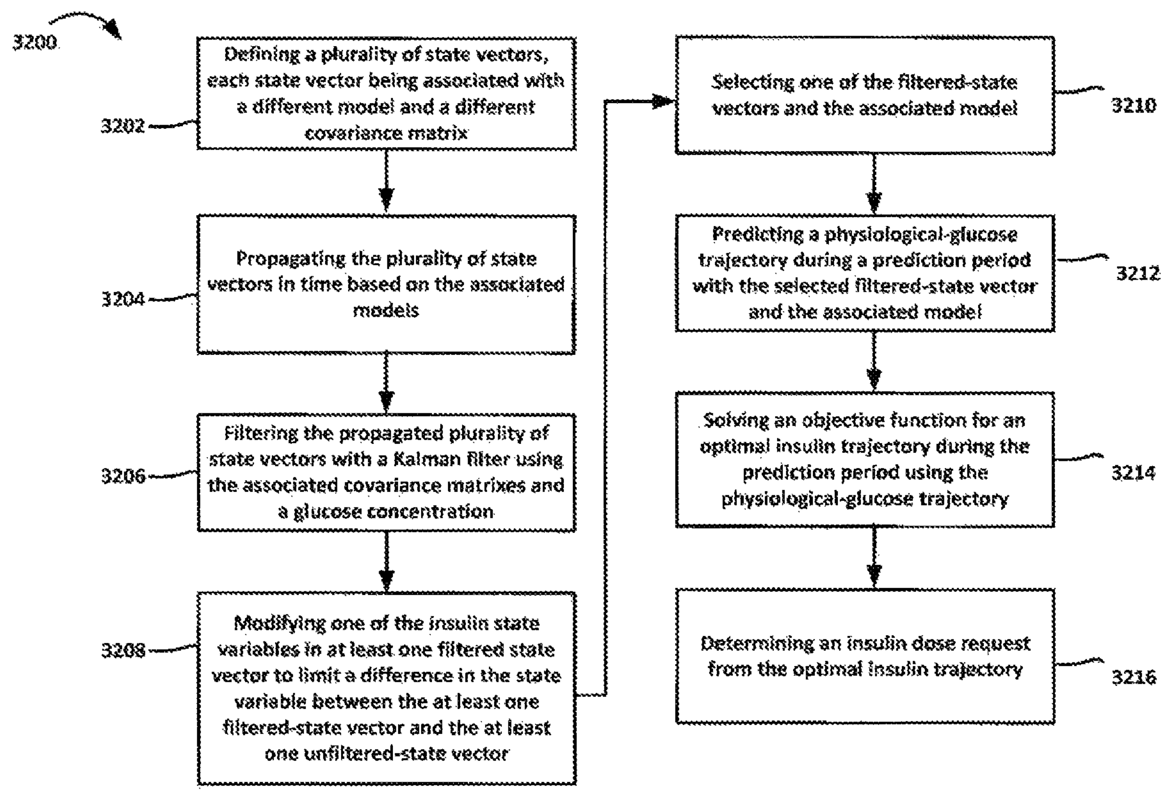

A method 3200 of FIG. 22 includes defining a plurality of state vectors, each state vector being associated with a different model and a different covariance matrix, the plurality of state vectors comprising one or more insulin state variables, one or more carbohydrate state variables, and a physiological glucose state variable (step 3202); propagating the plurality of state vectors in time based on the associated models (step 3204); filtering the propagated plurality of state vectors with a Kalman filter using the associated covariance matrixes and a glucose concentration (step 3206); modifying one of the insulin state variables in at least one filtered state vector to limit a difference in the state variable between the at least one filtered-state vector and the at least one unfiltered-state vector (step 3208); selecting one of the filtered-state vectors and the associated model (step 3210); predicting a physiological-glucose trajectory during a prediction period with the selected filtered-state vector and the associated model (step 3212); solving an objective function for an optimal insulin trajectory during the prediction period using the physiological-glucose trajectory (step 3214); and determining an insulin dose request from the optimal insulin trajectory (step 3216).

Figure 23:
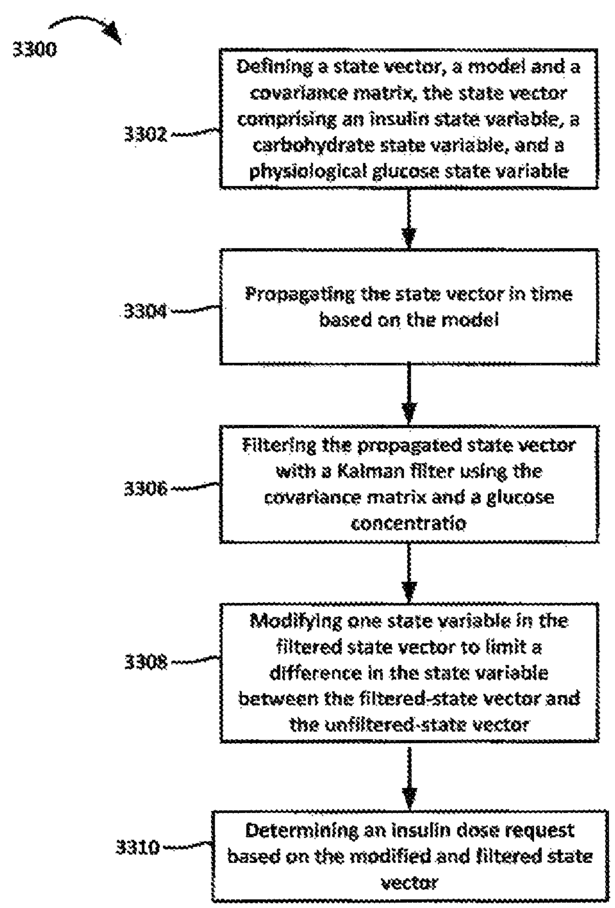

A method 3300 of FIG. 23 includes defining a state vector, a model and a covariance matrix, the state vector comprising an insulin state variable, a carbohydrate state variable, and a physiological glucose state variable (step 3302); propagating the state vector in time based on the model (step 3304); filtering the propagated state vector with a Kalman filter using the covariance matrix and a glucose concentration (step 3306); modifying one state variable in the filtered state vector to limit a difference in the state variable between the filtered-state vector and the unfiltered-state vector (step 3308); and determining an insulin dose request based on the modified and filtered state vector (step 3310).

Figure 24:
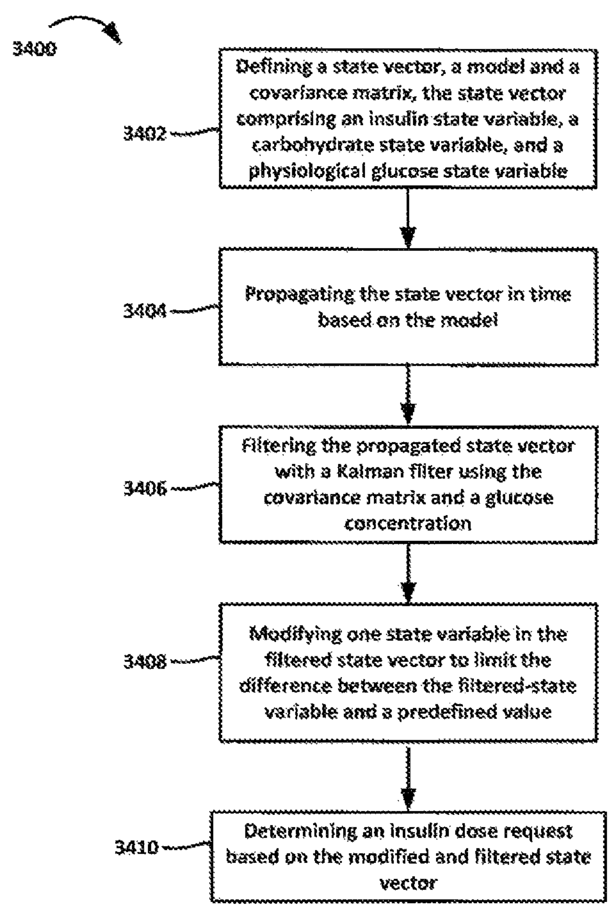

A method 3400 of FIG. 24 includes defining a state vector, a model and a covariance matrix, the state vector comprising an insulin state variable, a carbohydrate state variable, and a physiological glucose state variable (step 3402); propagating the state vector in time based on the model (step 3404); filtering the propagated state vector with a Kalman filter using the covariance matrix and a glucose concentration (step 3406); modifying one state variable in the filtered state vector to limit the difference between the filtered-state variable and a predefined value (step 3408); and determining an insulin dose request based on the modified and filtered state vector (step 3410).

Figure 25:
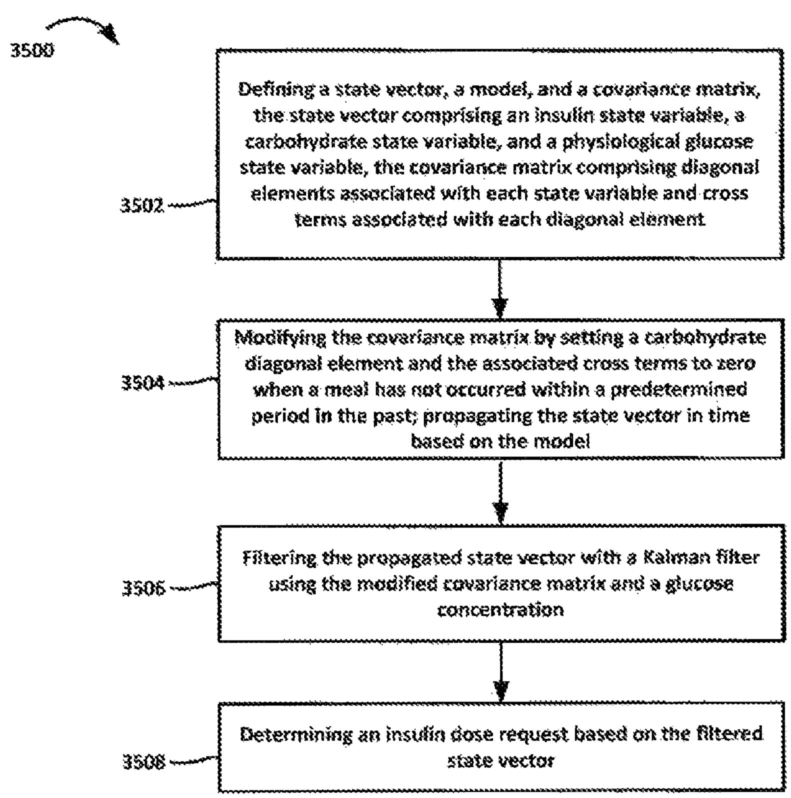

A method 3500 of FIG. 25 includes defining a state vector, a model, and a covariance matrix, the state vector comprising an insulin state variable, a carbohydrate state variable, and a physiological glucose state variable, the covariance matrix comprising diagonal elements associated with each state variable and cross terms associated with each diagonal element (step 3502); modifying the covariance matrix by setting a carbohydrate diagonal element and the associated cross terms to zero when a meal has not occurred within a predetermined period in the past; propagating the state vector in time based on the model (step 3504); filtering the propagated state vector with a Kalman filter using the modified covariance matrix and a glucose concentration (step 3506); and determining an insulin dose request based on the filtered state vector (step 3508).

Figure 26:
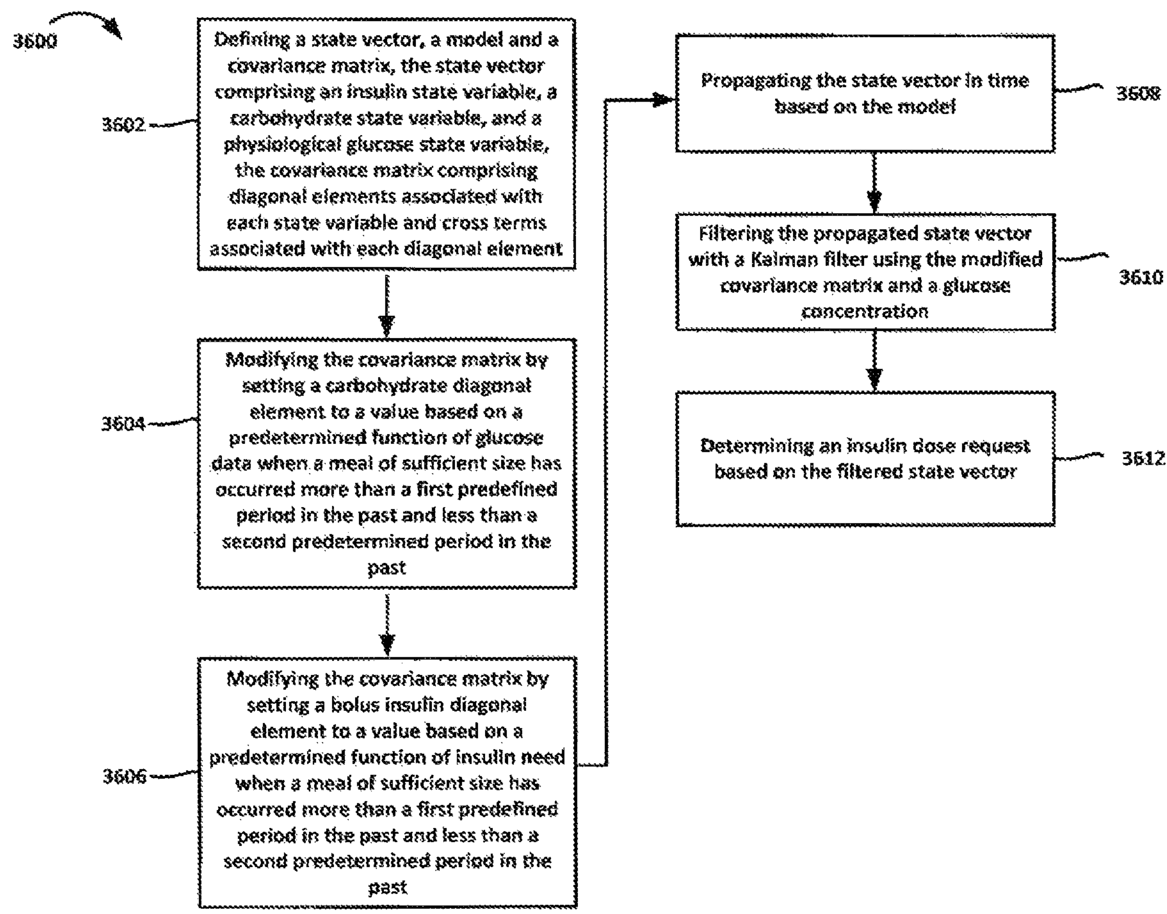

A method 3600 of FIG. 26 includes defining a state vector, a model and a covariance matrix, the state vector comprising an insulin state variable, a carbohydrate state variable, and a physiological glucose state variable, the covariance matrix comprising diagonal elements associated with each state variable and cross terms associated with each diagonal element (step 3602); modifying the covariance matrix by setting a carbohydrate diagonal element to a non-zero value when a sum of carbohydrates exceeds a threshold and an average meal time is between a low threshold and a high threshold (step 3604); modifying the covariance matrix by setting a bolus insulin diagonal element to a non-zero value when a sum of carbohydrates exceeds a threshold and an average meal time is between a low threshold and a high threshold (step 3606); propagating the state vector in time based on the model (step 3608); filtering the propagated state vector with a Kalman filter using the modified covariance matrix and a glucose concentration (step 3610); and determining an insulin dose request based on the filtered state vector (step 3612).

Figure 27:
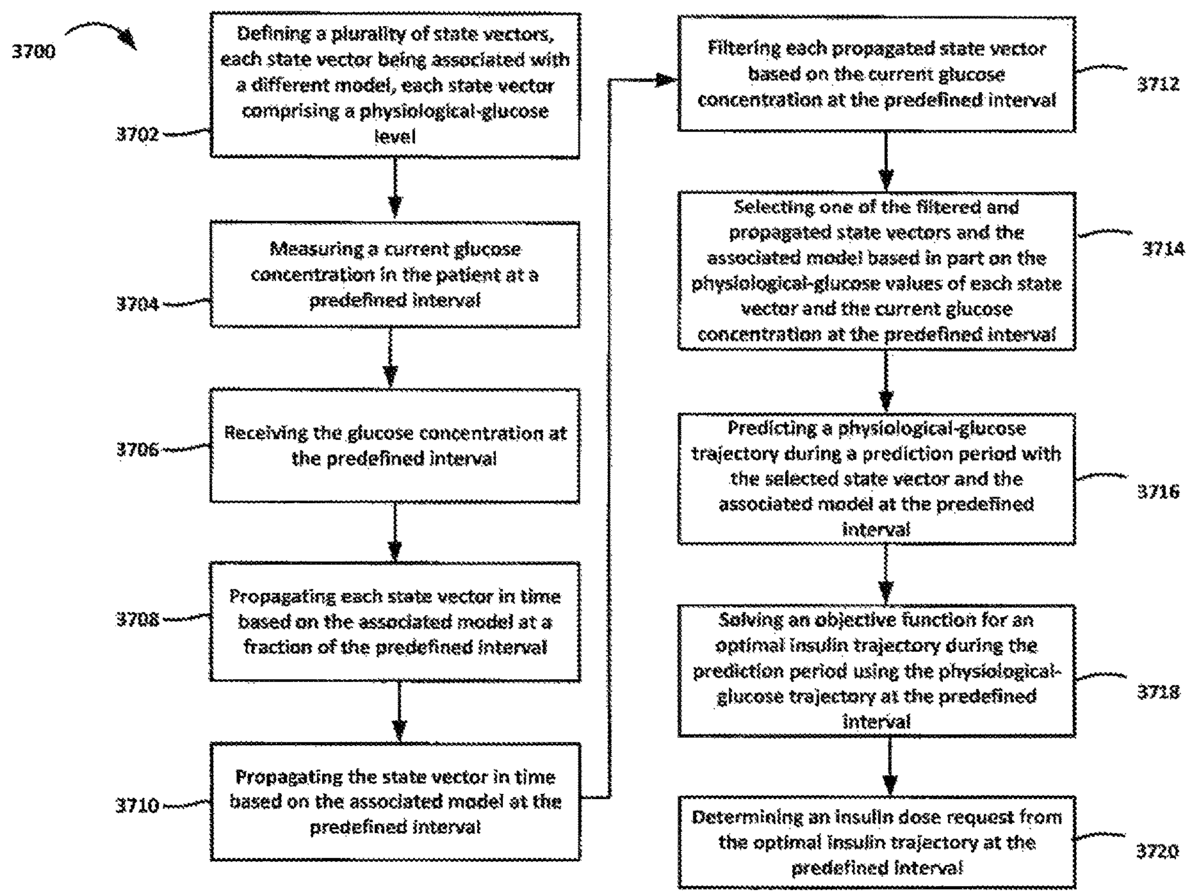

A method 3700 of FIG. 27 includes defining a plurality of state vectors, each state vector being associated with a different model, each state vector comprising a physiological-glucose level (step 3702); measuring a current glucose concentration in the patient at a predefined interval (step 3704); receiving the glucose concentration at the predefined interval (step 3706); propagating each state vector in time based on the associated model at a fraction of the predefined interval (step 3708); propagating the state vector in time based on the associated model at the predefined interval (step 3710); filtering each propagated state vector based on the current glucose concentration at the predefined interval (step 3712); selecting one of the filtered and propagated state vectors and the associated model based in part on the physiological-glucose values of each state vector and the current glucose concentration at the predefined interval (step 3714); predicting a physiological-glucose trajectory during a prediction period with the selected state vector and the associated model at the predefined interval (step 3716); solving an objective function for an optimal insulin trajectory during the prediction period using the physiological-glucose trajectory at the predefined interval (step 3718); and determining an insulin dose request from the optimal insulin trajectory at the predefined interval (step 3720).

Figure 28:
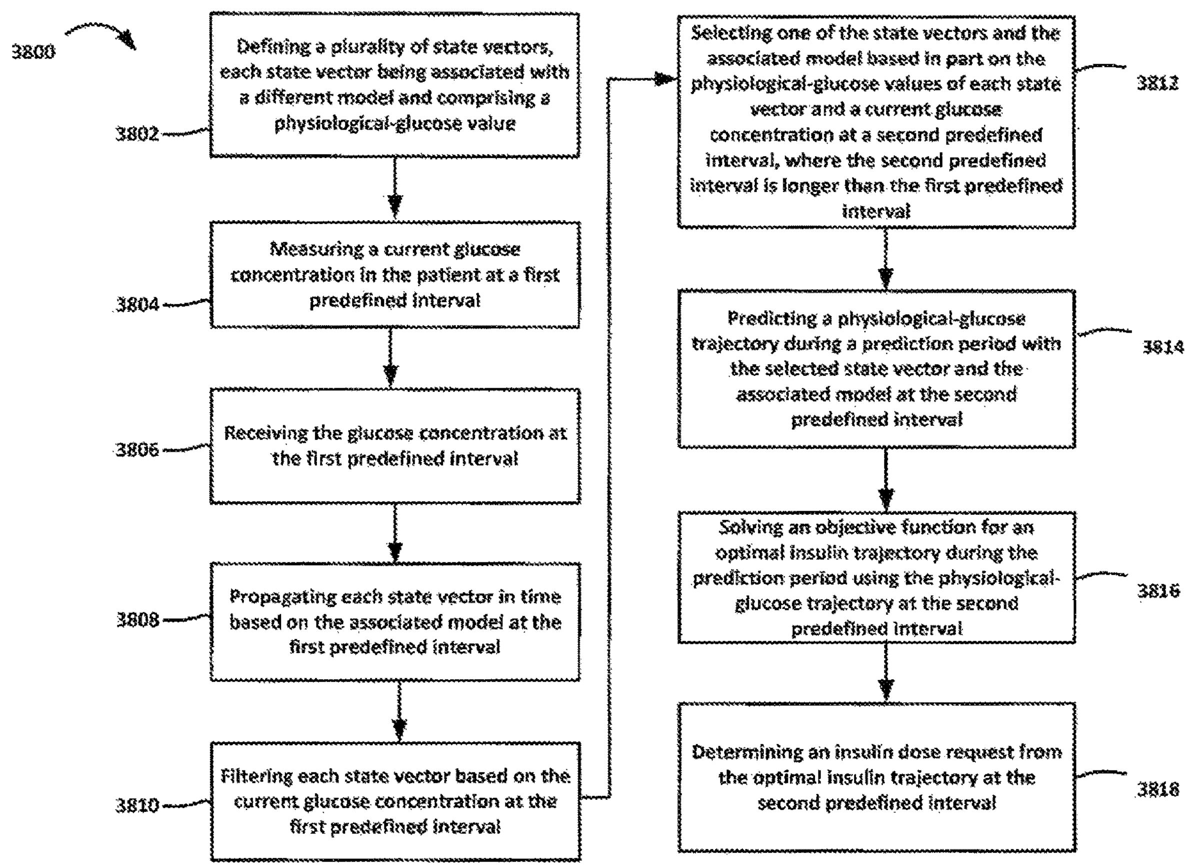

A method 3800 of FIG. 28 includes defining a plurality of state vectors, each state vector being associated with a different model and comprising a physiological-glucose value (step 3802); measuring a current glucose concentration in the patient at a first predefined interval (step 3804); receiving the glucose concentration at the first predefined interval (step 3806); propagating each state vector in time based on the associated model at the first predefined interval (step 3808); filtering each state vector based on the current glucose concentration at the first predefined interval (step 3810); selecting one of the state vectors and the associated model based in part on the physiological-glucose values of each state vector and a current glucose concentration at a second predefined interval, where the second predefined interval is longer than the first predefined interval (step 3812); predicting a physiological-glucose trajectory during a prediction period with the selected state vector and the associated model at the second predefined interval (step 3814); solving an objective function for an optimal insulin trajectory during the prediction period using the physiological-glucose trajectory at the second predefined interval (step 3816); and determining an insulin dose request from the optimal insulin trajectory at the second predefined interval (step 3818).

Exemplary aspects of the present disclosure include the following:

1. A system to control glucose in a patient, the system comprising:
- a medication delivery device configured to deliver a medication dose to the patient; and
- a controller operably coupled to the medication delivery device and including control logic operative to:
  - execute a multi-model predictive controller algorithm at least in part by executing a plurality of models each comprising a plurality of model parameters having a set of values,
  - select one of the plurality of executed models, and
  - determine a first medication dose based at least in part on the selected executed model.

2. The system of aspect 1, wherein the control logic is further operative to:
- predict future glucose levels of the patient based at least in part on the selected executed model, wherein the determination of the first medication dose is based at least in part on the predicted future glucose levels.

3. The system of aspect 2, wherein the control logic is further operative to:
- determine a difference between the predicted future glucose levels and a nominal target glucose value, wherein the determination of the first medication dose is based at least in part on the difference between the predicted future glucose levels and the nominal target glucose value.

4. The system of any of aspects 2 and 3, wherein the prediction of future glucose levels is based at least in part on a basal insulin profile.

5. The system of any of aspects 2 and 3, wherein the prediction of future glucose levels is based at least in part on a basal insulin profile and without meal boluses.

6. The system of aspect 1, wherein the control logic being operative to select one of the plurality of executed models comprises the control logic being operative to:
- select one of the plurality of executed models in response to comparing a calculated level of interstitial glucose and a measured level of interstitial glucose.

7. The system of aspect 6, wherein the measured level of interstitial glucose comprises a plurality of past measured levels of interstitial glucose.

8. The system of aspect 1, wherein the control logic being operative to select one of the plurality of executed models comprises the control logic being operative to:

select one of the plurality of executed models based at least in part on a nominal target glucose value.

9. The system of aspect 8, wherein the nominal target glucose value is increased in response to an exercise announcement.

10. The system of aspect 8, wherein the nominal target glucose value is increased in response to a meal announcement.

11. The system of aspect 1, wherein the control logic is further operative to:

re-execute the multi-model predictive controller algorithm, select a different one of the plurality of executed models, and determine a second medication dose based at least in part on the selected executed model.

12. The system of aspect 1, wherein the control logic is further operative to:

re-execute the multi-model predictive controller algorithm including re-executing the plurality of models using the plurality of model parameters and the set of values, select a different one of the plurality of executed models, and determine a second medication dose based at least in part on the selected executed model.

13. The system of aspect 1, wherein the plurality of model parameters includes at least one of an insulin sensitivity, an insulin time constant, a meal action time constant, a sensor time constant, an insulin-to-carbohydrate ratio, an input from a user interface, and a controller gain value.

14. The system of aspect 1, wherein the plurality of model parameters includes an insulin sensitivity, an insulin time constant, a meal action time constant, a sensor time constant, and an insulin-to-carbohydrate ratio.

15. The system of aspect 1, wherein each of the plurality of models includes a set of linear differential equations that calculate levels of physiological glucose and interstitial glucose.

16. The system of aspect 15, wherein the set of linear differential equations model storage and transportation of insulin in the patient.

17. The system of any of aspects 1-16, wherein the medication delivery device is configured to deliver insulin to the patient based at least in part on the determined first and/or second medication dose.

18. The system of any of aspects 1-17, further comprising:

a user interface operably coupled to the controller and configured to receive input from the patient.

19. The system of any of aspects 1-18, further comprising:

a glucose measurement device operably coupled to the controller and configured to measure glucose data associated with the patient, wherein the determination of the first medication dose is based at least in part on the measured glucose data.

20. A method to control glucose in a patient, the method comprising:

executing, using one or more controllers, a multi-model predictive controller algorithm by executing a plurality of models each of which comprise a plurality of model parameters having a set of values;

selecting, using the one or more controllers, one of the plurality of executed models; and determining, using the one or more controllers, a first medication dose based at least in part on the selected executed model.

21. The method of aspect 20, further comprising:

predicting, using the one or more controllers, future glucose levels of the patient based at least in part on the selected executed model, wherein the determination of the first medication dose is based at least in part on the predicted future glucose levels.

22. The method of aspect 21, further comprising:

determining, using the one or more controllers, a difference between the predicted future glucose levels and a nominal target glucose value, wherein the determination of the first medication dose is based at least in part on the difference between the predicted future glucose levels and the nominal target glucose value.

23. The method of any of aspects 21 and 22, wherein the prediction of future glucose levels is based at least in part on a basal insulin profile.

24. The method of any of aspects 21 and 22, wherein the prediction of future glucose levels is based at least in part on a basal insulin profile and without meal boluses.

25. The method of aspect 20, further comprising:

re-executing the multi-model predictive controller algorithm;

selecting a different one of the plurality of executed models; and determining a second medication dose based at least in part on the selected executed model.

26. The method of aspect 20, further comprising:

re-executing the multi-model predictive controller algorithm including re-executing the plurality of models using the plurality of model parameters and the set of values;

selecting a different one of the plurality of executed models; and determining a second medication dose based at least in part on the selected executed model.

27. The method of aspect 20, wherein the plurality of model parameters includes at least one of an insulin sensitivity, an insulin time constant, a meal action time constant, a sensor time constant, an insulin-to-carbohydrate ratio, an input from a user interface, and a controller gain value.

28. The method of aspect 20, wherein the plurality of model parameters includes an insulin sensitivity, an insulin time constant, a meal action time constant, a sensor time constant, and an insulin-to-carbohydrate ratio.

29. The method of aspect 20, wherein executing a plurality of models includes executing a set of linear differential equations to calculate levels of physiological glucose and interstitial glucose.

30. The method of aspect 29, wherein the set of linear differential equations model storage and transportation of insulin in the patient.

31. The method of aspect 20, wherein selecting one of the plurality of executed models is in response to comparing a calculated level of interstitial glucose and a measured level of interstitial glucose.

32. The method of aspect 31, wherein the measured level of interstitial glucose comprises a plurality of past measured levels of interstitial glucose.

33. The method of aspect 20, wherein selecting one of the plurality of executed models is based at least in part on a nominal target glucose value.

34. The method of aspect 33, wherein the nominal target glucose value is increased in response to an exercise announcement.

35. The method of aspect 33, wherein the nominal target glucose value is increased in response to a meal announcement.

36. The method of any of aspects 20-35, further comprising: delivering insulin to the patient, using a medication delivery device, in response to the determined first and/or second medication dose.

37. The method of any of aspects 20-36, further comprising: measuring glucose data associated with the patient using a glucose measurement device operably coupled to the controller, wherein the determination of the first medication dose is based at least in part on the measured glucose data.

38. A system to control glucose in a patient, the system comprising:

a medication delivery device configured to deliver a medication dose to the patient; and a controller operably coupled to the medication delivery device and including control logic operative to:

execute a multi-model predictive controller algorithm by propagating a plurality of state vectors in time, select one of the plurality of propagated state vectors, and determine a first medication dose based at least in part on the selected propagated state vector.

39. The system of aspect 38, wherein the control logic is further operative to:

predict future glucose levels of the patient based at least in part on the selected propagated state vector, wherein the determination of the first medication dose is based at least in part on the predicted future glucose levels.

40. The system of aspect 39, wherein the control logic is further operative to:

determine a difference between the predicted future glucose levels and a nominal target glucose value, wherein the determination of the first medication dose is based at least in part on the difference between the predicted future glucose levels and the nominal target glucose value.

41. The system of any of aspects 39 and 40, wherein the prediction of future glucose levels is based at least in part on a basal insulin profile.

42. The system of any of aspects 39 and 40, wherein the prediction of future glucose levels is based at least in part on a basal insulin profile and without meal boluses.

43. The system of aspect 38, wherein the control logic is operative to:

further propagate, in time, the propagated selected state vector, wherein the first medication dose is determined based at least in part on the further propagated selected state vector.

44. The system of aspect 38, wherein the control logic is operative to:

re-execute the multi-model predictive controller algorithm, select a different one of the plurality of propagated state vectors, and determine a second medication dose based at least in part on the selected propagated state vector.

45. The system of aspect 38, wherein the plurality of model parameters includes at least one of an insulin sensitivity, an insulin time constant, a meal action time constant, a sensor time constant, an insulin-to-carbohydrate ratio, an input from a user interface, and a controller gain value.

46. The system of aspect 38, wherein the plurality of model parameters includes an insulin sensitivity, an insulin time constant, a meal action time constant, a sensor time constant, and an insulin-to-carbohydrate ratio.

47. The system of aspect 38, wherein the plurality of models includes a set of linear differential equations that calculate levels of physiological glucose and interstitial glucose.

48. The system of aspect 47, wherein the set of linear differential equations model storage and transportation of insulin in the patient.

49. The system of aspect 38, wherein the control logic being operative to select one of the plurality of propagated state vectors comprises the control logic being operative to:

select one of the plurality of propagated state vectors in response to comparing a calculated level of interstitial glucose and a measured level of interstitial glucose.

50. The system of aspect 49, wherein the measured level of interstitial glucose comprises a plurality of past measured levels of interstitial glucose.

51. The system of aspect 38, wherein the control logic being operative to select one of the plurality of propagated state vectors comprises the control logic being operative to:

select one of the plurality of state vectors based at least in part on a nominal target glucose value.

52. The system of aspect 51, wherein the nominal target glucose value is increased in response to an exercise announcement.

53. The system of aspect 51, wherein the nominal target glucose value is increased in response to a meal announcement.

54. The system of any of aspects 38-53, wherein the medication delivery device is configured to deliver insulin to the patient, in response to the determined first and/or second medication dose.

55. The system of any of aspects 38-54, further comprising:

a user interface operably coupled to the controller and configured to receive input from the patient.

56. The system of any of aspects 38-55, further comprising:

a glucose measurement device operably coupled to the controller and configured to measure glucose data associated with the patient, wherein the determination of the first medication dose is based at least in part on the measured glucose data.

57. A method to control glucose in a patient, the method comprising:

executing, using one or more controllers, a multi-model predictive controller algorithm by propagating in time a plurality of state vectors;

selecting, using the one or more controllers, one of the plurality of propagated state vectors; and determining, using the one or more controllers, a first medication dose based at least in part on the selected propagated state vector.

58. The method of aspect 57, further comprising:

predicting, using the one or more controllers, future glucose levels of the patient based at least in part on the selected propagated state vector, wherein the determination of the first medication dose is based at least in part on the predicted future glucose levels.

59. The method of aspect 58, further comprising:

determining, using the one or more controllers, a difference between the predicted future glucose levels and a nominal target glucose value, wherein the determination of the first medication dose is based at least in part on the difference between the predicted future glucose levels and the nominal target glucose value.

60. The method of any of aspects 58 and 59, wherein the prediction of future glucose levels is based at least in part on a basal insulin profile.

61. The method of any of aspects 58 and 59, wherein the prediction of future glucose levels is based at least in part on a basal insulin profile and without meal boluses.

62. The method of aspect 57, further comprising:
re-executing the multi-model predictive controller algorithm;
selecting a different one of the plurality of propagated state vectors and its associated model; and
determining a second medication dose based at least in part on the selected propagated state vector and its associated model.

63. The method of aspect 57, wherein the plurality of propagated state vectors each include a state variable representing a calculated level of interstitial glucose, and wherein selecting one of the plurality of propagated state vectors and its associated model includes:
selecting one of the plurality of propagated state vectors and its associated model in response to comparing the calculated levels of interstitial glucose and a measured level of interstitial glucose.

64. The method of aspect 63, wherein the measured level of interstitial glucose comprises a plurality of past measured levels of interstitial glucose.

65. The method of aspect 57, wherein selecting one of the plurality of propagated state vectors and its associated model includes:
selecting one of the plurality of state vectors based at least in part on a nominal target glucose value.

66. The method of aspect 65, wherein the nominal target glucose value is increased in response to an exercise announcement.

67. The method of aspect 65, wherein the nominal target glucose value is increased in response to a meal announcement.

68. The method of any of aspects 57-67, further comprising:
delivering insulin to the patient, using a medication delivery device, in response to the determined first and/or second medication dose.

69. The method of any of aspects 57-68, further comprising:
measuring glucose data associated with the patient using a glucose measurement device operably coupled to the controller, wherein the determination of the first medication dose is based at least in part on the measured glucose data.

70. A system to control glycemia in a patient, the system comprising:
an insulin delivery device configured to deliver an insulin dose to the patient; and
a controller including control logic operative to:
receive a current glucose datum at a pre-selected interval,
define a plurality of state vectors, each state vector being associated with a different model, each state vector comprising a body-glucose level,
propagate the plurality of state vectors in time based on the associated models,
filter the propagated state vectors based on the current glucose datum,
select one of the propagated state vectors and its associated model,
predict body-glucose levels during a prediction period with the selected state vector and the associated model,
solve an objective function for an optimal insulin trajectory during the prediction period,
determine the insulin dose from the optimal insulin trajectory, and
transmit a request to deliver the determined insulin dose to the insulin delivery device.

71. The system of aspect 70, further comprising a memory for storing the body-glucose levels, wherein the control logic is further operative to:
store in the memory the body-glucose level for each state vector and the glucose datum,
recall from the memory the body glucose level for each state vector and glucose datum for a plurality of past intervals, and
base the selection of one of the state vector and the associated model on body glucose levels and glucose data recalled from the memory.

72. The system of aspect 70, further comprising a memory for storing the body-glucose levels, wherein the control logic is further operative to:
determine an error of the body-glucose level for each state vector relative to the glucose datum,
store in the memory the body-glucose error,
recall from the memory the body-glucose error of each state vector for a plurality of past intervals, and
base the selection of one of the state vector and the associated model on the sum of the body-glucose errors for each state vector.

73. The system of aspect 70, wherein each state vector is associated with a different covariance matrix, and wherein the propagated state vectors are filtered with a Kalman filter using the associated covariance matrix.

74. The system of aspect 70, wherein the controller is configured to select the state vector and its associated model that has most closely matched the measured glucose data based on a performance function, and wherein the performance function is a sum of weighted difference between physiological glucose and measured glucose.

75. The system of any of aspects 70-74, further comprising a user interface for receiving meal data, wherein the controller is configured to receive the meal data from the user interface, and wherein the controller is configured to select the state vector and its associated model from a reduced set of the state vectors and their associated models for a predefined period of time after a meal.

76. The system of aspect 75, wherein the reduced set of the state vectors and their associated models have an insulin-absorption time less than a predefined threshold.

77. The system of any of aspects 70-74, further comprising a user interface for receiving a user input representative of meal data, wherein the controller is configured to, after receiving the meal data and propagating and filtering the state vectors, correct the state vectors by increasing an amount of insulin to an insulin state variable in each state vector, the amount of added insulin being based on the meal data and an insulin need.

78. The system of any of aspects 70-77, wherein the controller is configured to define a target glucose, and the objective function comprises a sum of weighted differences between a predicted physiological glucose and the target glucose.

79. The system of any of aspects 70-78, further comprising a user interface for generating meal data based on user input and transmitting the generated meal data to the controller, wherein a weighting value increases with time after a meal up to a constant value at times longer than a predetermined period after the meal.

80. The system of any of aspects 70-79, wherein the objective function comprises a sum of the weighted deviations of the optimal insulin trajectory from a predefined basal insulin profile.

81. The system of any of aspects 70-80, wherein the controller is configured to, in determining the optimal insulin trajectory at a given point, limit a maximum value of insulin, the maximum value being a function of a basal dose and an estimated physiological glucose of the patient at the given point.

82. The system of aspect 81, wherein the controller is configured to limit a minimum value of insulin in the optimal insulin trajectory to a predefined value, the predefined value being less than the basal dose.

83. The system of any of aspects 70-80, wherein the controller is configured to, in determining the optimal insulin trajectory at a given point, limit insulin values to be equal to or greater than a basal insulin profile at the given point, when a predicted physiological glucose at the given point is greater than a predefined glucose threshold.

84. The system of aspect 83, wherein the predefined glucose threshold is 13.7 mg/dL.

85. The system of any of aspects 70-80, wherein the controller is configured to, in determining the optimal insulin trajectory, limit an insulin value to be equal to or greater than a basal profile at a given point, when an average predicted physiological glucose is less than a predefined glucose threshold, the average predicted physiological glucose values determined from the optimal insulin trajectory over a predefined number of points before the given point.

86. The system of any of aspects 70-80, wherein the controller is configured to modify a value of the optimal insulin trajectory at a given point, if the value is less than a basal profile at the given time, and wherein the controller is configured to calculate a new optimal insulin value at the given point by adding a quantity of the optimal insulin value minus the basal profile times a factor to the basal profile, the factor being greater than one.

87. The system of any of aspects 70-80, wherein the controller is configured to limit the insulin dose request to be equal to or greater than a basal profile dose when an estimated physiological glucose of the patient is greater than a predefined glucose threshold.

88. The system of aspect 87, wherein the predefined glucose threshold is 13.7 mg/dL.

89. The system of any of aspects 70-80, wherein the controller is configured to limit the insulin dose request to be equal to or greater than a basal profile for a first predefined period after an average physiological glucose is less than a predefined glucose threshold, the average predicted physiological glucose being the average of estimated physiological glucose of the selected state vectors over a second predefined period in the past.

90. The system of any of aspects 70-80, wherein the controller is configured to modify a value of the insulin dose request when the insulin dose request is less than a basal dose, and wherein the controller is configured to calculate a new insulin dose request by adding a quantity of the insulin dose request minus the basal dose times a factor to the basal dose, the factor being greater than one.

91. The system of aspect 70, further comprising a user interface for receiving meal data, the meal data communicated to the controller, wherein each state vector and its associated model are associated with a covariance matrix, wherein diagonal elements of the covariance matrix are initialized as functions of glucose data and insulin need data, and wherein propagating the state vectors further includes a Kalman filter using the covariance matrices and the glucose data to produce filtered-state vectors of filtered-state variables.

92. The system of aspect 91, wherein the controller is configured to, when no meal has been consumed for a predefined period of time, set a diagonal carbohydrate term to a value based on a predetermined function of the glucose data and a total daily dose of insulin and set row and column elements aligned with the carbohydrate diagonal value to zero.

93. The system of aspect 91, wherein the controller is configured to, in response to determining that no meal has been consumed for a predefined period of time, set a bolus insulin diagonal term to a value based on a predetermined function of the glucose data and a total daily dose of insulin and set row and column elements aligned with the bolus insulin diagonal value to zero.

94. The system of aspect 70, wherein each state vector and its model are associated with a covariance matrix, and propagating the state vectors further includes a Kalman filter using the covariance matrices and glucose data to produce filtered-state vectors of filtered-state variables, and wherein the controller is configured to modify one of the filtered-state variables based on the values of that filtered-state variable.

95. The system of aspect 94, wherein the controller is configured to modify a filtered-state variable to be greater than or equal to a predetermined amount.

96. The system of aspect 94, wherein the controller is configured to modify a filtered-state variable for insulin to be greater than or equal to a predetermined fraction of a basal dose.

97. The system of aspect 94, wherein the controller is configured to modify a filtered-state variable for carbohydrates to be greater than or equal to a predetermined value less than the unfiltered-state variable for carbohydrate.

98. The system of aspect 94, wherein the controller is configured to modify a filtered-state variable for insulin to be less than or equal to a predetermined amount more than the unfiltered-state variable for insulin.

99. The system of any of aspects 70-98, further comprising:
- a glucose measurement device in communication with the controller and for measuring glucose data in the patient.

100. A system to control glycemia in a patient, the system comprising:
- a controller configured to:
  - receive patient data including a basal dose,
  - receive glucose data at intervals,
  - execute a model-predictive controller algorithm to estimate physiological glucose based in part on the received glucose data, and
  - limit a dose request to be equal to or greater than the basal dose when the physiological glucose exceeds a predetermined glucose threshold.

101. The system of aspect 100, wherein the predetermined glucose threshold is 13.7 mg/dL.

102. The system of aspect 100, further comprising:
- an insulin delivery device for delivering insulin to the patient, in response to the dose request; and
- a user interface for inputting the patient data.

103. The system of any of aspects 100-102 further comprising:
- a glucose measurement device in communication with the controller and for measuring the glucose data, including a glucose concentration, in the patient.

104. A system to control glycemia in a patient, the system comprising:
  a controller configured to:
    receive patient data including a basal dose,
    receive glucose data,
    execute a model-predictive controller algorithm to estimate physiological glucose based in part on received glucose data,
    determine an optimal deviation from the basal dose,
    multiply the optimal deviation by a factor,
    set a dose request equal to a sum of a factored, optimal deviation and the basal dose when the optimal deviation is less than a predetermined threshold, and
    set the dose request equal to a sum of the optimal deviation and the basal dose when the optimal deviation is greater than or equal to the predetermined threshold.

105. The system of aspect 104, wherein the predetermined threshold is zero.

106. The system of aspect 104, wherein the factor is greater than one.

107. The system of aspect 104, wherein the factor is greater than 1.3.

108. The system of any of aspects 104-107, further comprising:
  an insulin delivery device for delivering insulin to the patient, in response to the dose request; and
  a user interface for inputting the patient data.

109. The system of any of aspects 104-108, further comprising:
  a glucose measurement device in communication with the controller and for measuring the glucose data, including a glucose concentration, in the patient.

110. A system to control glycemia in a patient, the system comprising:
  a controller configured to:
    receive patient data including a basal dose,
    receive glucose data at intervals,
    calculate an average insulin dose, and
    limit a dose request to be equal to or greater than the basal dose for a first period when the average insulin dose for a past second period is less than a predefined insulin threshold.

111. The system of aspect 110, wherein the first period is less than half the second period.

112. The system of aspect 111, wherein the past second period is greater than 1 hour.

113. The system of aspect 110, wherein the predefined insulin threshold is less than 0.1 insulin units per hour.

114. The system of any of aspects 110-113, further comprising:
  an insulin delivery device for delivering insulin to the patient, in response to the dose request; and
  a user interface for inputting the patient data.

115. The system of any of aspects 110-114, further comprising:
  a glucose measurement device in communication with the controller and for measuring the glucose data, including a glucose concentration, in the patient.

116. A system to control glycemia in a patient, the system comprising:
  an insulin delivery device for delivering insulin to the patient;
  a user interface for inputting patient data, the patient data including a total daily dose of insulin and meal data; and
  a controller configured to:
    receive patient data from the user interface,
    define a state vector and an associated model, the state vector comprising state variables including estimated values of insulin, carbohydrate, and physiological glucose in the patient,
    propagate the state vector,
    correct the propagated state vector by adding an amount of insulin to an insulin state variable, the amount of added insulin being based on the meal data and the total daily dose of insulin,
    determine a dose request with the corrected-state vector, and
    transmit the dose request to the insulin delivery device.

117. The system of aspect 116, wherein the controller is further configured to correct the propagated state vector by adding an amount of carbohydrate to the carbohydrate value of the state vector based on the meal data.

118. The system of any of aspects 116 and 117, wherein the meal data is a meal announcement.

119. The system of any of aspects 116 and 117, wherein the meal data is a meal size selected from two or more choices.

120. The system of any of aspects 116 and 117, wherein the meal data comprises an estimate of the carbohydrate content.

121. A system to provide closed loop control of glycemia in a patient, the system comprising:
  an insulin delivery device for delivering insulin to the patient;
  a user interface for inputting patient data, the patient data including a basal insulin profile, an insulin-to-carbohydrate ratio, and meal data; and
  a controller in communication with the user interface and the insulin delivery device and configured to receive glucose data, the controller is further configured to execute:
    estimating an amount of active insulin in the patient, the active insulin not including the basal insulin profile,
    determining a meal carbohydrate value from the meal data,
    estimating a physiological glucose for the patient and a rate of change of physiological glucose based in part on the glucose data,
    determining an attenuation factor based on the physiological glucose and the rate of change of the physiological glucose,
    determining a meal bolus based on meal data, the insulin-to-carbohydrate ratio, and the determined attenuation factor,
    modifying the determined meal bolus based on the estimated amount of active insulin in the patient, and
    transmitting a request to deliver the modified meal bolus to the insulin delivery device.

122. The system of aspect 121, wherein the controller is configured to:
  control glycemia in the patient after the meal bolus by defining a plurality of state vectors and associated models, each state vector comprising state variables including estimated values of insulin, carbohydrate, and physiological glucose in the patient, each model comprising equations and parameters defining the propagation of the state vector,
  propagate the plurality of state vectors,
  filter the propagated state vectors with a Kalman filter and the glucose data,
  select a state vector and its associated model based on current and past glucose data, use the selected state vector and its associated model to predict the physiological glucose and to solve an objective function for an optimal insulin trajectory, determine an insulin dose request from the optimal insulin trajectory, and transmit the dose request to the insulin delivery device.

123. The system of aspect 122, wherein the controller is configured to determine the rate of change of physiological glucose based on values of the estimated physiological glucose of the most recently selected state vectors.

124. The system of aspect 121, wherein the patient data further includes insulin need, and wherein the controller is configured to limit the attenuated meal bolus to less than a fraction of the insulin need.

125. The system of aspect 124, wherein the insulin need is a total daily dose of insulin.

126. The system of aspect 124, wherein the fraction is less than a quarter.

127. The system of aspect 121, wherein the controller is further configured to:

estimate the amount of insulin in the body, and determine a correction bolus based on the estimated physiological glucose, wherein the correction bolus is zero when the estimated physiological glucose is below a first glucose threshold, and wherein the correction bolus is based on the physiological glucose and the amount of insulin in the patient when the estimated physiological glucose is above the first glucose threshold.

128. The system of aspect 127, wherein the correction bolus increases proportionally to increases in the estimated physiological glucose and the correction bolus decreases proportionally to increases in the estimated insulin in the patient, when the physiological glucose is the above a low physiological glucose threshold.

129. The system of aspect 127, wherein the correction bolus increases proportionally to increases in the estimated physiological glucose at a first rate when the estimated physiological glucose is above a first physiological glucose threshold, wherein the correction bolus increases proportionally to the increases in the estimated physiological glucose at a second rate when the physiological glucose is above a second glucose threshold, wherein the second glucose threshold is above the first threshold, and wherein the first rate is greater than the second rate.

130. The system of any of aspects 121-129, further comprising:

a glucose measurement device in communication with the controller and for measuring glucose data, including a glucose concentration, in the patient.

131. A system to provide closed loop control of glycemia in a patient, the system comprising:

a controller configured to:

receive patient data including an insulin-to-carbohydrate ratio and meal data, receive glucose data, determine a meal carbohydrate value from the meal data, estimate physiological glucose for the patient and a rate of change of physiological glucose based in part on the glucose data, determine a preliminary meal bolus based on the meal data and the insulin-to-carbohydrate ratio, determine an attenuation factor based on the estimated physiological glucose and the rate of change of the physiological glucose, attenuate the preliminary meal bolus proportionally to a meal-carbohydrate value if the meal-carbohydrate value is above a predetermined meal-carbohydrate threshold, attenuate the preliminary meal bolus proportionally to the meal-carbohydrate threshold if the meal-carbohydrate value is equal to or less than the predetermined meal-carbohydrate threshold, and set a dose request equal to the attenuated preliminary meal bolus.

132. The system of aspect 131, further comprising:

an insulin delivery device for delivering insulin to the patient, in response to the dose request; and a user interface for inputting the patient data.

133. The system of any of aspects 131 and 132, further comprising:

a glucose measurement device in communication with the controller and for measuring the glucose data, including a glucose concentration, in the patient.

134. A system to provide closed loop control of glycemia in a patient, the system comprising:

a controller configured to execute control logic for:

receiving patient data including meal data, receiving glucose data, determining a physiological-glucose value and a rate of change of the physiological-glucose based in part on the glucose data, setting a medication dose request to zero when the rate of change of the physiological-glucose is more than a glucose rate threshold, the glucose rate threshold being a predetermined function of the physiological-glucose value, determining the medication dose request based on a predetermined function of the physiological-glucose value and the rate of change of physiological glucose when the rate of change of the physiological-glucose is more than the glucose rate threshold, and transmitting the medication dose request to a medication delivery device.

135. The system of aspect 134, wherein the controller is configured to receive exercise data and reduce the physiological-glucose value used to determine the medication dose request.

136. The system of aspect 134, wherein the controller is configured to determine an amount of active insulin within the patient and modify the medication dose request based in part on the amount of active insulin.

137. The system of aspect 134, wherein the controller is configured to set the medication dose request to zero when a plasma glucose level above a predetermined value.

138. The system of aspect 134, wherein the controller is configured to receive insulin need data and modify medication dose request based in part on the insulin need data.

139. The system of aspect 134, wherein the controller is configured to determine the physiological glucose value with a state vector and its associated model that have been selected from a plurality of state vectors and their associated models, wherein the selection of the state vector and its associated model is based on a comparison of current and past physiological glucose values estimated by each state vector and its associated model verses past and current glucose data.

140. The system of any of aspects 134-139, wherein the medication dose comprises glucagon.

141. The system of any of aspects 134-140, further comprising:

the medication delivery device for delivering a medication dose to the patient, in response to the medication dose request; and a user interface for inputting the patient data.

142. The system of any of aspects 136-141, further comprising:

a glucose measurement device in communication with the controller and for measuring the glucose data, including a glucose concentration, in the patient.

143. A system to provide closed loop control of glycemia in a patient, the system comprising:

a controller configured to:

receive glucose data, receive a basal insulin profile, use a multi-compartment model and the glucose data to determine a physiological-glucose value, a rate of change of the physiological-glucose value, and an amount of active insulin in the patient, the active insulin not including the basal insulin profile, determine an initial medication dose based on the physiological-glucose value and the rate of change of physiological-glucose values, modify the initial medication dose based on the amount of active insulin in the patient to determine the medication dose request, and transmit a medication dose request.

144. The system of aspect 143, wherein the controller is configured to receive a meal announcement and set the medication dose request to zero when a meal has been consumed within a predefined period.

145. The system of aspect 143, wherein when the physiological-glucose value is above a first predetermined level, the controller is configured to set the medication dose request to a first predetermined value when the rate of change of the physiological-glucose is greater than a predetermined rate and set the medication dose request to a second predetermined value when the rate of change of physiological-glucose is less than or equal to the predetermined rate.

146. The system of any of aspects 143-145, further comprising:

a medication delivery device for delivering medication to the patient, in response to the medication dose request; and a user interface for inputting the basal insulin profile.

147. The system of any of aspects 143-146, further comprising:

a glucose measurement device in communication with the controller and for measuring the glucose data, including a glucose concentration, in the patient.

148. A system to provide closed loop control of glycemia in a patient, the system comprising:

a controller configured to:

receive patient data including meal data, receive glucose data, determine a physiological-glucose value and a rate of change of the physiological-glucose value based in part on the glucose data, set a medication dose request to zero when a meal has been consumed within a predefined period, set the medication dose request to a value based on the physiological-glucose value when a meal has not been consumed within a predefined period, and transmit the medication dose request.

149. The system of aspect 148, further comprising:

a medication delivery device for delivering medication to the patient, in response to the medication dose request, the medication being a counter regulatory agent to insulin; and a user interface for inputting the patient data.

150. The system of any of aspects 148 and 149, further comprising:

a glucose measurement device in communication with the controller and for measuring the glucose data, including a glucose concentration, in the patient.

151. A system to control glycemia in a patient, the system comprising:

a controller configured to:

receive glucose data at intervals, define a model, state variables, and covariance matrix, wherein the model controls propagation of the state variables; the state variables comprise an estimated insulin, estimated carbohydrate, and estimated physiological glucose in the patient; and the covariance matrix comprises a diagonal element associated with each state variable;

at each interval, propagate the state variables in time and filter the propagated state variables using the covariance matrix applied with a Kalman filter to produce filtered-state variables, modify one of filtered-state variables as needed to limit a difference between the modified-state variable and the propagated state variable, determine a dose request using the modified-state variable, and transmit the dose request.

152. The system of aspect 151, wherein the controller is configured to modify a filtered-state variable for carbohydrates to be greater than or equal to a predetermined value less than an unfiltered-state variable for carbohydrate.

153. The system of aspect 151, wherein the controller is configured to modify a filtered-state variable for insulin to values less than or equal to a predetermined amount more than an unfiltered-state variable for insulin.

154. The system of any of aspects 151-153, further comprising:

an insulin delivery device for delivering insulin to the patient, in response to the dose request.

155. The system of any of aspects 151-154, further comprising:

a glucose measurement device in communication with the controller and for measuring the glucose data, including a glucose concentration, in the patient.

156. A system to control glycemia in a patient, the system comprising:

a controller configured to:

receive glucose data at intervals, define a model, state variables, and covariance matrix, wherein the model controls propagation of the state variables; the state variables comprise an estimated insulin, estimated carbohydrate, and estimated physiological glucose in the patient; and the covariance matrix comprises a diagonal element associated with each state variable, at each interval, propagate the state variables in time and filter the propagated-state variables using the covariance matrix applied with a Kalman filter to produce filtered-state variables, modify a filtered-state variable to limit a difference between the modified-state variable and a predefined value, determine a dose request using the modified-state variable, and transmit the dose request.

157. The system of aspect 156, wherein the controller is configured to modify the filtered-state variable for insulin to be greater than or equal to a predetermined fraction of a basal dose.

158. The system of any of aspects 156 and 157, further comprising:

an insulin delivery device for delivering insulin to the patient, in response to the dose request.

159. The system of any of aspects 156-158, further comprising:

a glucose measurement device in communication with the controller and for measuring the glucose data, including a glucose concentration, in the patient.

160. A system to control glycemia in a patient, the system comprising:

a controller configured to:

receive glucose data from a glucose measurement device at intervals, define a model, state variables, and covariance matrix, wherein the model controls propagation of the state variables; the state variables comprise an estimated insulin, estimated carbohydrate, and estimated physiological glucose in the patient; and the covariance matrix comprises a diagonal element associated with each state variable, in the event of no meal occurring for a predefined amount of time, set a carbohydrate diagonal element to a value based on a predetermined function of the glucose data and insulin need data and set cross terms of the carbohydrate diagonal value to zero, at each interval, propagate the state variables in time and filter the propagated-state variables using the covariance matrix applied with a Kalman filter to produce filtered-state variables, determine a dose request using the filtered-state variable, and transmit the dose request to an insulin delivery device.

161. The system of aspect 160, further comprising:

an insulin delivery device for delivering insulin to the patient, in response to the dose request.

162. The system of any of aspects 160 and 161, further comprising:

a glucose measurement device in communication with the controller and for measuring the glucose data, including a glucose concentration, in the patient.

163. A system to control glycemia in a patient, the system comprising:

a controller configured to:

receive glucose data at intervals, define a model, state variables, and covariance matrix, wherein the model controls propagation of the state variables; the state variables comprise an estimated insulin, estimated carbohydrate, and estimated physiological glucose in the patient; and the covariance matrix comprises a diagonal element associated with each state variable, the physiological glucose and basal insulin diagonal elements are initialized as functions of the glucose data and insulin need data, when a sum of carbohydrates exceeds a threshold and an average meal time is between a low threshold and a high threshold, set a carbohydrate diagonal element to a non-zero value based on a predetermined function of the glucose data and set a bolus insulin diagonal element to a value based on a predetermined function of the insulin need, propagate the state variables in time, filter the propagated-state variables using the covariance matrix applied with a Kalman filter to produce filtered-state variables, determine a dose request using the filtered-state variable, and transmit the dose request.

164. The system of aspect 163, further comprising:

an insulin delivery device for delivering insulin to the patient, in response to the dose request.

165. The system of any of aspects 163 and 164, further comprising:

a glucose measurement device in communication with the controller and for measuring the glucose data, including a glucose concentration, in the patient.

166. A system to control glycemia in a patient, the system comprising:

a controller is configured to:

receive glucose data at intervals, determine a glucose target, execute a model-predictive controller algorithm to predict physiological glucose values and to solve an objective function for an optimal insulin trajectory, the objective function comprising a sum of weighted differences between the predicted physiological glucose and the glucose target, wherein the weighting increases with time after a meal up to a constant weighting at a predetermined period after a meal determine the dose request from the optimal insulin trajectory, and transmit the dose request.

167. The system of aspect 166, further comprising:

an insulin delivery device for delivering insulin to the patient, in response to the dose request.

168. The system of any of aspects 166 and 167, further comprising:

a glucose measurement device in communication with the controller and for measuring the glucose data, including a glucose concentration, in the patient.

169. A system to control glycemia in a patient, the system comprising:

a controller configured to:

receive glucose data at constant intervals, define a model, state variables, and covariance matrix, wherein the model controls propagation of the state variables; the state variables comprise the estimated insulin, estimated carbohydrate, and estimated physiological glucose in the patient; and the covariance matrix comprises a diagonal element associated with each state variable, at each fraction of an interval, propagate the state variables in time, at each full interval, propagate the state variables in time and filter the propagated state variables using the covariance matrix applied with a Kalman filter to produce filtered-state variables; and determine a dose request using the filtered-state variables, and transmit the dose request.

170. The system of aspect 169, further comprising:

an insulin delivery device for delivering insulin to the patient, in response to the dose request.

171. The system of any of aspects 169 and 170, further comprising:

a glucose measurement device in communication with the controller and for measuring the glucose data, including a glucose concentration, in the patient.

172. A system to control glycemia in a patient, the system comprising:

a controller configured to:

receive glucose data at intervals, use multiple state vectors and their models in a model-predictive control algorithm, wherein the state vectors comprise an estimated insulin, the estimated carbohydrate, and the estimated physiological glucose in the patient, and the model controls propagation of the state vectors, at each interval, propagate the state vectors in time, filter the state vectors based on glucose data, and then select a state vector and its model based on current and past glucose data, use the selected model in model-predictive control algorithm to determine a dose request, and transmit the dose request.

173. The system of aspect 172, further comprising:

an insulin delivery device for delivering insulin to the patient, in response to the dose request.

174. The system of any of aspects 172 and 173, further comprising:

a glucose measurement device in communication with the controller and for measuring the glucose data, including a glucose concentration, in the patient.

175. A system to control glycemia in a patient, the system comprising:

a medication delivery device configured to deliver a medication dose to the patient; and a controller including processors configured to execute:

receiving a current glucose datum at a pre-selected interval, defining a plurality of state vectors, each state vector being associated with a different model, each state vector comprising a body-glucose level, propagating the plurality of state vectors in time based on the associated models, filtering the propagated state vectors based on the current glucose datum, selecting one of the propagated state vectors and its associated model, predicting body-glucose levels during a prediction period with the selected state vector and its associated model, solving an objective function for an optimal medication trajectory during the prediction period, determining the medication dose from the optimal medication trajectory; and transmitting a request to deliver the medication dose to the medication delivery device.

176. The system of aspect 175, wherein the medication is selected from the group including insulin, GLP-1, Pramlintide, amylin and an amylin analogue.

177. The system of any of aspects 175 and 176, further comprising:

a glucose measurement device in communication with the controller and for measuring the glucose data in the patient.

178. A method to control glycemia in a patient, the method comprising:

defining a plurality of state vectors, each state vector being associated with a different model, each state vector comprising a physiological-glucose level; and executing the following at pre-selected intervals:

measuring a current glucose concentration in the patient, transmitting the current glucose concentration to a controller, receiving the current glucose concentration, propagating the plurality of state vectors in time based on the associated models, filtering the propagated state vectors based on the current glucose concentration, selecting one of the propagated state vectors and the associated model, predicting, with the selected state vector and the associated model, a physiological-glucose trajectory during a prediction period, solving an objective function for an optimal insulin trajectory during the prediction period using the physiological-glucose trajectory, and determining an insulin dose from the optimal insulin trajectory.

179. The method of aspect 178, further comprising:

further executing the following steps at the pre-selected intervals:

storing in a memory the physiological-glucose level for each state vector and the glucose concentration, recalling from the memory the physiological-glucose level for each state vector and glucose concentration for a plurality of past intervals, and basing the selection of one of the propagated state vectors and the associated model on the physiological-glucose levels and the glucose concentrations recalled from the memory.

180. The method of aspect 179, further comprising:

further executing the following steps at the pre-selected intervals:

determining an error of the physiological-glucose level for each state vector relative to the glucose concentration, storing in memory the physiological-glucose error, recalling from the memory the physiological-glucose errors of each state vector for a plurality of past intervals, and basing the selection of one of the state vector and the associated model on the sum of the physiological-glucose errors for each state vector.

181. The method of any of aspects 178-180, further comprising:

providing a glucose measurement device for measuring the current glucose concentration, an insulin delivery device, and the controller in communication with the glucose measurement device and the insulin delivery device.

182. The method of aspect 181, further comprising:

transmitting, to the insulin delivery device, a request to deliver the insulin dose; and delivering the insulin dose to the patient with the insulin delivery device.

183. A method to control glycemia in a patient, the method comprising:

receiving, at a controller, glucose concentration and patient data including a basal insulin dose;

estimating a physiological glucose of the patient based at least in part on the glucose concentration;

determining an optimal insulin deviation from the basal insulin dose;

determining that the optimal insulin deviation is less than a predetermined threshold;

setting a factor to a value greater than one in response to determining that the optimal insulin deviation is less than the predetermined threshold; and determining an insulin dose by adding the basal insulin dose to the value of the optimal insulin deviation times the factor.

184. The method of aspect 183, wherein the predetermined threshold is zero.

185. The method of aspect 183, wherein the factor is greater than 1.3.

186. The method of any of aspects 183-185, further comprising:

providing a glucose measurement device for measuring the glucose concentration in the patient, an insulin delivery device, a user interface, and the controller in communication with the glucose measurement device, the insulin delivery device, and the user interface; and inputting the patient data to the user interface.

187. The method of aspect 186, further comprising:

transmitting, to the insulin delivery device, a request to deliver the insulin dose; and delivering the insulin dose to the patient with the insulin delivery device.

188. A method to control glycemia in a patient, the method comprising:

receiving, at a controller, a glucose concentration and patient data;

estimating a physiological glucose of the patient based at least in part on and the glucose concentration;

determining an insulin dose, in response to the estimated physiological glucose;

determining that an average insulin dose for a past second period of time is less than a predefined insulin threshold; and limiting the insulin dose to be equal to or greater than a basal insulin dose for a first period of time in response determining that an average insulin dose for a past second period of time is less than the predefined insulin threshold.

189. The method of aspect 188, wherein the first period of time is less than half the past second period of time.

190. The method of aspect 189, wherein the past second period of time is greater than 1 hour.

191. The method of aspect 188, wherein the predefined insulin threshold is less than 0.1 insulin units per hour.

192. The method of any of aspects 188-191, further comprising:

providing a glucose measurement device for measuring the glucose concentration in the patient, an insulin delivery device, a user interface, and the controller in communication with the glucose measurement device, the insulin delivery device, and the user interface; and inputting the patient data to the user interface including the basal insulin dose.

193. The method of aspect 192, further comprising:

transmitting, to the insulin delivery device, a request to deliver the insulin dose; and delivering the insulin dose to the patient with the insulin delivery device.

194. A method to control glycemia in a patient, the method comprising:

receiving, at a controller, a glucose concentration, a total daily dose of insulin, and meal data;

defining a state vector and model, the state vector comprising one or more insulin state variables, one or more carbohydrate state variables, and a physiological glucose state variable;

propagating the state vector in time based on the model;

filtering the propagated state vector based on the glucose concentration;

adding an amount of insulin to at least one insulin state variable, the amount of added insulin being based on the meal data and the total daily dose of insulin; and determining an insulin dose based on the state vector and associated model.

195. The method of aspect 194, further comprising:

adding an amount of carbohydrate to at least one of the carbohydrate state variables based on the meal data.

196. The method of any of aspects 194 and 195, further comprising:

providing a glucose measurement device for measuring the glucose concentration in the patient, an insulin delivery device, a user interface, and the controller in communication with the glucose measurement device, the insulin delivery device, and the user interface; and inputting patient data to the user interface, the patient data including the meal data and the total daily dose of insulin.

197. The method of aspect 196, further comprising:

transmitting, to the insulin delivery device, a request to deliver the insulin dose; and delivering the insulin dose to the patient with the insulin delivery device.

198. A method to provide closed loop control of glycemia in a patient, the method comprising:

receiving, at a controller, a basal insulin dose, meal data, and an insulin-to-carbohydrate ratio;

estimating an active insulin in the patient, the active insulin in the patient not including the basal insulin dose;

estimating a physiological glucose for the patient and a rate of change of physiological glucose based in part on a glucose concentration;

determining a meal carbohydrate value from the meal data;

determining an attenuation factor based on the estimated physiological glucose and the rate of change of the physiological glucose;

determining a meal bolus based on meal data, the insulin-to-carbohydrate ratio, and the attenuation factor; and modifying the meal bolus based on the active insulin in the patient.

199. The method of aspect 198, further comprising:

providing a glucose measurement device for measuring the glucose concentration in the patient, an insulin delivery device, and a user interface, the controller in communication with the glucose measurement device, the insulin delivery device, and the user interface.

200. The method of aspect 199, further comprising:

transmitting, to the insulin delivery device, a request to deliver the modified meal bolus; and delivering the modified meal bolus to the patient with the insulin delivery device.

201. A method to provide closed loop control of glycemia in a patient, the method comprising the steps:

transmitting a glucose concentration, a basal insulin dose, and a meal data to a controller;

estimating an active insulin in the patient, the active insulin in the patient not including the basal insulin dose;

estimating a physiological glucose for the patient and a rate of change of physiological glucose based in part on the glucose concentration;

determining a meal carbohydrate value from the meal data;

determining an attenuation factor based on the estimated physiological glucose and rate of change of the physiological glucose;

determining a meal bolus based on the meal data, an insulin-to-carbohydrate ratio, and the attenuation factor, wherein the meal bolus is attenuated proportionally to a meal-carbohydrate value when the meal-carbohydrate value is above a predetermined meal-carbohydrate threshold, and wherein the meal bolus is attenuated proportionally to the predetermined meal-carbohydrate threshold for a meal-carbohydrate value equal to or less than the predetermined meal-carbohydrate threshold.

202. The method of aspect 201, further comprising:

providing a glucose measurement device for measuring the glucose concentration in the patient, an insulin delivery device, a user interface, and the controller in communication with the glucose measurement device, the insulin delivery device, and the user interface; and inputting patient data to the user interface, the patient data including the meal data and the basal insulin dose.

203. The method aspect 202, further comprising:

transmitting, to the insulin delivery device, a request to deliver the meal bolus; and delivering the meal bolus to the patient with the insulin delivery device.

204. A method to provide closed loop control of glycemia in a patient, the method comprising the steps:

transmitting a glucose concentration to a controller;

estimating a physiological glucose for the patient and a rate of change of physiological glucose;

determining a glucose rate threshold based on the estimated physiological glucose;

setting the medication dose request to zero when the rate of change of the physiological glucose is more than a glucose rate threshold; and determining the medication dose request based on a predetermined function of the physiological glucose and the rate of change of physiological glucose when the rate of change of the physiological glucose is more than the glucose rate threshold.

205. The method of aspect 204, further comprising:

providing a glucose measurement device for measuring the glucose concentration in the patient, a medication delivery device, and a user interface, the controller in communication with the glucose measurement device, the medication delivery device, and the user interface.

206. The method of aspect 205, further comprising:

transmitting, to the medication delivery device, the medication dose request; and delivering the medication dose to the patient with the medication delivery device.

207. A method to provide closed loop control of glycemia in a patient, the method comprising the steps:

transmitting a glucose concentration, a basal insulin dose, and meal data to a controller;

determining a physiological-glucose value, a rate of change of the physiological-glucose value, and an amount of active insulin in the patient, the active insulin in the patient not including the basal insulin profile;

determining an medication dose based on the determined physiological glucose value and the rate of change of physiological glucose values; and modifying the medication dose based on the amount of active insulin in the patient.

208. The method of aspect 207, further comprising:

providing a glucose measurement device for measuring the glucose concentration in the patient, a medication delivery device, a user interface, and the controller in communication with the glucose measurement device, the medication delivery device, and the user interface; and inputting patient data to the user interface, the patient data including the meal data and the basal insulin dose.

209. The method of aspect 208, further comprising:

transmitting, to the medication delivery device, the modified medication dose; and delivering the modified medication dose to the patient with the medication delivery device.

210. A method to provide closed loop control of glycemia in a patient, the method comprising the steps:

transmitting a glucose concentration and meal data to a controller;

estimating a physiological glucose for the patient and a rate of change of physiological glucose based in part on the glucose concentration;

setting a medication dose to zero when a meal has been consumed within a predefined period; and determining the medication dose based on the physiological glucose when a meal has not been consumed within a predefined period.

211. The method of aspect 210, further comprising:

providing a glucose measurement device for measuring the glucose concentration in the patient, a medication delivery device, a user interface, and the controller in communication with the glucose measurement device, the medication delivery device, and the user interface; and inputting patient data to the user interface, the patient data including the meal data.

212. The method of aspect 211, further comprising:

transmitting, to the medication delivery device, the medication dose; and delivering the medication dose to the patient with the medication delivery device.

213. A method to control glycemia in a patient, the method comprising:

defining a plurality of state vectors, each state vector being associated with a different model and a different covariance matrix, the plurality of state vectors comprising one or more insulin state variables, one or more carbohydrate state variables, and a physiological glucose state variable;

propagating the plurality of state vectors in time based on the associated models;

filtering the propagated plurality of state vectors with a Kalman filter using the associated covariance matrixes and a glucose concentration;

modifying one of the insulin state variables in at least one filtered state vector to limit a difference in the state variable between the at least one filtered-state vector and the at least one unfiltered-state vector;

selecting one of the filtered-state vectors and the associated model;

predicting a physiological-glucose trajectory during a prediction period with the selected filtered-state vector and the associated model;

solving an objective function for an optimal insulin trajectory during the prediction period using the physiological-glucose trajectory; and determining an insulin dose request from the optimal insulin trajectory.

214. The method of aspect 213, further comprising:

providing a glucose measurement device for measuring the glucose concentration in the patient, an insulin delivery device, and a controller in communication with the glucose measurement device and the insulin delivery device.

215. The method of aspect 214, further comprising:

transmitting, to the insulin delivery device, the insulin dose request; and delivering the insulin dose to the patient with the insulin delivery device.

216. A method to control glycemia in a patient, the method comprising:

defining a state vector, a model and a covariance matrix, the state vector comprising an insulin state variable, a carbohydrate state variable, and a physiological glucose state variable;

propagating the state vector in time based on the model;

filtering the propagated state vector with a Kalman filter using the covariance matrix and a glucose concentration;

modifying one state variable in the filtered state vector to limit a difference in the state variable between the filtered-state vector and the unfiltered-state vector; and determining an insulin dose request based on the modified and filtered state vector.

217. The method of aspect 216, wherein the one state variable is a carbohydrates state variable and is modified to limit the carbohydrate state variable to not less than a predetermined value below the unfiltered-state variable for carbohydrate.

218. The method of aspect 216, wherein the one state variable is an insulin state variable and is modified to limit the insulin state variable to not more than a predetermined amount above the unfiltered-state variable for insulin.

219. The method of any of aspects 216-218, further comprising:

providing a glucose measurement device for measuring the glucose concentration in the patient, an insulin delivery device, and a controller in communication with the glucose measurement device and the insulin delivery device.

220. The method of aspect 219, further comprising:

transmitting, to the insulin delivery device, the insulin dose request; and delivering the insulin dose to the patient with the insulin delivery device.

221. A method to control glycemia in a patient, the method comprising:

defining a state vector, a model and a covariance matrix, the state vector comprising an insulin state variable, a carbohydrate state variable, and a physiological glucose state variable;

propagating the state vector in time based on the model;

filtering the propagated state vector with a Kalman filter using the covariance matrix and a glucose concentration;

modifying one state variable in the filtered state vector to limit the difference between the filtered-state variable and a predefined value; and determining an insulin dose request based on the modified and filtered state vector.

222. The method of aspect 221, further comprising:

providing a glucose measurement device for measuring the glucose concentration in the patient, an insulin delivery device, and a controller in communication with the glucose measurement device and the insulin delivery device.

223. The method of aspect 222, further comprising:

transmitting, to the insulin delivery device, the insulin dose request; and delivering the insulin dose to the patient with the insulin delivery device.

224. A method to control glycemia in a patient, the method comprising:

defining a state vector, a model, and a covariance matrix, the state vector comprising an insulin state variable, a carbohydrate state variable, and a physiological glucose state variable, the covariance matrix comprising diagonal elements associated with each state variable and cross terms associated with each diagonal element;

modifying the covariance matrix by setting a carbohydrate diagonal element and the associated cross terms to zero when a meal has not occurred within a predetermined period in the past;

propagating the state vector in time based on the model;

filtering the propagated state vector with a Kalman filter using the modified covariance matrix and a glucose concentration; and determining an insulin dose request based on the filtered state vector.

225. The method of aspect 224, further comprising:

providing a glucose measurement device for measuring the glucose concentration in the patient, an insulin delivery device, and a controller in communication with the glucose measurement device and the insulin delivery device.

226. The method of aspect 225, further comprising:

transmitting, to the insulin delivery device, the insulin dose request; and delivering the insulin dose to the patient with the insulin delivery device.

227. A method to control glycemia in a patient, the method comprising:

defining a state vector, a model and a covariance matrix, the state vector comprising an insulin state variable, a carbohydrate state variable, and a physiological glucose state variable, the covariance matrix comprising diagonal elements associated with each state variable and cross terms associated with each diagonal element;

modifying the covariance matrix by setting a carbohydrate diagonal element to a non-zero value based on a predetermined function of glucose data when a sum of carbohydrates exceeds a threshold and an average meal time is between a low threshold and a high threshold;

modifying the covariance matrix by setting a bolus insulin diagonal element to a non-zero value when a sum of carbohydrates exceeds a threshold and an average meal time is between a low threshold and a high threshold;

propagating the state vector in time based on the model;

filtering the propagated state vector with a Kalman filter using the modified covariance matrix and a glucose concentration; and determining an insulin dose request based on the filtered state vector.

228. The method of aspect 227, further comprising:

providing a glucose measurement device for measuring the glucose concentration in the patient, an insulin delivery device, and a controller in communication with the glucose measurement device and the insulin delivery device.

229. The method of aspect 228, further comprising:

transmitting, to the insulin delivery device, the insulin dose request; and delivering the insulin dose to the patient with the insulin delivery device.

230. A method to control glycemia in a patient, the method comprising:

defining a plurality of state vectors, each state vector being associated with a different model, each state vector comprising a physiological-glucose level;

measuring a current glucose concentration in the patient at a predefined interval;

receiving the glucose concentration at the predefined interval;

propagating each state vector in time based on the associated model at a fraction of the predefined interval;

propagating the state vector in time based on the associated model at the predefined interval;

filtering each propagated state vector based on the current glucose concentration at the predefined interval;

selecting one of the filtered and propagated state vectors and the associated model based in part on the physiological-glucose values of each state vector and the current glucose concentration at the predefined interval;

predicting a physiological-glucose trajectory during a prediction period with the selected state vector and the associated model at the predefined interval;

solving an objective function for an optimal insulin trajectory during the prediction period using the physiological-glucose trajectory at the predefined interval; and determining an insulin dose request from the optimal insulin trajectory at the predefined interval.

231. The method of aspect 230, further comprising:

providing a glucose measurement device for measuring the current glucose concentration in the patient, an insulin delivery device, and a controller in communication with the glucose measurement device and the insulin delivery device.

232. The method of aspect 231, further comprising:

transmitting, to the insulin delivery device, the insulin dose request; and delivering the insulin dose to the patient with the insulin delivery device.

233. A method to control glycemia in a patient, the method comprising:

defining a plurality of state vectors, each state vector being associated with a different model and comprising a physiological-glucose value;

measuring a current glucose concentration in the patient at a first predefined interval;

receiving the glucose concentration at the first predefined interval;

propagating each state vector in time based on the associated model at the first predefined interval;

filtering each state vector based on the current glucose concentration at the first predefined interval;

selecting one of the state vectors and the associated model based in part on the physiological-glucose values of each state vector and a current glucose concentration at a second predefined interval, where the second predefined interval is longer than the first predefined interval;

predicting a physiological-glucose trajectory during a prediction period with the selected state vector and the associated model at the second predefined interval;

solving an objective function for an optimal insulin trajectory during the prediction period using the physiological-glucose trajectory at the second predefined interval; and determining an insulin dose request from the optimal insulin trajectory at the second predefined interval.

234. The method of aspect 233, further comprising:

providing a glucose measurement device for measuring the current glucose concentration in the patient, an insulin delivery device, and a controller in communication with the glucose measurement device and the insulin delivery device.

235. The method of aspect 234, further comprising:

transmitting, to the insulin delivery device, the insulin dose request; and delivering the insulin dose to the patient with the insulin delivery device.

236. A system to control glycemia in a patient, the system comprising:

a medication delivery device configured to deliver a medication dose to the patient;

a user interface configured to generate user data based on at least one user input; and means for determining the medication dose in response to a glucose measurement and the user data.

Various alternatives and modifications may be devised by those skilled in the art without departing from the present disclosure. Accordingly, the present disclosure is intended to embrace all such alternatives, modifications and variances. Additionally, while several embodiments of the present disclosure have been illustrated in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

Furthermore, the terms “first”, “second”, “third” and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A system to control glucose in a patient, the system comprising:

a medication delivery device configured to deliver a medication dose to the patient; and a controller operably coupled to the medication delivery device and including control logic operative to:

execute a multi-model predictive controller algorithm at least in part by executing a plurality of models each comprising a plurality of model parameters having a set of values, wherein executing the plurality of models includes propagating multiple state vectors, select one of the plurality of executed models based at least in part on differences between glucose values of the propagated state vectors and previously measured glucose values, calculate a basal deviation using the selected model, wherein the basal deviation is a dosage amount above or below a predefined basal profile, and determine a first medication dose based at least in part on the calculated basal deviation and the predefined basal profile.

2. The system of claim 1, wherein the control logic is further operative to:

predict future glucose levels of the patient based at least in part on the selected executed model, wherein the determination of the first medication dose is based at least in part on the predicted future glucose levels.

3. The system of claim 2, wherein the control logic is further operative to:

determine a difference between the predicted future glucose levels and a nominal target glucose value, wherein the determination of the first medication dose is based at least in part on the difference between the predicted future glucose levels and the nominal target glucose value.

4. The system of claim 2, wherein the prediction of future glucose levels is based at least in part on the predefined basal profile.

5. The system of claim 2, wherein the prediction of future glucose levels is based at least in part on the predefined basal profile and without meal boluses.

6. The system of claim 1, wherein the control logic being operative to select one of the plurality of executed models comprises the control logic being operative to:

select one of the plurality of executed models in response to comparing a calculated level of interstitial glucose and a measured level of interstitial glucose.

7. The system of claim 6, wherein the measured level of interstitial glucose comprises a plurality of past measured levels of interstitial glucose.

8. The system of claim 1, wherein the control logic being operative to select one of the plurality of executed models comprises the control logic being operative to:

select one of the plurality of executed models based at least in part on a nominal target glucose value.

9. The system of claim 8, wherein the nominal target glucose value is increased in response to an exercise announcement.

10. The system of claim 8, wherein the nominal target glucose value is increased in response to a meal announcement.

11. The system of claim 1, wherein the control logic is further operative to:

re-execute the multi-model predictive controller algorithm, select a different one of the plurality of executed models, and determine a second medication dose based at least in part on the selected executed model.

12. The system of claim 1, wherein the control logic is further operative to:

re-execute the multi-model predictive controller algorithm including re-executing the plurality of models using the plurality of model parameters and the set of values, select a different one of the plurality of executed models, and determine a second medication dose based at least in part on the selected executed model.

13. The system of claim 1, wherein the plurality of model parameters includes at least one of an insulin sensitivity, an insulin time constant, a meal action time constant, a sensor time constant, an insulin-to-carbohydrate ratio, an input from a user interface, and a controller gain value.

14. The system of claim 1, wherein the plurality of model parameters includes an insulin sensitivity, an insulin time constant, a meal action time constant, a sensor time constant, and an insulin-to-carbohydrate ratio.

15. The system of claim 1, wherein each of the plurality of models includes a set of linear differential equations that calculate levels of physiological glucose and interstitial glucose.

16. The system of claim 15, wherein the set of linear differential equations model storage and transportation of insulin in the patient.

17. The system of claim 1, wherein the controller is further operative to transmit a request including the determined first medication dose to the medication delivery device, the medication delivery device includes insulin, and the medication delivery device is configured to deliver the insulin to the patient based at least in part on the determined first medication dose.

18. The system of claim 1, further comprising:

a user interface operably coupled to the controller and configured to receive input from the patient.

19. The system of claim 1, further comprising:

a glucose measurement device operably coupled to the controller and configured to measure glucose data associated with the patient and transmit the measured glucose data to the controller, wherein the determination of the first medication dose is based at least in part on the measured glucose data.

20. A method to control glucose in a patient, the method comprising:

executing, using one or more controllers, a multi-model predictive controller algorithm by executing a plurality of models each of which comprise a plurality of model parameters having a set of values, wherein executing the plurality of models includes propagating multiple state vectors;

selecting, using the one or more controllers, one of the plurality of executed models based at least in part on differences between glucose values of the propagated state vectors and previously measured glucose values;

calculating, using the one or more controllers, a basal deviation using the selected model, wherein the basal deviation is a dosage amount above or below a predefined basal profile;

determining, using the one or more controllers, a first medication dose based at least in part on the calculated basal deviation and the predefined basal profile; and transmitting, using the one or more controllers, the first medication dose to a medication delivery device configured to deliver the medication dose to the patient.

21. The method of claim 20, further comprising:

predicting, using the one or more controllers, future glucose levels of the patient based at least in part on the selected executed model, wherein the determination of the first medication dose is based at least in part on the predicted future glucose levels.

22. The method of claim 21, further comprising:

determining, using the one or more controllers, a difference between the predicted future glucose levels and a nominal target glucose value, wherein the determination of the first medication dose is based at least in part on the difference between the predicted future glucose levels and the nominal target glucose value.

23. The method of claim 21, wherein the prediction of future glucose levels is based at least in part on the pre-defined basal profile.

24. The method of claim 20, further comprising:

re-executing the multi-model predictive controller algorithm including re-executing the plurality of models using the plurality of model parameters and the set of values;

selecting a different one of the plurality of executed models; and determining a second medication dose based at least in part on the selected executed model.

25. The method of claim 20, wherein the plurality of model parameters includes an insulin sensitivity, an insulin time constant, a meal action time constant, a sensor time constant, and an insulin-to-carbohydrate ratio.

26. The method of claim 20, wherein executing a plurality of models includes executing a set of linear differential equations to calculate levels of physiological glucose and interstitial glucose, wherein the set of linear differential equations model storage and transportation of insulin in the patient.

27. The method of claim 20, wherein selecting one of the plurality of executed models is in response to comparing a calculated level of interstitial glucose and a measured level of interstitial glucose.

28. The method of claim 20, wherein selecting one of the plurality of executed models is based at least in part on a nominal target glucose value.

* * * * *